United States Patent
Iwasaki et al.

(10) Patent No.: US 10,514,621 B2
(45) Date of Patent: Dec. 24, 2019

(54) ELECTROPHOTOGRAPHIC PHOTORECEPTOR, PROCESS CARTRIDGE, IMAGE FORMING APPARATUS, AND IMIDE COMPOUND

(71) Applicant: FUJI XEROX CO., LTD., Tokyo (JP)

(72) Inventors: Masahiro Iwasaki, Kanagawa (JP); Ryosuke Fujii, Kanagawa (JP); Kenji Kajiwara, Kanagawa (JP); Wataru Yamada, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 16/055,371

(22) Filed: Aug. 6, 2018

(65) Prior Publication Data
US 2019/0317415 A1 Oct. 17, 2019

(30) Foreign Application Priority Data

Apr. 11, 2018 (JP) ................... 2018-076119
Apr. 11, 2018 (JP) ................... 2018-076120

(51) Int. Cl.
*G03G 5/00* (2006.01)
*G03G 5/06* (2006.01)
(Continued)

(52) U.S. Cl.
CPC ......... *G03G 5/0661* (2013.01); *C07D 471/06* (2013.01); *G03G 5/14* (2013.01);
(Continued)

(58) Field of Classification Search
CPC ......... G03G 5/0661; G03G 5/14; G03G 5/144
(Continued)

(56) References Cited

U.S. PATENT DOCUMENTS

| | | |
|---|---|---|
| 5,223,364 A | 6/1993 | Maeda et al. |
| 6,127,076 A | 10/2000 | Ishigami et al. |

(Continued)

FOREIGN PATENT DOCUMENTS

| | | |
|---|---|---|
| JP | 4-285670 A | 10/1992 |
| JP | 4-338969 A | 11/1992 |

(Continued)

*Primary Examiner* — Mark A Chapman
(74) *Attorney, Agent, or Firm* — Sughrue Mion, PLLC

(57) ABSTRACT

An electrophotographic photoreceptor includes a conductive substrate; a photosensitive layer provided on the conductive substrate; and an undercoating layer that is provided between the conductive substrate and the photosensitive layer and includes a charge transport material containing at least one of imide compounds represented by Formula (1) or (2):

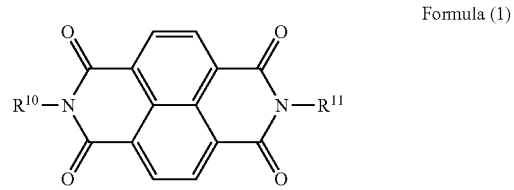

Formula (1)

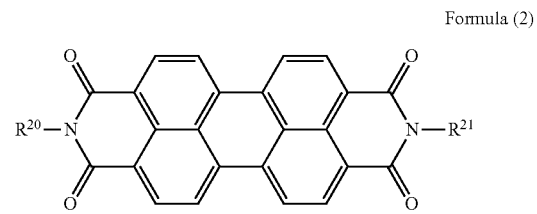

Formula (2)

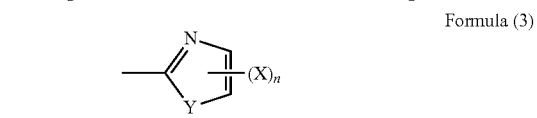

Formula (3)

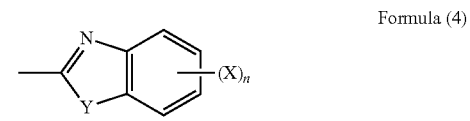

Formula (4)

(in Formulas (1) and (2), $R^{10}$, $R^{11}$, $R^{20}$, or $R^{21}$ independently represents a group represented by Formula (3) or (4) where X represents a monovalent organic group (Continued)

having at least one of an alkyl group, an alkylene group, an ether group, an ester group, and a keto group, a halogen atom, a nitro group, an aralkyl group, or an aryl group, Y represents a sulfur atom or an oxygen atom, n represents an integer of 0 to 2, and when n represents 2, two X's may be the same or different), and an imide compound is represented by Formula (1A) where Ar represents an aromatic group having 6 to 18 carbon atoms except for a tetravalent perylene group, $X^1$ and $X^2$ each independently represent a nitrogen atom or a substituted or unsubstituted carbon atom, $Y^1$ and $Y^2$ each independently represent an oxygen atom, a sulfur atom, a selenium atom, or NH, and $R^1$ and $R^2$ each independently represent a hydrogen atom or a monovalent organic group:

Formula (1A)

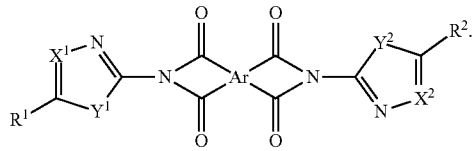

9 Claims, 6 Drawing Sheets

(51) Int. Cl.
G03G 15/00 (2006.01)
C07D 471/06 (2006.01)
G03G 5/14 (2006.01)

(52) U.S. Cl.
CPC ............ *G03G 5/142* (2013.01); *G03G 5/144* (2013.01); *G03G 15/75* (2013.01)

(58) Field of Classification Search
USPC .......................................................... 430/60
See application file for complete search history.

(56) References Cited

U.S. PATENT DOCUMENTS

| 6,174,638 | B1 | 1/2001 | Ishigami et al. |
| 2002/0102484 | A1 | 8/2002 | Miyamoto et al. |
| 2005/0112482 | A1 | 5/2005 | Kim et al. |
| 2016/0054666 | A1 | 2/2016 | Okuda et al. |

FOREIGN PATENT DOCUMENTS

| JP | 5-25136 | A | 2/1993 |
| JP | 05-25174 | A | 2/1993 |
| JP | 7-253682 | A | 10/1995 |
| JP | 11-343290 | A | 12/1999 |
| JP | 11-343291 | A | 12/1999 |
| JP | 2002-116565 | A | 4/2002 |
| JP | 2004-262813 | A | 9/2004 |
| JP | 2005-154444 | A | 6/2005 |
| JP | 2005-208618 | A | 8/2005 |
| JP | 4411232 | B2 | 2/2010 |
| JP | 4498123 | B2 | 7/2010 |
| JP | 5064815 | B2 | 10/2012 |
| JP | 5147274 | B2 | 2/2013 |
| JP | 5975942 | B2 | 8/2016 |

F I G.6
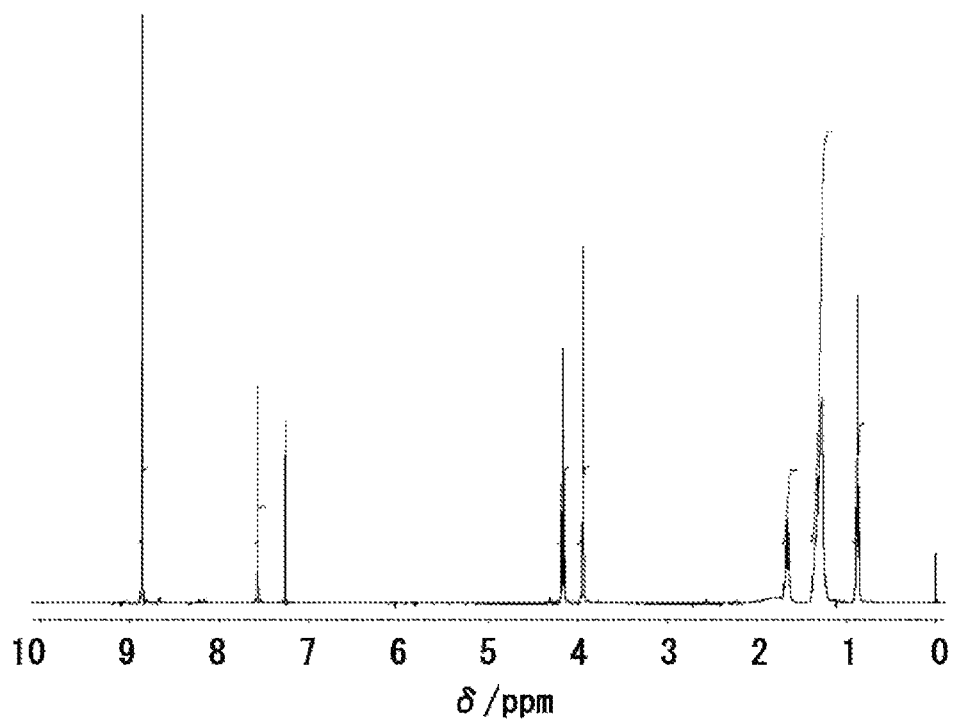

F I G. 7
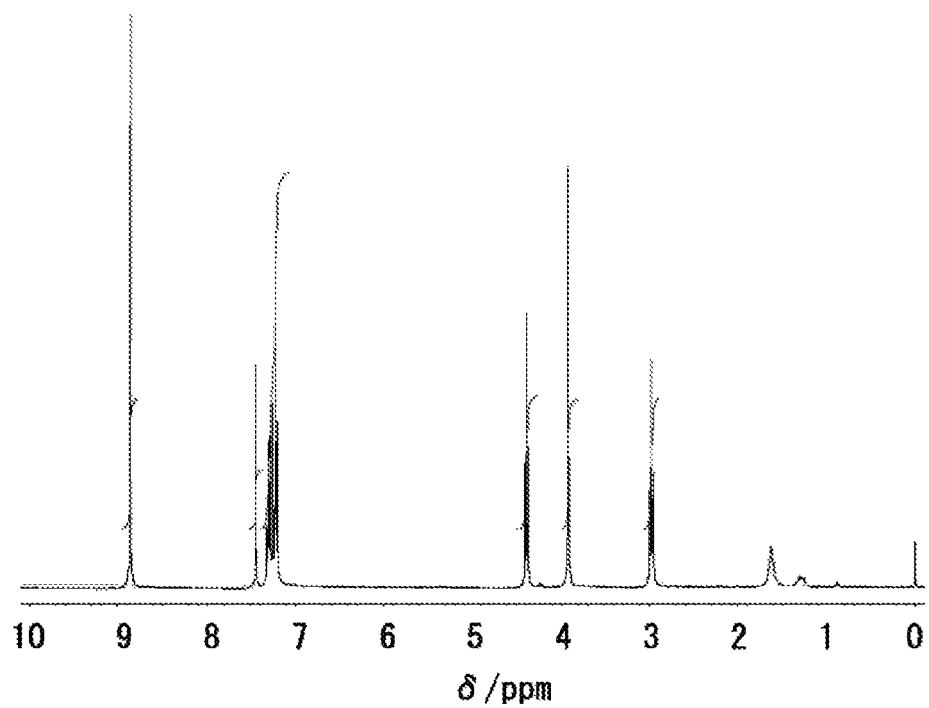

F I G.8
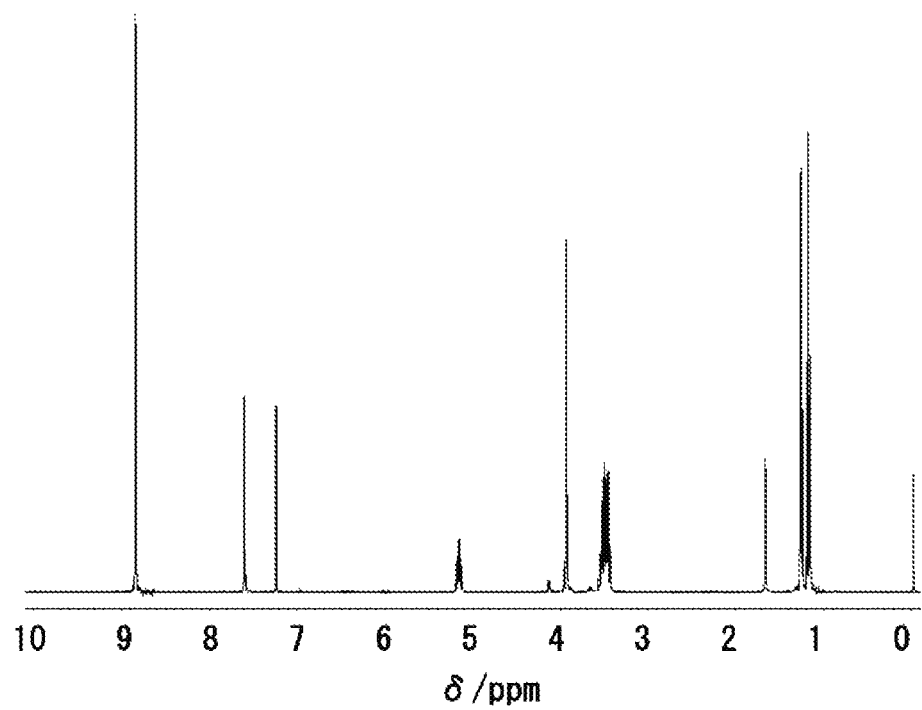

ELECTROPHOTOGRAPHIC PHOTORECEPTOR, PROCESS CARTRIDGE, IMAGE FORMING APPARATUS, AND IMIDE COMPOUND

CROSS-REFERENCE TO RELATED APPLICATIONS

This application is based on and claims priority under 35 USC 119 from Japanese Patent Application No. 2018-076119 filed on Apr. 11, 2018 and Japanese Patent Application No. 2018-076120 filed on Apr. 11, 2018.

BACKGROUND

(i) Technical Field

The present invention relates to an electrophotographic photoreceptor, a process cartridge, an image forming apparatus, and an imide compound.

(ii) Related Art

In the related art, as an electrophotographic image forming apparatus, an apparatus that sequentially performs steps such as charging, forming an electrostatic latent image, developing, transferring, and cleaning, by using an electrophotographic photoreceptor is widely known.

As the electrophotographic photoreceptor, there is known a function-separated photoreceptor in which a charge generation layer that generates charge and a charge transport layer that transports the charge are stacked on a substrate having conductivity such as aluminum or a singlelayer type photoreceptor in which the same layer plays a function of generating charge and a function of transporting charge.

Japanese Patent No. 4411232 discloses a method of manufacturing an electrophotographic photoreceptor, the method including: (a) forming an intermediate layer on a conductive support using an intermediate layer coating material containing particles of polynaphthyl diimide polymer; and (b) forming a photosensitive layer on the intermediate layer.

Japanese Patent No. 4498123 discloses an electrophotographic photoreceptor including a hole transport layer containing a hole transport substance and a charge generation layer containing an electron transport substance in an amount of 21% to 50% by weight with respect to a charge generation substance and an electrophotographic apparatus using the electrophotographic photoreceptor. In addition, there is also disclosed that ghost improves by adding the electron transport substance such as a fluorine-containing bisimide compound.

Japanese Patent No. 5975942 discloses an electrophotographic photoreceptor including a support, an electron transport layer, and a photosensitive layer in this order, in which the electron transport layer is a cured product of a composition including an electron transport substance having a polymerizable functional group, a thermoplastic resin having a polymerizable functional group, and a crosslinking agent and includes a carbon atom, a nitrogen atom, and an oxygen atom which have a standard deviation in a predetermined range when analyzed by X-ray photoelectron spectroscopy.

Japanese Patent No. 5147274 discloses a naphthalene tetracarboxylic acid diimide compound having a structure in which a phenyl group or a hydroxyalkyl group having a substituent is bonded to nitrogen atoms of two imide groups.

In addition, there is also disclosed that the naphthalene tetracarboxylic acid diimide compound may be contained in an intermediate layer.

Japanese Patent No. 5064815 discloses a naphthalene tetracarboxylic acid diimide compound having a structure in which a phenyl group having a substituent is bonded to nitrogen atoms of two imide groups.

In addition, JP-A-2005-208618 discloses an electrophotographic photoreceptor including: a charge generation layer including a charge generation substance and a hole transport layer which is provided on the charge generation layer and contains a hole transport substance, in which the charge generation layer contains an electron transport substance. In addition, there is also disclosed that the naphthalene tetracarboxylic acid diimide compound having a thiophene group may be used as the electron transport substance.

JP-A-07-253682 discloses an electrophotographic photoreceptor including a photosensitive layer on a conductive support, in which a perylene tetracarboxylic acid diimide having a thiazole group or a benzothiazole group is contained in the photosensitive layer.

In addition, in the related art, various charge transport materials used for electrophotographic photoreceptors and the like are known.

For example, JP-A-4-285670 discloses an electrophotographic photoreceptor including a novel diphenoquinone compound and a photosensitive layer containing the compound as a charge transport material.

JP-A-5-25136 discloses a novel naphthalene dicarboxylic acid imide compound.

JP-A-4-338969 discloses an electrophotographic photoreceptor including a conductive substrate and a photosensitive layer that is provided on the conductive substrate and contains a perylene pigment having a specific X-ray diffraction peak as a charge generation material.

JP-A-5-25174 discloses a novel naphthalene tetracarboxylic acid diimide compound.

JP-A-2002-116565 discloses an electrophotographic photoreceptor in which a conductive substrate, an organic photosensitive layer that is provided on the conductive substrate and contains a novel naphthylene diimide derivative, and an inorganic surface protective layer provided on the organic photosensitive layer are laminated.

JP-A-11-343290 and JP-A-11-343291 disclose a novel naphthalene tetracarboxylic acid diimide derivative and an electrophotographic photoreceptor containing the novel naphthalene tetracarboxylic acid diimide derivative.

JP-A-2004-262813 discloses a novel naphthalene tetracarboxylic acid diimide derivative and an electrophotographic photoreceptor including a photosensitive layer containing the novel naphthalene tetracarboxylic acid diimide derivative.

JP-A-07-253682 discloses an electrophotographic photoreceptor including a conductive support and a photosensitive layer that is provided on the conductive support and contains a perylene pigment.

JP-A-2005-154444 discloses a naphthalene tetracarboxylic acid diimide derivative compound and an electrophotographic photoreceptor including a photosensitive layer containing the naphthalene tetracarboxylic acid diimide derivative compound as an electron transport substance.

SUMMARY

Aspects of non-limiting embodiments of the present disclosure relate to an electrophotographic photoreceptor that prevents an increase of the residual potential when images are formed repeatedly, as compared with a case of an electrophotographic photoreceptor including a conductive substrate, a photosensitive layer provided on the conductive substrate, and an undercoating layer that is provided between the conductive substrate and the photosensitive layer and contains Compound (A), Compound (B), or Compound (C) described in the working examples described later as an imide compound and a novel imide compound having an electron transporting ability.

Aspects of certain non-limiting embodiments of the present disclosure overcome the above disadvantages and other disadvantages not described above. However, aspects of the non-limiting embodiments are not required to overcome the disadvantages described above, and aspects of the non-limiting embodiments of the present disclosure may not overcome any of the problems described above.

According to a first aspect of the present disclosure, there is provided an electrophotographic photoreceptor including:
a conductive substrate;
a photosensitive layer provided on the conductive substrate; and
an undercoating layer that is provided between the conductive substrate and the photosensitive layer and includes a charge transport material containing at least one of imide compounds represented by Formula (1) or (2):

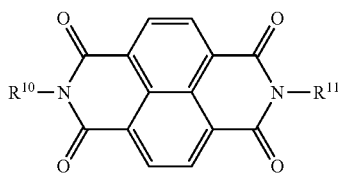

Formula (1)

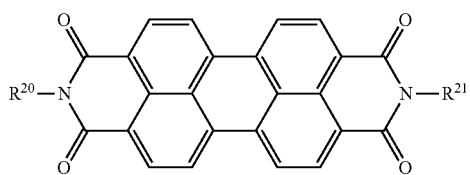

Formula (2)

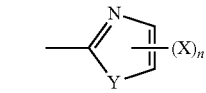

Formula (3)

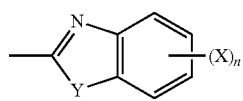

Formula (4)

(in Formulas (1) and (2), $R^{10}$, $R^{11}$, $R^{20}$, or $R^{21}$ independently represents a group represented by Formula (3) or (4); and in Formulas (3) and (4), X represents a monovalent organic group having at least one of an alkyl group, an alkylene group, an ether group, an ester group, and a keto group, a halogen atom, a nitro group, an aralkyl group, or an aryl group, Y represents a sulfur atom or an oxygen atom, n represents an integer of 0 to 2, and when n represents 2, two X's may be the same or different).

According to a second aspect of the present disclosure, there is provided an imide compound represented by Formula (1A):

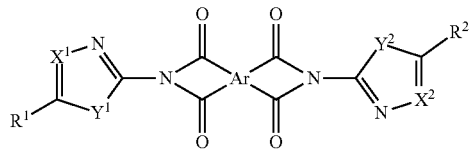

Formula (1A)

(in Formula (1A), Ar represents an aromatic group having 6 to 18 carbon atoms except for a tetravalent perylene group, $X^1$ and $X^2$ each independently represent a nitrogen atom or a substituted or unsubstituted carbon atom, and $Y^1$ and $Y^2$ each independently represent an oxygen atom, a sulfur atom, a selenium atom, or NH, and $R^1$ and $R^2$ each independently represent a hydrogen atom or a monovalent organic group).

BRIEF DESCRIPTION OF THE DRAWINGS

Exemplary embodiments of the present invention will be described in detail based on the following figures, wherein:

FIG. 6 is a graph showing a $^1$H-NMR spectrum of Exemplary Compound (1A-30);

FIG. 7 is a graph showing a $^1$H-NMR spectrum of Exemplary Compound (1A-31); and FIG. 8 is a graph showing a $^1$H-NMR spectrum of Exemplary Compound (1A-33).

DETAILED DESCRIPTION

First, the first aspect of the present disclosure will be described. These descriptions and examples are illustrative of exemplary embodiments and do not limit the scope of the invention.

—Electrophotographic Photoreceptor—

An electrophotographic photoreceptor according to the exemplary embodiment includes a conductive substrate; a photosensitive layer provided on the conductive substrate; and an undercoating layer that is provided between the conductive substrate and the photosensitive layer and includes a charge transport material containing at least one of imide compounds represented by Formula (1) or (2). In this case, in Formulas (1) and (2), moieties of $R^{10}$, $R^{11}$, $R^{20}$, and $R^{21}$ each independently represent a group represented by a thiazole group, a benzothiazole group, an oxazole group, or a benzoxazole group, which may have a substituent.

In the electrophotographic photoreceptor of the related art, since electron transportability of the undercoating layer is low, a residual potential tends to easily increase when images are formed repeatedly due to matters such as energy matching with a charge generation layer. When the residual potential is likely to increase in the undercoating layer, density unevenness or the like of an image becomes likely to occur.

On the other hand, in the electrophotographic photoreceptor according to the exemplary embodiment, an increase of the residual potential which may be caused when images are formed repeatedly is prevented by having the configuration. Detailed reasons for achieving the above effects are not always clear, but may be considered as follows.

For example, when a phthalocyanine pigment is used as a charge generation material, the imide compound represented by Formula (1) or (2) having a thiazole group, a benzothiazole group, an oxazole group, or a benzoxazole group is expected to be easily receive electrons and have sufficient electron transportability, and it is thus considered that an increase of the residual potential which may be caused when images are output repeatedly is prevented.

Hereinafter, a layer configuration of the electrophotographic photoreceptor according to the exemplary embodiment will be described.

Figure 1:
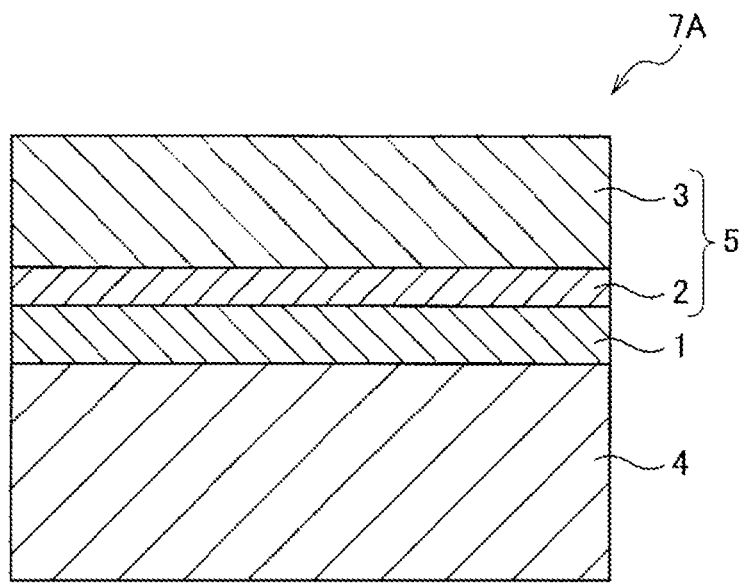
FIG. 1 is a schematic perspective diagram illustrating an example of a layer configuration of an electrophotographic photoreceptor according to the exemplary embodiment.

An electrophotographic photoreceptor 7A shown in FIG. 1 is a so-called function-separated photoreceptor (or a laminated photoreceptor), and has a structure in which an undercoating layer 1 is provided on a conductive substrate 4, and a charge generation layer 2 and a charge transport layer 3 are sequentially formed thereon. In the electrophotographic photoreceptor 7A, the photosensitive layer 5 is formed by the charge generation layer 2 and the charge transport layer 3. The electrophotographic photoreceptor according to the exemplary embodiment may be configured to include other layers, for example, a protective layer.

Hereinafter, each layer of the electrophotographic photoreceptor according to the exemplary embodiment will be described in detail. Descriptions will be given without reference numerals.

[Undercoating Layer]

Hereinafter, the undercoating layer will be described.

The undercoating layer according to the exemplary embodiment includes a charge transport material containing at least one of imide compounds represented by Formula (1) or (2). The undercoating layer according to the exemplary embodiment may contain metal oxide particles, a curing resin, and other additives.

(Charge Transport Material)

Hereinafter, the charge transport material will be described.

The charge transport material according to the exemplary embodiment contains at least one of imide compounds represented by Formula (1) or (2). The charge transport material may contain other charge transport materials.

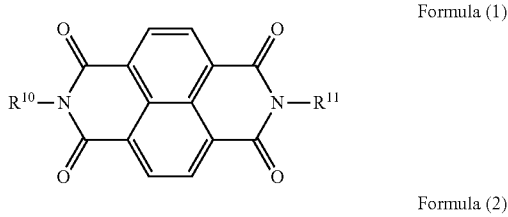

Formula (1)

Formula (2)

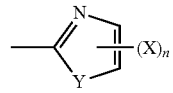

Formula (3)

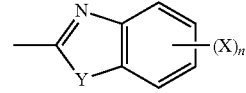

Formula (4)

In Formulas (1) and (2), $R^{10}$, $R^{11}$, $R^{20}$, or $R^{21}$ independently represents a group represented by Formula (3) or (4).

In Formulas (3) and (4), X represents a monovalent organic group having at least one of an alkyl group, an alkylene group, an ether group, an ester group, and a keto group, a halogen atom, a nitro group, an aralkyl group, or an aryl group.

In Formulas (3) and (4), Y represents a sulfur atom or an oxygen atom. n represents an integer of 0 to 2. Here, when n represents 2, two X's may be the same or different.

The monovalent organic group is a monovalent organic group formed by combining at least one of an alkyl group, an alkylene group, an ether group, an ester group, and a keto group, is preferably an alkyl group or an alkylene group each having 1 to 12 carbon atoms, and is more preferably an alkyl group or an alkylene group each having 1 to 8 carbon atoms.

Examples of the monovalent organic group include the following groups. In the following linking groups, "*" represents a moiety linked to $R^{10}$, $R^{11}$, $R^{20}$, or $R^{21}$ in Formula (1) or (2). $R^A$ represents an alkyl group, and $R^B$ represents an alkylene group. $n_1$ represents an integer of 1 or more. When $n_1$ represents an integer of 2 or more, plural $R^B$'s may be the same or different.

—$R^A$
—$R^B$—C(=O)—$R^A$
—$R^B$—O—$R^A$
—O—$R^A$
—C(=O)—$R^A$
—C(=O)—O—$R^A$
—$R^B$—C(=O)—O—$R^A$
—$R^B$—C(=O)—O—($R^B$—O)$n_1$-$R^A$.

In Formulas (3) and (4), the alkyl group represented by X corresponds to $R^A$.

In Formulas (3) and (4), the alkylene group represented by X corresponds to $R^B$.

Examples of the alkyl group represented by $R^A$ include a substituted or unsubstituted alkyl group.

Examples of the unsubstituted alkyl group represented by $R^A$ include a linear alkyl group having 1 to 12 carbon atoms (preferably 1 to 8 carbon atoms) and a branched alkyl group having 3 to 10 carbon atoms (preferably having 5 to 8 carbon atoms.

Examples of the linear alkyl group having 1 to 12 carbon atoms include a methyl group, an ethyl group, a n-propyl group, a n-butyl group, a n-pentyl group, a n-hexyl group, a n-heptyl group, a n-octyl group, a n-nonyl group, a n-decyl group, a n-undecyl group, and a n-dodecyl group.

Examples of the branched alkyl group having 3 to 10 carbon atoms include an isopropyl group, an isobutyl group, a sec-butyl group, a tert-butyl group, an isopentyl group, a neopentyl group, a tert-pentyl group, an isohexyl group, a sec-hexyl group, a tert-hexyl group, an isoheptyl group, a sec-heptyl group, a tert-heptyl group, an isooctyl group, a sec-octyl group, a tert-octyl group, an isononyl group, a sec-nonyl group, a tert-nonyl group, an isodecyl group, a sec-decyl group, and a tert-decyl group.

Among the above groups, as the unsubstituted alkyl group, lower alkyl groups such as the methyl group and the ethyl group are preferable.

As the alkylene group represented by $R^B$, groups having a structure in which one hydrogen is further removed from the alkyl group represented by $R^A$ are preferable.

Examples of the substituent in the alkyl group represented by $R^A$ include an alkoxy group having 1 to 4 carbon atoms, an unsubstituted aryl group, a phenyl group substituted with an alkyl group or alkoxy group, having 1 to 4 carbon atoms, an aralkyl group having 7 to 10 carbon atoms, a hydroxyl group, a carboxyl group, a nitro group, and a halogen atom (chlorine, iodine, bromine).

Examples of the alkoxy group of the alkoxy-substituted alkyl group include a linear or branched alkoxy group having 1 to 10 (preferably 1 to 6 and more preferably 1 to 4) carbon atoms. In addition, examples of the aryl group of the aryl-substituted alkyl group include the same groups as the unsubstituted aryl group represented by X in Formulas (3) and (4) to be described later.

Examples of the halogen atom represented by X in Formulas (3) and (4) include a fluorine atom, a chlorine atom, a bromine atom, and an iodine atom.

Examples of a substituted or unsubstituted aralkyl group represented by X in Formulas (3) and (4) include an aralkyl group having 7 to 15 (preferably 7 to 14) carbon atoms.

Specific examples of the substituted or unsubstituted aralkyl group include a benzyl group, a phenylethyl group, a vinylbenzyl group, and a hydroxyphenylmethyl group.

Examples of the aryl group represented by X in Formulas (3) and (4) include a substituted or unsubstituted aryl group.

The unsubstituted aryl group represented by X in Formulas (3) and (4) is preferably an aryl group having 6 to 30 carbon atoms, and examples thereof include a phenyl group, a biphenyl group, a 1-naphthyl group, a 2-naphthyl group, a 9-anthryl group, a 9-phenanthryl group, a 1-pyrenyl group, a 5-naphthacenyl group, a 1-indenyl group, a 2-azulenyl group, a 9-fluorenyl group, a terphenyl group, a quarterphenyl group, o-, m-, and p-tolyl groups, a xylyl group, o-, m-, and p-cumenyl groups, a mesityl group, a pentalenyl group, a binaphthalenyl group, a tanaphthalenyl group, a quaternaphthalenyl group, a heptarenyl group, a biphenylenyl group, an indacenyl group, a fluoranthenyl group, an acenaphthylenyl group, an aceanthrylenyl group, a phenalenyl group, a fluorenyl group, an anthryl group, a bianthracenyl group, a teranthracenyl group, a quater anthracenyl group, an anthraquinolyl group, a phenanthryl group, a triphenylenyl group, a pyrenyl group, a chrysenyl group, a naphthacenyl group, a preadenyl group, a picenyl group, a perylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group. Among the above groups, the phenyl group is preferable.

Examples of the substituent in the aryl group represented by X in Formulas (3) and (4) include an alkyl group, an alkoxy group, and a halogen atom (chlorine, iodine, bromine). Examples of the alkyl group of the alkyl-substituted aryl group include a linear or branched alkyl group having 1 to 10 (preferably 1 to 6 and more preferably 1 to 4) carbon atoms. Examples of the alkoxy group of the alkoxy-substituted aryl group include a linear or branched alkoxy group having 1 to 10 (preferably 1 to 6 and more preferably 1 to 4) carbon atoms.

From the viewpoint of preventing an increase of the residual potential which may be caused when images are output repeatedly, X represented in Formula (3) or (4) is preferably a monovalent organic group having at least one of an alkyl group, an alkylene group, an ether group, an ester group, and a keto group.

Exemplary compounds of the imide compounds represented by Formula (1) or (2) are shown below, but the imide compounds are not limited thereto.

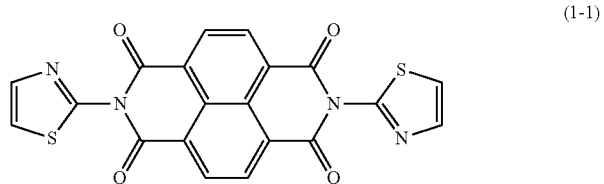

(1-1)

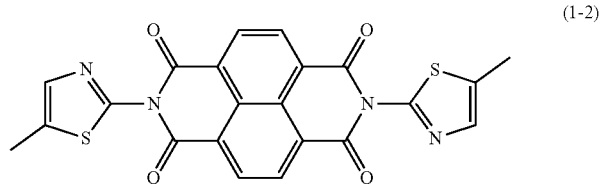

(1-2)

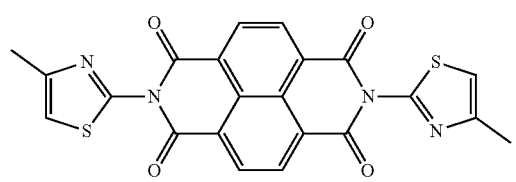

(1-3)

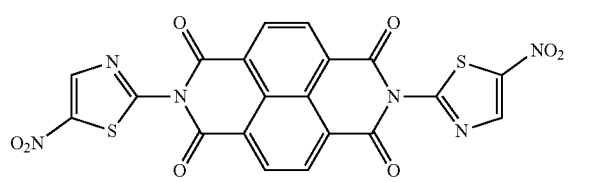

(1-4)

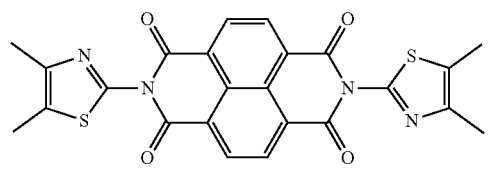

(1-5)

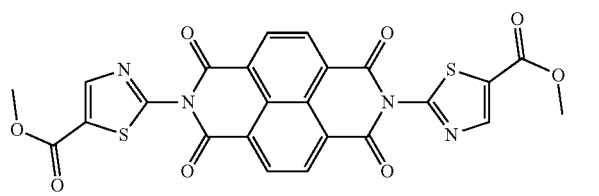

(1-6)

(1-7)
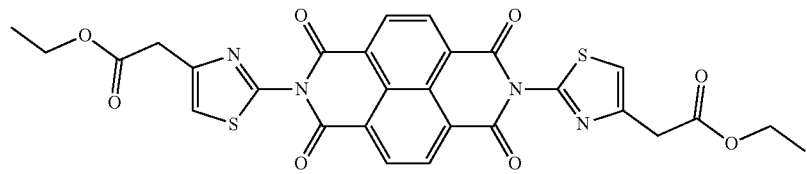
(1-8)
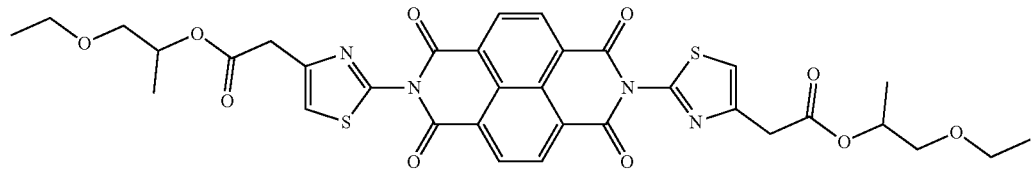
(1-9)
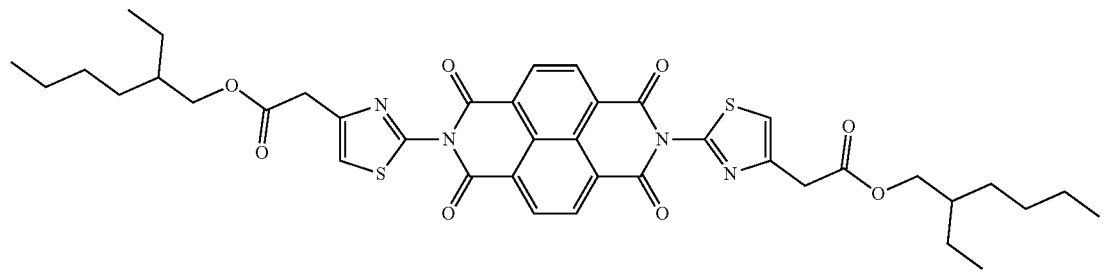
(1-10)
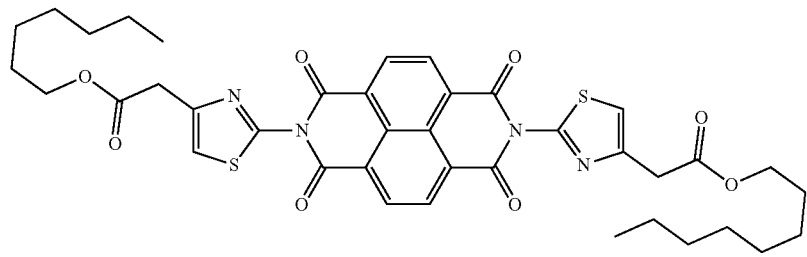
(1-11)
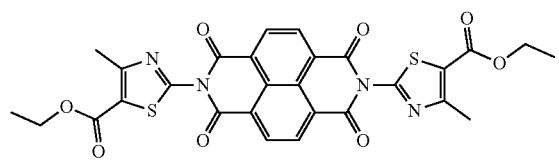
(1-12)
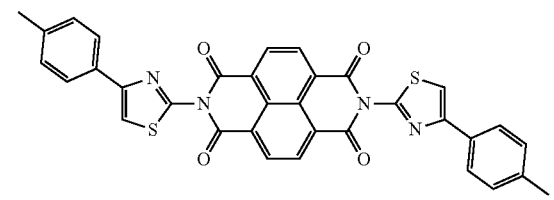
(1-13)
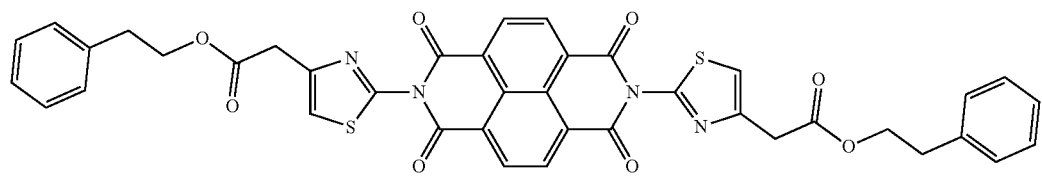
(1-14)
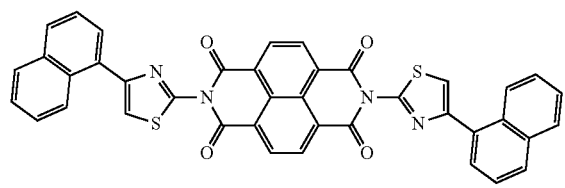
(1-15)
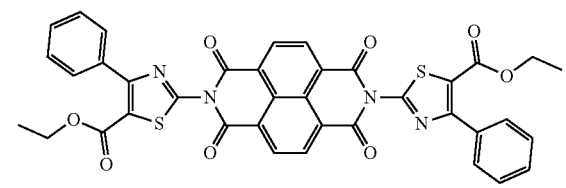

-continued
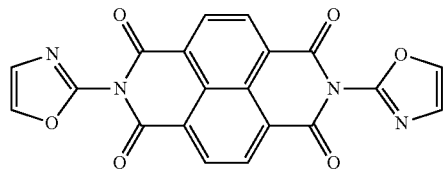
(1-16)
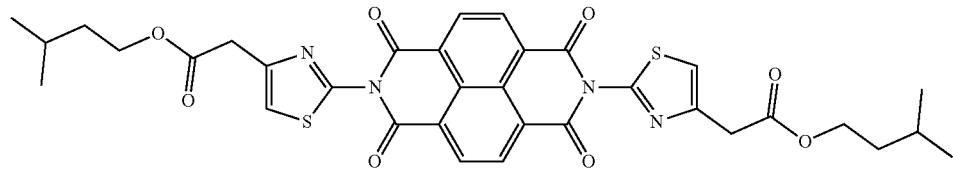
(1-17)
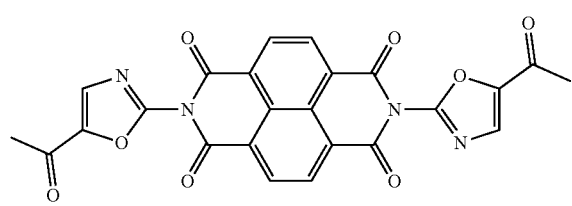
(1-18)
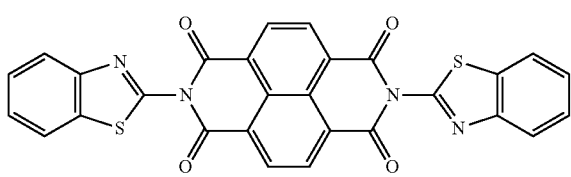
(1-19)
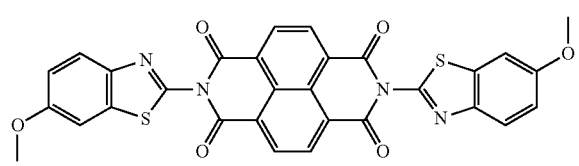
(1-20)
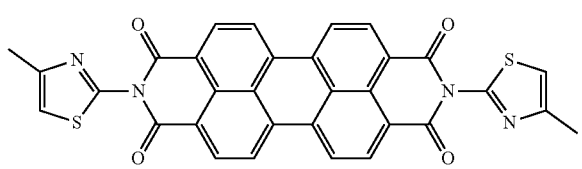
(1-21)
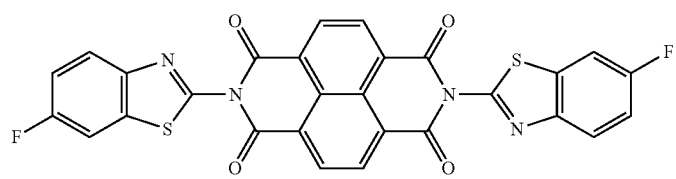
(1-22)
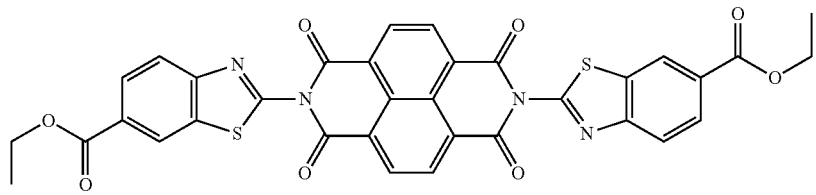
(1-23)
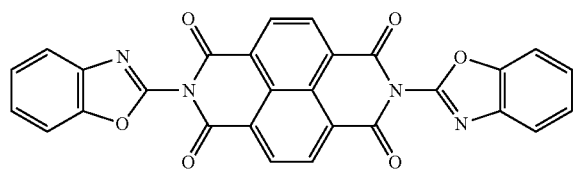
(1-24)
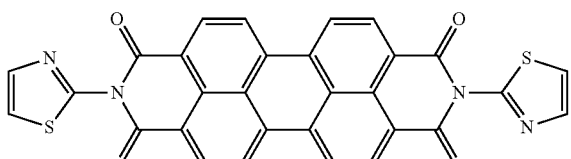
(2-1)
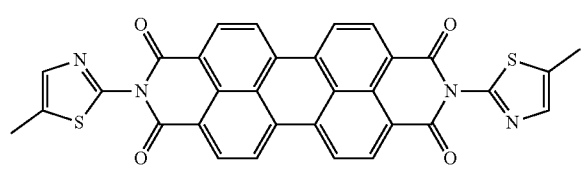
(2-2)
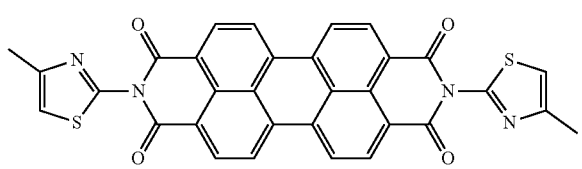
(2-3)

-continued
(2-4)
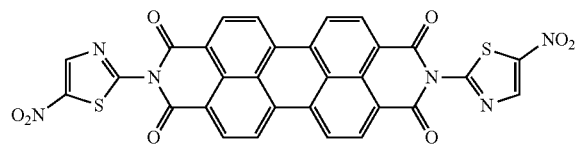
(2-5)
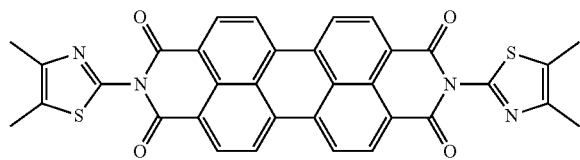
(2-6)
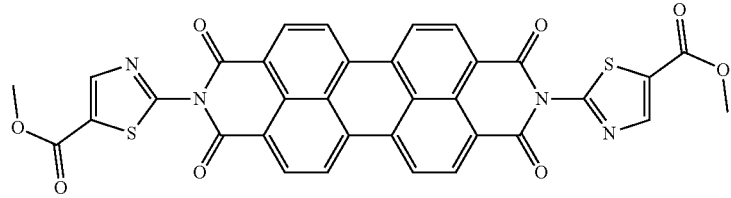
(2-7)
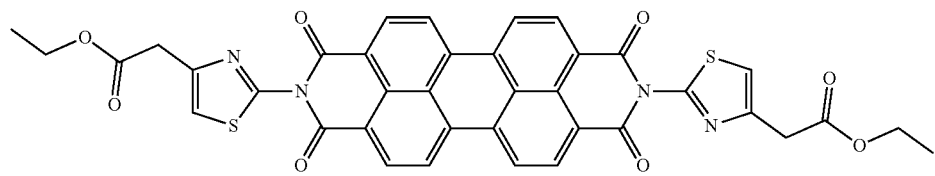
(2-8)
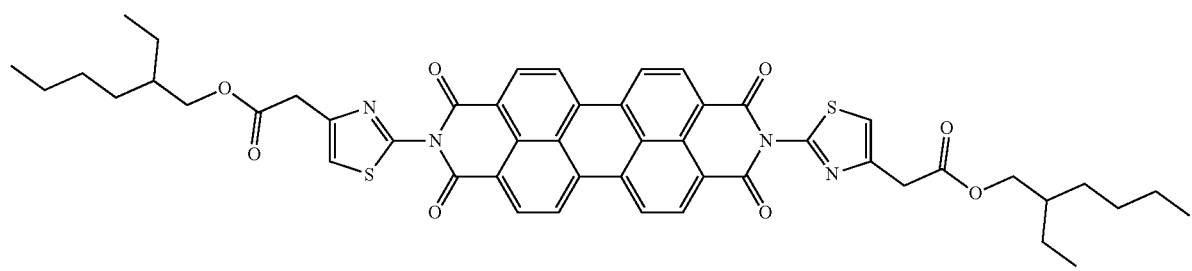
(2-9)
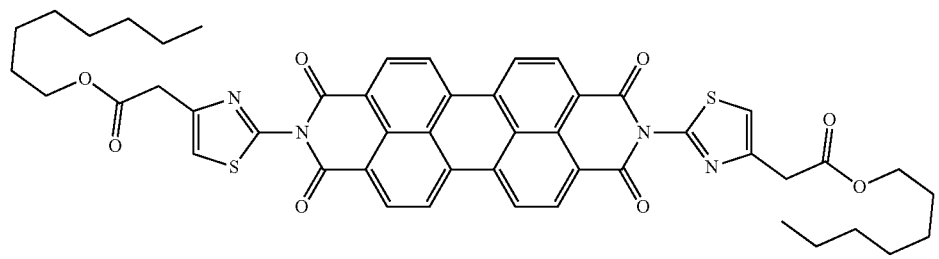
(2-10)
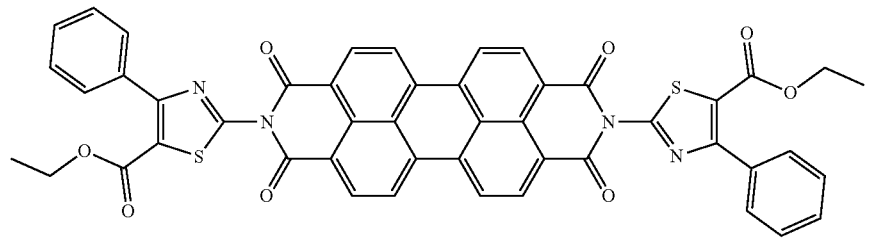
(2-11)
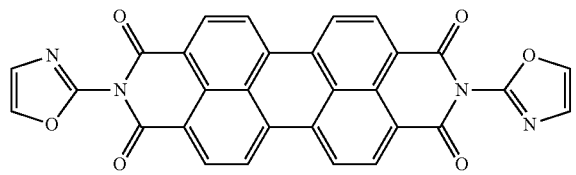
(2-12)
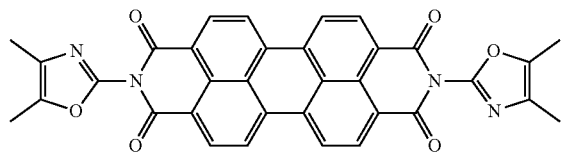

-continued

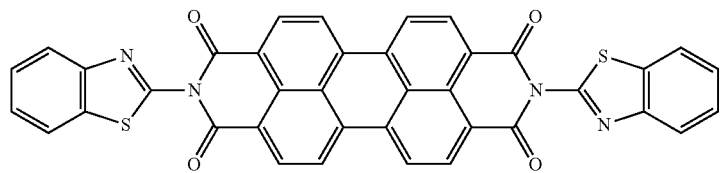
(2-13)

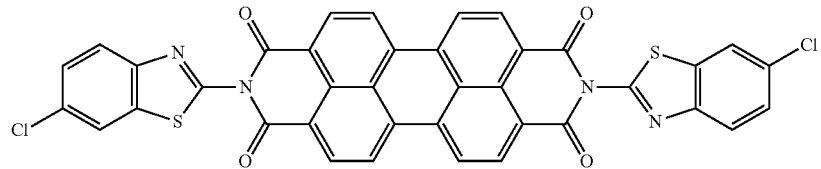
(2-14)

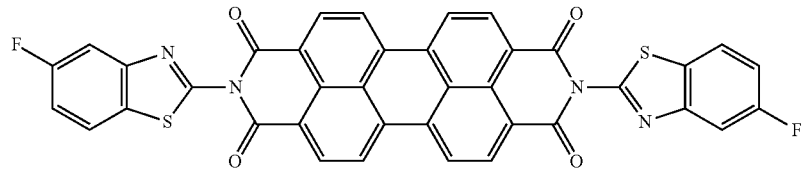
(2-15)

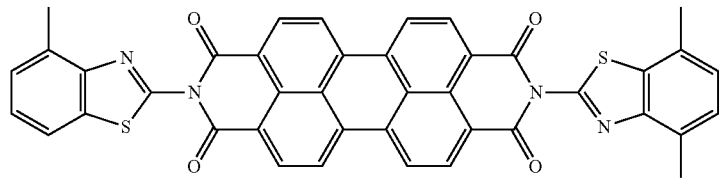
(2-16)

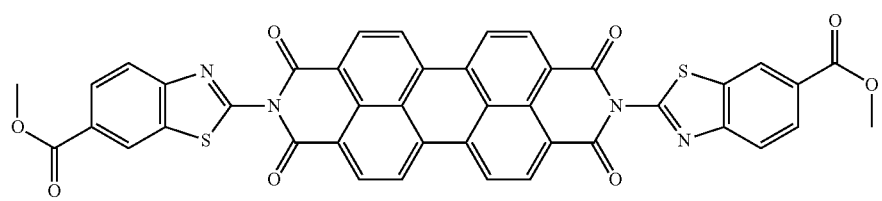
(2-17)

Other charge transport materials are not particularly limited, but examples thereof include electron transport compounds such as a quinone compound, e.g., p-benzoquinone, chloranil, bromanil, and anthraquinone; a tetracyanoquinodimethane compound; a fluorenone compound, e.g., 2,4,7-trinitrofluorenone; a xanthone compound; a benzophenone compound; a cyanovinyl compound; an ethylene compound; and a 9-dicyanomethylenefluorene compound.

In addition, hole transporting compounds such as a triarylamine compound, a benzidine compound, an arylalkane compound, an aryl-substituted ethylene compound, a stilbene compound, an anthracene compound, and a hydrazone compound are also exemplified.

These charge transport materials may be used alone or in combination of two or more thereof, though the other charge transport materials are not limited thereto.

A content of the other charge transport materials contained in the undercoating layer is not particularly limited, but is preferably from 0% by weight to 20% by weight with respect to the imide compounds represented by Formula (1) or (2), and more preferably from 0% by weight to 10% by weight.

A content of the imide compounds represented by Formula (1) or (2) in the undercoating layer is preferably from 10% by weight to 80% by weight, from the viewpoint of preventing an increase of the residual potential which may be caused when images are output repeatedly, and more preferably from 20% by weight to 70% by weight from the viewpoint of uniformity of a film at the time of coating.

(Inorganic Particles)

Hereinafter, inorganic particles will be described.

The undercoating layer according to the exemplary embodiment may further include inorganic particles besides the charge transport material containing the imide compound represented by Formula (1) or (2).

Examples of the inorganic particles include inorganic particles having a powder resistance (volume resistivity) from $1.0 \times 10^2$ ($\Omega \cdot cm$) to $1.0 \times 10^{11}$ ($\Omega \cdot cm$).

Examples of the inorganic particles having the resistance value include metal oxide particles of zinc oxide, titanium oxide, tin oxide, aluminum oxide, indium oxide, silicon oxide, magnesium oxide, barium oxide, molybdenum oxide, and the like. These may be used alone and two or more kinds thereof may be used in combination.

Among the above particles, from the viewpoint of preventing from the viewpoint of preventing an increase of the residual potential which may be caused when images are output repeatedly, at least one or more selected from the group consisting of zinc oxide, titanium oxide, and tin oxide is preferable as the metal oxide particles.

A specific surface area of the inorganic particles by a BET method is preferably, for example, 10 $m^2/g$ or more. The BET specific surface area is measured using a nitrogen substitution method. Specifically, the BET specific surface area is measured by a three point method using an SA3100 specific surface area measuring apparatus (manufactured by Beckman Coulter, Inc.).

A volume average particle diameter of the inorganic particles is preferably, for example, from 50 nm to 2,000 nm (more preferably from 60 nm to 1,000 nm).

The volume average particle diameter is measured using a laser diffraction type particle size distribution measuring apparatus (LA-700: manufactured by Horiba. Ltd.). As a measuring method, 2 g of a measurement sample is added to 50 ml of a 5% aqueous solution of a surfactant, preferably sodium alkylbenzenesulfonate, and dispersed for 2 minutes with an ultrasonic disperser (1,000 Hz) to prepare a sample, and the sample is measured. The volume average particle diameter provided per each channel obtained is accumulated from the smaller one of the volume average particle diameter, and when the accumulated volume average particle diameter reached 50% based on the sum total, the volume average particle diameter accumulated finally is taken as the volume average particle diameter.

From the viewpoint of preventing from the viewpoint of preventing an increase of the residual potential which may be caused when images are output repeatedly, a content of the inorganic particles, specifically the metal oxide particles is preferably from 10% by weight to 80% by weight, and more preferably from 20% by weight to 70% by weight with respect to the undercoating layer.

The inorganic particles may be subjected to a surface treatment. Two or more kinds of the inorganic particles, which are subjected to different surface treatments or have different particle diameters, may be mixed to be used.

Examples of the surface treatment agent include a silane coupling agent, a titanate coupling agent, an aluminum coupling agent, and a surfactant. In particular, the silane coupling agent is preferable, and a silane coupling agent having an amino group is more preferable.

Examples of the silane coupling agent having an amino group include 3-aminopropyltriethoxysilane, N-2-(aminoethyl)-3-aminopropyltrimethoxysilane, N-2-(aminoethyl)-3-amino propylmethyldimethoxysilane, and N,N-bis(2-hydroxyethyl)-3-aminopropyltriethoxysilane, but are not limited thereto.

Two or more kinds of the silane coupling agents may be mixed to be used. For example, the silane coupling agent having an amino group and the other silane coupling agent may be used in combination. Examples of the other silane coupling agent include vinyltrimethoxysilane, 3-methacryloxypropyl-tris(2-methoxyethoxy)silane, 2-(3,4-epoxycyclohexyl)ethyltrimethoxysilane, 3-glycidoxypropyltrimethoxysilane, vinyltriacetoxysilane, 3-mercaptopropyltrimethoxysilane, 3-aminopropyltriethoxysilane, N-2-(aminoethyl)-3-aminopropyltrimethoxysilane, N-2-(aminoethyl)-3-aminopropylmethyldimethoxysilane, N,N-bis(2-hydroxyethyl)-3-aminopropyltriethoxysilane, and 3-chloropropyltrimethoxysilane, but are not limited thereto.

The surface treatment method with the surface treatment agent may be any method as long as it is a known method, and either a dry method or a wet method may be used.

From the viewpoint of improving dispersibility, for example, a throughput of the surface treatment agent is preferably from 0.5% by weight to 10% by weight with respect to the inorganic particles.

Here, the undercoating layer may contain an electron accepting compound (acceptor compound) together with the inorganic particles, from the viewpoint of improving long-term stability of electric characteristics and carrier blocking property.

Examples of the electron accepting compound include electron transport substances such as: quinone compounds such as chloranil and bromoanil; a tetracyanoquinodimethane compound; fluorenone compounds such as 2,4,7-trinitrofluorenone and 2,4,5,7-tetranitro-9-fluorenone; oxadiazole compounds such as 2-(4-biphenyl)-5-(4-t-butylphenyl)-1,3,4-oxadiazole, 2,5-bis(4-naphthyl)-1,3,4-oxadiazole, and 2,5-bis(4-diethylaminophenyl)-1,3,4-oxadiazole; a xanthone compound; a thiophene compound; and diphenoquinone compounds such as 3,3',5,5'-tetra-t-butyldiphenoquinone.

In particular, as the electron accepting compound, a compound having an anthraquinone structure is preferable. As the compound having an anthraquinone structure include a hydroxyanthraquinone compound, an aminoanthraquinone compound, and an aminohydroxyanthraquinone compound are preferable, and specifically, for example, anthraquinone, alizarin, quinizarin, antharufine, purpurin, and the like are preferable.

The electron accepting compound may be contained by being dispersed in the undercoating layer together with the inorganic particles or may be contained in a state of being attached to the surfaces of the inorganic particles.

Examples of a method of attaching the electron accepting compound to the surfaces of the inorganic particles include a dry method or a wet method.

The dry method is, for example, a method in which while stirring inorganic particles with a mixer or the like having a large shear force, an electron accepting compound is dropped directly or by being dissolved in an organic solvent, and sprayed together with dry air or nitrogen gas to attach the electron accepting compound to the surfaces of the inorganic particles. When dropping or spraying the electron accepting compound, the dropping or spraying the electron accepting compound may be carried out at a temperature equal to or lower than a boiling point of the solvent. After dropping or spraying the electron accepting compound, baking may further be carried out at 100° C. or higher. Baking is not particularly limited as long as the baking is carried out at a temperature and time at which electrophotographic characteristics are obtained.

The wet method is, for example, a method in which an electron accepting compound is added while dispersing inorganic particles in a solvent by stirring, ultrasonic wave, sand mill, attritor, ball mill, or the like, and is stirred or dispersed, and then the solvent is removed to attach the electron accepting compound to the surfaces of the inorganic particles. In the solvent removal method, the solvent is removed, for example, by filtration or distillation. After removing the solvent, baking may further be carried out at 100° C. or higher. Baking is not particularly limited as long as the baking is carried out at a temperature and time at which electrophotographic characteristics are obtained. In the wet method, moisture contained in the inorganic particles may be removed before adding the electron accepting compound. Examples of this method include a method of removing the moisture while stirring and heating in a solvent, and a method of removing the moisture by azeotropic distillation with a solvent.

The attachment of the electron accepting compound may be carried out before or after the inorganic particles are subjected to the surface treatment with the surface treatment agent. Also, the attachment of the electron accepting compound and the surface treatment with the surface treatment agent may be carried out at the same time.

A content of the electron accepting compound may be, for example, from 0.01% by weight to 20% by weight, and is preferably from 0.01% by weight to 10% by weight in the inorganic particles.

(Curing Resin)

Hereinafter, the curing resin will be described.

The undercoating layer according to the exemplary embodiment may be configured to further contain the curing resin.

The undercoating layer is preferably a layer configured by a cured film (including a crosslinked film) in which the curing resin is cured.

The curing resin contained in the undercoating layer is not particularly limited as long as the curing resin does not deteriorate the electron transportability and electrification characteristic of the imide compound, and known curing resin may be used. Examples of the curing resin include thermosetting high-molecular compounds such as polyimide, a urethane resin, an epoxy resin, a phenol resin, a urea resin, a melamine resin, an unsaturated polyester resin, a diallyl phthalate resin, an alkyd resin, a polyamino bismaleimide, a furan resin, a urea resin, a phenol-formaldehyde resin, and an alkyd resin. Examples of the curing resin also include polymer compounds such as an acetal resin such as polyvinyl butyral, a polyvinyl alcohol resin, casein, a polyamide resin, a cellulose resin, gelatin, a polyester resin, a methacrylic resin, an acrylic resin, a polyvinyl chloride resin, a polyvinyl acetate resin, a vinyl chloride-vinyl acetate-maleic anhydride resin, a silicone resin, a silicone-alkyd resin, and a phenol-formaldehyde resin. Further, charge transport resin having a charge transport group and a conductive resin (such as polyaniline) may be used as the curing resin.

Among the resins, as the curing resin, at least one selected from the group consisting of a phenol resin, a melamine resin, a guanamine resin, and a urethane resin is preferable and a urethane resin is more preferable. In a case where two or more of these curing resins are used in combination, a mixing ratio thereof is set as needed.

For example, in a case where the phenol resin and the melamine resin are mixed to be used, it is preferable to perform curing using an acid catalyst. In a case where the urethane resin is used, it is preferable to perform curing using an amine catalyst or a metal catalyst. A content the catalyst used for curing is preferably from 0.01% by weight to 20% by weight and more preferably 0.1% by weight to 10% by weight, based on 100% by weight of a solid content of the undercoating layer. A curing temperature is preferably from room temperature to 200° C. and more preferably from 100° C. to 150° C.

As the phenol resin, substituted phenols containing one hydroxyl group such as resorcin, bisphenol, phenol, cresol, xylenol, paraalkylphenol, and paraphenylphenol; substituted phenols containing two hydroxyl groups such as catechol, resorcinol, and hydroquinone; bisphenols such as bisphenol A and bisphenol Z; monomethylolphenols obtained by reacting a compound having a phenol structure with formaldehyde, paraformaldehyde, or the like under an acid or alkali catalyst; dimethylol phenols; monomers of trimethylolphenols and mixtures thereof; multimers of trimethylolphenols; mixtures of monomers and polymers of trimethylolphenols; and the like are used. A molecule in which repeating structural units of a molecule is from 2 to 20 is referred to as a multimer, and a molecule in which the repeating structural units of a molecule is less than the above range is referred to as a monomer.

Examples of the melamine resin and the guanamine resin include a melamine resin and a guanamine resin, having an unmodified methylol group, an alkyl ether modified methylol group, an imino modified methylol group, a methylol group having an unmodified moiety and an imino modified moiety, and the like. Among the above resins, from the viewpoint of the stability of the coating liquid, the melamine resin and the guanamine resin, having the alkyl ether modified methylol group are preferable.

Examples of a raw material for obtaining the urethane resin include polyfunctional isocyanate and isocyanurate. In addition, blocked isocyanate having a structure in which the above-described polyfunctional isocyanate and isocyanurate are masked with a blocking agent (such as alcohol and ketone) may also be used. Among the above raw materials, from the viewpoint of the stability of the coating liquid, the raw material for obtaining the urethane resin is preferably the blocked isocyanate or isocyanurate.

Examples of the acid catalyst used for curing include: aliphatic carboxylic acids such as acetic acid, chloroacetic acid, trichloroacetic acid, trifluoroacetic acid, oxalic acid, maleic acid, malonic acid, and lactic acid; aromatic carboxylic acids such as benzoic acid, phthalic acid, terephthalic acid, and trimellitic acid; and protonic acids such as sulfonic acids such as methanesulfonic acid, dodecylsulfonic acid, benzenesulfonic acid, dodecylbenzenesulfonic acid, and naphthalenesulfonic acid. In addition, a thermally latent protonic acid catalyst in which the protonic acids are blocked with a base may be used. Among the above catalysts, from the viewpoint of storage stability, the thermally latent protonic acid catalyst is preferable as the acid catalyst used for curing.

Examples of a specific commercial product of the acid catalyst include "NACURE 2501" (toluenesulfonic acid dissociation, methanol/isopropanol solvent, from pH 6.0 to pH 7.2, and dissociation temperature of 80° C.), "NACURE 2107" (p-toluenesulfonic acid dissociation, isopropanol solvent, from pH 8.0 to pH 9.0, and dissociation temperature of 90° C.), "NACURE 2500" (p-toluenesulfonic acid dissociation, isopropanol solvent, from pH 6.0 to pH 7.0, and dissociation temperature of 65° C.), "NACURE 2530" (p-toluenesulfonic acid dissociation, methanol/isopropanol solvent, from pH 5.7 to pH 6.5, and dissociation temperature of 65° C.), "NACURE 2547" (p-toluenesulfonic acid dissociation, aqueous solution, from pH 8.0 to pH 9.0, and dissociation temperature of 107° C.), "NACURE 2558" (p-toluenesulfonic acid dissociation, ethylene/glycol solvent, from pH 3.5 to pH 4.5, and dissociation temperature of 80° C.), "NACURE XP-357" (p-toluenesulfonic acid dissociation, methanol solvent, from pH 2.0 to pH 4.0, and dissociation temperature of 65° C.), "NACURE XP-386" (p-toluenesulfonic acid dissociation, aqueous solution, from pH 6.1 to pH 6.4, and dissociation temperature of 80° C.), "NACURE XC-2211" (p-toluenesulfonic acid dissociation, from pH 7.2 to pH 8.5, and dissociation temperature of 80° C.), "NACURE 5225" (dodecylbenzene sulfonic acid dissociation, isopropanol solvent, from pH 6.0 to pH 7.0, and dissociation temperature of 120° C.), "NACURE 5414" (dodecylbenzene sulfonic acid dissociation, xylene solvent, and dissociation temperature of 120° C.), "NACURE 5528" (dodecylbenzene sulfonic acid dissociation, isopropanol solvent, from pH 7.0 to pH 8.0, and dissociation temperature of 120° C.), "NACURE 5925" (dissociation of dodecylbenzenesulfonic acid, from pH 7.0 to pH 7.5, and dissociation temperature of 130° C.), "NACURE 1323" (dinonylnaphthalenesulfonic acid dissociation, xylene solvent, from pH 6.8 to pH 7.5, and dissociation temperature of 150° C.), "NACURE 1419" (dinonylnaphthalene sulfonic acid dissociation, xylene/methyl isobutyl ketone solvent, and dissociation temperature of 150° C.), "NACURE 1557" (dinonylnaphthalenesulfonic acid dissociation, butanol/2-butoxyethanol solvent, from pH 6.5 to pH 7.5, and dissociation temperature of 150° C.), "NACURE X49-110" (dinonylnaphthalene disulfonic acid dissociation, isobutanol/isopropanol solvent, from pH 6.5 to pH 7.5, and dissociation temperature of 90° C.), "NACURE 3525" (dinonylnaphthalene disulfonic acid dissociation, isobutanol/isopropanol solvent, from pH 7.0 to pH 8.5, and dissociation temperature of 120° C.), "NACURE XP-383" (dinonylnaphthalene disulfonic acid dissociation, xylene solvent, and dissociation temperature of 120° C.), "NACURE 3327" (dinonylnaphthalene disulfonic acid dissociation, isobutanol/isopropanol solvent, from pH 6.5 to pH 7.5, and dissociation temperature of 150° C.), "NACURE 4167" (phosphate dissociation, isopropanol/isobutanol solvent, from pH 6.8 to pH 7.3, and dissociation temperature of 80° C.), "NACURE XP-297" (phosphate dissociation, water/isopropanol solvent, from pH 6.5 to pH 7.5, and dissociation temperature of 90° C.), and "NACURE 4575" (dissociation of phosphate, from pH 7.0 to pH 8.0, and dissociation temperature of 110° C.), which are manufactured by King Industries, Inc.

In the case of using a cured film obtained by curing the urethane resin, examples of the catalyst include an amine catalyst and a metal catalyst. The amine catalyst is not particularly limited, but examples thereof include 1,4-diazabicyclo(2,2,2)octane, N,N-dimethylcyclohexylamine, N-methyldicyclohexylamine, N,N,N',N'-tetramethylpropylenediamine, N-ethylmorpholine, N-methylmorpholine, N,N-dimethylethanolamine, 1,8-diaza-bicyclo[5,4,0]undecene-7(DBU), and salts thereof. The metal catalyst is not particularly limited, but examples thereof include dibutyltin laurate and stannous octoate.

The presence or absence of the solvent when preparing the coating liquid is not particularly limited. The solvent may be used or not. In a case of using the solvent for preparing the coating liquid, as the solvent, solvents such as: alcohols such as methanol, ethanol, propanol, butanol, cyclopentanol, and cyclohexanol; ketones such as acetone, methyl ethyl ketone, cyclopentanone, and cyclohexanone; ethers such as tetrahydrofuran, diethyl ether, dioxane, cyclopentyl methyl ether, and 2-methyl tetrahydrofuran; halogen such as methylene chloride and chloroform; aromatic compounds such as toluene, xylene, and ethylbenzene; and esters such as ethyl acetate and butyl acetate may be used. Among the above solvents, as the solvent, a solvent having a boiling point of 150° C. or lower is preferable, in particular, a solvent having at least one kind of hydroxyl group (such as alcohols) or an ether solvent (such as tetrahydrofuran) is more preferable. One kind of the solvents may be used alone and two or more kinds thereof may be used by being mixed.

As the curing resin, a curing agent such as a polyfunctional epoxy compound or a polyfunctional isocyanate compound may also be used.

As the polyfunctional epoxy compound, a multifunctional epoxy derivative such as a diglycidyl ether compound, a triglycidyl ether compound, or a tetraglycidyl ether compound, a haloepoxy compound, or the like may be used. Specific examples of the polyfunctional epoxy compound include glycidyl ether compounds of polyhydric alcohols such as ethylene glycol diglycidyl ether, polyethylene glycol diglycidyl ether, propylene glycol diglycidyl ether, polypropylene glycol diglycidyl ether, glyceryl diglycidyl ether, and glyceryl triglycidyl ether; glycidyl ether compounds of aromatic polyhydric phenols such as bisphenol A diglycidyl ether; and halo-epoxy compounds such as epichlorohydrin, epibromohydrin, and (3-methyl epichlorohydrin.

As the polyfunctional isocyanate compound, compounds having three or more isocyanate groups are preferable, and specific examples thereof include polyisocyanate monomers such as 1,3,6-hexamethylene triisocyanate, lysine ester triisocyanate, 1,6,11-undecane triisocyanate, 1,8-isocyanate-4-isocyanatomethyloctane, triphenylmethane triisocyanate, and tris(isocyanatephenyl) thiophosphate. Among the compounds having three or more isocyanate groups, from the viewpoints of film-forming cracking resistance and ease of handling of the crosslinked film finally obtained, modified products of derivatives, a prepolymer, or the like, obtained from the polyisocyanate monomers are more preferably used.

As examples of these, a urethane-modified product obtained by modifying a polyol with an excess of the trifunctional isocyanate compound, a burette-modified product obtained by modifying a compound having a urea bond with an isocyanate compound, and an allophanate-modified product obtained by adding an isocyanate to a urethane group are particularly preferable. In addition to these, an isocyanurate modified product, a carbodiimide modified product, and the like are used.

A total content of the curing resin according to the exemplary embodiment is preferably from 20% by weight to 50% by weight and more preferably 30% by weight to 45% by weight, in the undercoating layer.

The undercoating layer may also contain various additives.

As additives, for example, resin particles may be added. Examples of the resin particles include known materials such as silicone resin particles and crosslinked polymethylmethacrylate (PMMA) resin particles.

Hereinafter, the other properties of the undercoating layer will be described.

A film thickness of the undercoating layer is preferably from 3 μm to 50 μm and more preferably from 5 μm to 40 μm.

When the film thickness of the undercoating layer is 3 μm or more, there is tendency of preventing leakage current from occurring. On the other hand, when the film thickness of the undercoating layer is 50 μm or less, there is tendency of preventing an increase of the residual potential which may be caused when images are formed repeatedly.

The film thickness of the undercoating layer is measured using an eddy current film thickness meter CTR-1500E manufactured by Sanko Denshi Co., Ltd.

From the viewpoint of preventing lowering of electrification characteristic and an increase of the residual potential which may be caused when images are formed repeatedly, the volume resistivity of the undercoating layer is preferably from $1.0 \times 10^4$ ($\Omega \cdot m$) to $10 \times 10^{10}$ ($\Omega \cdot m$), more preferably from $1.0 \times 10^6$ ($\Omega \cdot m$) to $10 \times 10^8$ ($\Omega \cdot m$), and still more preferably from $1.0 \times 10^6$ ($\Omega \cdot m$) to $10 \times 10^7$ ($\Omega \cdot m$).

A method of preparing an undercoating layer sample to be used for measuring the volume resistivity, from an electrophotographic photoreceptor is as follows. For example, coating films such as a charge generation layer and a charge transport layer which cover the undercoating layer are removed using a solvent such as acetone, tetrahydrofuran, methanol, or ethanol, and a gold electrode is attached on the exposed undercoating layer by vacuum deposition method, a sputtering method, or the like to obtain an undercoating layer sample to be used for measuring the volume resistivity.

For measuring the volume resistivity by an alternating current impedance method, a SI 1287 electrochemical interface (manufactured by TOYO Corporation) as a power source, an SI 1260 impedance/gain phase analyzer (manufactured by TOYO Corporation) as an ammeter, and a 1296 dielectric interface (manufactured by Toyo Corporation) as a current amplifier are used.

Using an aluminum substrate in the AC impedance measurement sample as the cathode and the gold electrode as the anode, an AC voltage of 1 Vp-p is applied from the high frequency side in a frequency range from 1 MHz to 1 mHz, and the AC impedance of each sample is measured to calculate the volume resistivity by fitting the Cole-Cole plot graph obtained by the measurement to an RC parallel equivalent circuit.

The undercoating layer may have a Vickers hardness of 35 or higher.

In order to prevent a moire fringe from occurring, surface roughness (ten-point average roughness) of the undercoating layer may be adjusted from 1/(4n) (n is a refractive index of an upper layer) of the exposure laser wavelength λ to ½ thereof.

In order to adjust the surface roughness, resin particles or the like may be added to the undercoating layer. Examples of the resin particles include silicone resin particles and crosslinked polymethylmethacrylate resin particles. Further, in order to adjust the surface roughness, the surface of the undercoating layer may be polished. Examples of a polishing method include buffing, sandblasting treatment, wet honing, and grinding treatment.

Formation of the undercoating layer is not particularly limited and a known forming method is used. For example, a coating film of an undercoating layer-forming coating liquid obtained by adding the above components to a solvent is formed, and the coating film is dried to form the undercoating layer by heating as needed.

Examples of the solvent for preparing the undercoating layer-forming coating liquid include known organic solvents such as alcohol solvent, aromatic hydrocarbon solvent, halogenated hydrocarbon solvent, ketone solvent, ketone alcohol solvent, ether solvent, and ester solvent.

Specific examples of these solvents include usual organic solvents such as methanol, ethanol, n-propanol, iso-propanol, n-butanol, benzyl alcohol, methyl cellosolve, ethyl cellosolve, acetone, methyl ethyl ketone, cyclohexanone, methyl acetate, ethyl acetate, n-butyl acetate, dioxane, tetrahydrofuran, methylene chloride, chloroform, chlorobenzene, and toluene.

As a method of dispersing the charge transport material containing at least one of imide compounds represented by Formula (1) or (2) in the undercoating layer, from the viewpoint of improving film formability of the undercoating layer, known methods such as a roll mill, a ball mill, a vibration ball mill, an attritor, a sand mill, a colloid mill, a paint shaker, or the like may be used. Even in a case where the undercoating layer further contains inorganic particles, the dispersion may be prepared by the same method.

Examples of a method for applying the undercoating layer-forming coating liquid onto the conductive substrate include normal methods such as a blade coating method, a wire bar coating method, a spray coating method, a dipping coating method, a bead coating method, an air knife coating method, and a curtain coating method.

[Conductive Substrate]

Examples of the conductive substrate include a metal plate including a metal (such as aluminum, copper, zinc, chromium, nickel, molybdenum, vanadium, indium, gold, and platinum) or an alloy (such as stainless steel), a metal drum, and a metal belt. In addition, examples of the conductive substrate also include paper, a resin film, and a belt which are obtained by applying, vapor-depositing, or laminating a conductive compound (for example, a conductive polymer, indium oxide, or the like), metal (for example, aluminum, palladium, gold, or the like), or an alloy. Here, "conductive" means that the volume resistivity is less than 1013 (Ω·cm).

In a case where the electrophotographic photoreceptor is used in a laser printer, the surface of the conductive substrate preferably roughened to have a center line average roughness Ra from 0.04 μm to 0.5 μm in order to prevent interference fringes generated when emitting laser light. In a case of using non-interference light as a light source, although roughening for prevention of interference fringes is not particularly necessary, since the roughening prevents defects from occurring due to irregularities on the surface of the conductive substrate, it is suitable for longer life.

Examples of a surface-roughening method include wet honing performed by suspending an abrasive in water and blowing suspension on the conductive substrate, centerless grinding performed by pressing the conductive substrate against a rotating grindstone and performing continuous grinding processing, and anodic oxidation.

Examples of the surface-roughening method also include a method in which a conductive or semi-conductive powder is dispersed in a resin without roughening the surface of the conductive substrate to form a layer on the surface of the conductive substrate and surface-roughening is performed by particles dispersed in the layer.

The surface roughening treatment by anodic oxidation is to form an oxide film on the surface of the conductive substrate by anodizing in an electrolyte solution using a conductive substrate made of metal (for example, aluminum) as an anode. Examples of the electrolyte solution include a sulfuric acid solution and an oxalic acid solution. However, a porous anodic oxide film formed by the anodic oxidation is chemically active in the state as it is, is likely to be stained, and has a large change in resistance depending on the environment. Therefore, the porous anodic oxide film is preferably subjected to a sealing treatment that fine pores of the oxide film are blocked by volume expansion due to hydration reaction in pressurized water vapor or boiling water (a metal salt such as nickel may be added) to be changed to a more stable hydrated oxide.

A thickness of the anodic oxide film is preferably, for example, from 0.3 μm to 15 μm. When the film thickness is within the above range, there is tendency that barrier properties against injection is exhibited, and there is tendency that residual potential is prevented from increasing due to repeated use.

The conductive substrate may also be subjected to a treatment with an acidic treatment solution or a boehmite treatment.

The treatment with the acidic treatment solution is carried out, for example, as follows. First, an acidic treatment liquid containing phosphoric acid, chromic acid, and hydrofluoric acid is prepared. A mixing ratio of the phosphoric acid, the chromic acid, and the hydrofluoric acid in the acidic treatment solution is, for example, from 10% by weight to 11% by weight of phosphoric acid, 3% by weight to and 5% by weight of chromic acid, and 0.5% by weight to 2% by weight, and a concentration of these whole acids may be from 13.5% by weight to 18% by weight. A treatment temperature is preferably, for example, from 42° C. to 48° C. A film thickness of the film to be coated is preferably from 0.3 µm to 15 µm.

The boehmite treatment is carried out by, for example, dipping the conductive substrate in deionized water from 90° C. to 100° C. for 5 minutes to 60 minutes, or making the conductive substrate in contact with heated steam from 90° C. to 120° C. for 5 minutes to 60 minutes. A film thickness of the film to be coated is preferably from 0.1 µm to 5 µm. The anodic oxidation may be further performed using an electrolyte solution having low film solubility such as adipic acid, boric acid, borate, phosphate, phthalate, maleate, benzoate, tartrate, and citrate.

[Photosensitive Layer]
(Charge Generation Layer)

The charge generation layer is, for example, a layer containing a charge generation material and a binder resin. Further, the charge generation layer may be a deposition layer of a charge generation material. The deposition layer of the charge generation material is suitable for a case of using an incoherent light source such as a light emitting diode (LED) or an organic electro-luminescence (EL) image array.

Examples of the charge generation material include azo pigments such as bisazo and trisazo; a condensed ring aromatic pigment such as dibromoanthanthrone; a perylene pigment; a pyrrolopyrrole pigment; a phthalocyanine pigment; zinc oxide; and trigonal selenium.

Among these materials, in order to cope with laser exposure in the near infrared region, it is preferable to use a metal phthalocyanine pigment or a metal-free phthalocyanine pigment, as the charge generation material. Specifically, for example, hydroxygallium phthalocyanine; chlorogallium phthalocyanine; dichlorotin phthalocyanine; and titanyl phthalocyanine are more preferable.

On the other hand, in order to cope with laser exposure in the near ultraviolet region, as the charge generation material, a condensed aromatic pigment such as dibromoanthanthrone; a thioindigo pigment; a porphyrazine compound; zinc oxide; trigonal selenium; a bisazo pigment; and the like are preferable.

Also in a case of using an incoherent light source having an emission center wavelength from 450 nm to 780 nm, such as an LED or an organic EL image array, the above charge generation material may be used. However, when a thin film of 20 µm or less is used as the photosensitive layer from the viewpoint of resolution, the electric field intensity in the photosensitive layer increases, and charge reduction due to charge injection from the substrate is caused, so that image defect referred to as a so-called black spot tend to occur. The tendency is remarkable when using a charge generation material which is likely to cause dark current in a p-type semiconductor such as trigonal selenium or a phthalocyanine pigment.

On the contrary, when using a n-type semiconductor such as a condensed ring aromatic pigment, a perylene pigment, and an azo pigment, as the charge generation material, it is difficult to generate a dark current and, even in a thin film, the image defect called a black spot is prevented.

n-Type is determined depending on a polarity of flowing photocurrent by using a normally used time-of-flight method, and a type in which the photocurrent is easy to flow using electrons rather than holes as carriers is determined as the n-type.

The binder resin used for the charge generation layer is selected from a wide range of insulating resins. In addition, the binder resin may be selected from organic photoconductive polymers such as poly-N-vinylcarbazole, polyvinylanthracene, polyvinylpyrene, and polysilane.

Examples of the binder resin include a polyvinyl butyral resin, a polyarylate resin (such as polycondensate of bisphenols and aromatic dicarboxylic acid), a polycarbonate resin, a polyester resin, a phenoxy resin, a vinyl chloride-vinyl acetate copolymer, a polyamide resin, an acrylic resin, a polyacrylamide resin, a polyvinyl pyridine resin, a cellulose resin, a urethane resin, an epoxy resin, casein, a polyvinyl alcohol resin, and a polyvinyl pyrrolidone resin. Here, "insulating property" means that the volume resistivity is $10^{13}$ Ωcm or higher.

One kind of these binder resins is used alone or two or more kinds thereof are used by being mixed.

A mixing ratio of the charge generation material and the binder resin is preferably from 10:1 to 1:10 in terms of weight ratio.

The charge generation layer may also contain other known additives.

Formation of the charge generation layer is not particularly limited and a known forming method is used. For example, a coating film of a charge generation layer-forming coating liquid obtained by adding the above components to a solvent is formed, and the coating film is dried to form the charge generation layer by heating as needed. The formation of the charge generation layer may be carried out by vapor deposition of the charge generation material. Formation of the charge generation layer by the vapor deposition is particularly suitable for a case of using a condensed ring aromatic pigment or a perylene pigment as the charge generation material.

Examples of a solvent for preparing the charge generation layer-forming coating liquid include methanol, ethanol, n-propanol, n-butanol, benzyl alcohol, methyl cellosolve, ethyl cellosolve, acetone, methyl ethyl ketone, cyclohexanone, methyl acetate, n-butyl acetate, dioxane, tetrahydrofuran, methylene chloride, chloroform, chlorobenzene, and toluene. One kind of the solvents is used alone and two or more kinds thereof are used by being mixed.

In a method for dispersing particles (for example, charge generation material) in the charge generation layer-forming coating liquid, for example, a media dispersing machine such as a ball mill, a vibration ball mill, an attritor, a sand mill, and a horizontal sand mill or a medialess dispersing machine such as a stirrer, an ultrasonic dispersing machine, a roll mill, and a high-pressure homogenizer is used. Examples of the high-pressure homogenizer include a collision type in which dispersing is performed by a liquid-liquid collision or a liquid-wall collision in a high pressure state, or a penetration type in which dispersing is performed by penetrating a fine flow path in a high pressure state.

When dispersing is performed, it is effective to set the average particle diameter of the charge generation material in the charge generation layer-forming coating liquid to 0.5 µm or less, preferably 0.3 µm or less, and more preferably 0.15 µm or less.

Examples of a method for coating the undercoating layer (or an intermediate layer) with the charge generation layer-forming coating liquid include normal methods such as a blade coating method, a wire bar coating method, a spray coating method, a dipping coating method, a bead coating method, an air knife coating method, and a curtain coating method.

A film thickness of the charge generation layer is set preferably from 0.1 µm to 5.0 µm, and more preferably from 0.2 µm to 2.0 µm.

(Charge Transport Layer)

The charge transport layer is, for example, a layer containing a charge transport material and the binder resin. The charge transport layer may be a layer containing a polymer charge transport material.

Examples of the charge transport material include electron transport compounds such as: quinone compounds such as p-benzoquinone, chloranil, bromanil, and anthraquinone; a tetracyanoquinodimethane compound; a fluorenone compound such as 2,4,7-trinitrofluorenone; a xanthone compound; a benzophenone compound; a cyanovinyl compound; and an ethylene compound. Examples of the charge transport material also include hole transporting compounds such as a triarylamine compound, a benzidine compound, an arylalkane compound, an aryl-substituted ethylene compound, a stilbene compound, an anthracene compound, and a hydrazone compound. These charge transport materials may be used alone or in combination of two or more thereof, but are not limited thereto.

As the charge transport material, from the viewpoint of charge mobility, a triarylamine derivative represented by the following Formula (a-1) and a benzidine derivative represented by the following Formula (a-2) are preferable.

In Formula (a-1), $Ar^{T1}$, $Ar^{T2}$, and $Ar^{T3}$ each independently represent a substituted or unsubstituted aryl group, —$C_6H_4$—$C(R^{T4})$=$C(R^{T5})(R^{T6})$, or —$C_6H_4$—CH=CH—CH=$C(R^{T7})(R^{T8})$. $R^{T4}$, $R^{T5}$, $R^{T6}$, $R^{T7}$, and $R^{T8}$ each independently represent a hydrogen atom, a substituted or unsubstituted alkyl group, or a substituted or unsubstituted aryl group.

Examples of the substituent of each of the above groups include a halogen atom, an alkyl group having 1 to 5 carbon atoms, and an alkoxy group having 1 to 5 carbon atoms. Examples of the substituent of each of the above groups also include a substituted amino group substituted with an alkyl group having 1 to 3 carbon atoms.

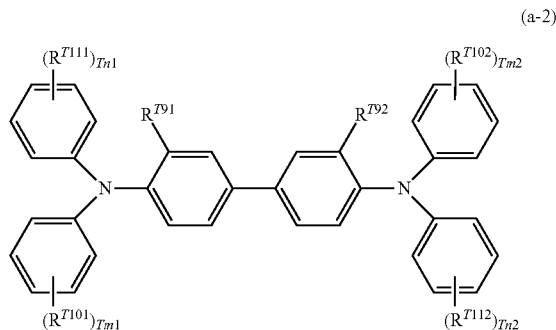

In Formula (a-2), $R^{T91}$ and $R^{T92}$ each independently represent a hydrogen atom, a halogen atom, an alkyl group having 1 to 5 carbon atoms, or an alkoxy group having 1 to 5 carbon atoms. $R^{T101}$, $R^{T12}$, $R^{T111}$, and $R^{T112}$ each independently represent a halogen atom, an alkyl group having 1 to 5 carbon atoms, an alkoxy group having 1 to 5 carbon atoms, an amino group having 1 or 2 carbon atoms substituted with an alkyl group, a substituted or unsubstituted aryl group, —$C(R^{T12})$=$C(R^{T13})(R^{T14})$, or —CH=CH—CH=$C(R^{T15})(R^{T16})$. $R^{T12}$, $R^{T13}$, $R^{T14}$, $R^{T15}$, and $R^{T16}$ each independently represent a hydrogen atom, a substituted or unsubstituted alkyl group, or a substituted or unsubstituted aryl group. Tm1, Tm2, Tn1, and Tn2 each independently represent an integer of 0 to 2.

Examples of the substituent of each of the above groups include a halogen atom, an alkyl group having 1 to 5 carbon atoms, and an alkoxy group having 1 to 5 carbon atoms. Examples of the substituent of each of the above groups also include a substituted amino group substituted with an alkyl group having 1 to 3 carbon atoms.

Among the triarylamine derivative represented by Formula (a-1) and the benzidine derivative represented by Formula (a-2), from the viewpoint of charge mobility, a triarylamine derivative having "—$C_6H_4$—CH=CH—CH=$C(R^{T7})(R^{T8})$" and a benzidine derivative having "—CH=CH—CH=$C(R^{T15})(R^{T16})$" are particularly preferable.

As the polymer charge transport material, known materials having charge transporting ability, such as poly-N-vinylcarbazole and polysilane are used. In particular, a polyester polymer charge transport material is particularly preferable. The polymer charge transport material may be used alone or may be used in combination with the binder resin.

Examples of the binder resin used for the charge transport layer include a polycarbonate resin, a polyester resin, a polyarylate resin, a methacrylic resin, an acrylic resin, a polyvinyl chloride resin, a polyvinylidene chloride resin, a polystyrene resin, a polyvinyl acetate resin, a styrene-butadiene copolymer, a vinylidene chloride-acrylonitrile copolymer, a vinyl chloride-vinyl acetate copolymer, a vinyl chloride-vinyl acetate-maleic anhydride copolymer, a silicone resin, silicone alkyd resin, a phenol-formaldehyde resin, a styrene-alkyd resin, poly-N-vinylcarbazole, and polysilane. Among these, the polycarbonate resin or the polyarylate resin is appropriate as the binder resin. One kind of these binder resins is used alone or two or more kinds thereof are used.

A mixing ratio of the charge transport material and the binder resin is preferably from 10:1 to 1:5 in terms of weight ratio.

The charge transport layer may also contain other known additives.

Formation of the charge transport layer is not particularly limited and a known forming method is used. For example, a coating film of a charge transport layer-forming coating liquid obtained by adding the above components to a solvent is formed, and the coating film is dried to form charge transport layer by heating as needed.

Examples of a solvent for preparing the charge transport layer-forming coating liquid include usual organic solvents such as aromatic hydrocarbons such as benzene, toluene, xylene, and chlorobenzene; ketones such as acetone and 2-butanone; halogenated aliphatic hydrocarbons such as methylene chloride, chloroform, and ethylene chloride; and cyclic or linear ethers such as tetrahydrofuran and ethyl ether.

One kind of the solvents is used alone and two or more kinds thereof are used by being mixed.

Examples of an applying method used when applying the charge transport layer-forming coating liquid onto the charge generation layer include normal methods such as a blade coating method, a wire bar coating method, a spray coating method, a dipping coating method, a bead coating method, an air knife coating method, and a curtain coating method.

A film thickness of the charge transport layer is set preferably from 5 μm to 50 μm, and more preferably from 10 μm to 30 μm.

(Protective Layer)

The protective layer is provided on the photosensitive layer as needed. The protective layer is provided, for example, to prevent the photosensitive layer from chemically changing at the time of charging and to further improve the mechanical strength of the photosensitive layer.

Therefore, a layer configured by a cured film (crosslinked film) may be applied to the protective layer. Examples of the layer include a layer shown in the following 1) or 2).

1) A layer configured by a cured film of a composition containing a reactive group-containing charge transport material having a reactive group and a charge transporting skeleton in the same molecule (that is, a layer containing a polymer or crosslinked member of the reactive group-containing charge transport material)

2) A layer configured by a cured film of a composition containing a non-reactive charge transport material and a reactive group-containing non-charge transport material having a reactive group without having a charge transporting skeleton (that is, a layer containing a non-reactive charge transport material and a polymer or a crosslinked member of the reactive group-containing non-charge transport material)

Examples of the reactive group of the reactive group-containing charge transport material include known reactive groups such as a chain polymerizable group, an epoxy group, —OH, —OR (where R represents an alkyl group), —NH$_2$, —SH, —COOH, and —SiR$^{Q1}_{3-Qn}$(OR$^{Q2}$)$_{Qn}$ (where R$^{Q1}$ represents a hydrogen atom, an alkyl group, or a substituted or unsubstituted aryl group, R$^{Q2}$ represents a hydrogen atom, an alkyl group, or a trialkylsilyl group, and Qn represents an integer of 1 to 3).

The chain polymerizable group is not particularly limited as long as it is a functional group capable of radical polymerization, and is, for example, a functional group having a group containing at least a carbon double bond. Specific examples thereof include a group containing at least one selected from a vinyl group, a vinyl ether group, a vinyl thioether group, a styryl group (vinyl phenyl group), an acryloyl group, a methacryloyl group, and derivatives thereof. Among these, from the viewpoint of excellent reactivity, as the chain polymerizable group, a group containing at least one selected from the vinyl group, the styryl group (vinylphenyl group), the acryloyl group, the methacryloyl group, and derivatives thereof is preferable.

The charge transporting skeleton of the reactive group-containing charge transport material is not particularly limited as long as it is a known structure in an electrophotographic photoreceptor, and examples thereof include skeleton derived from a nitrogen-containing hole transport compound such as a triarylamine compound, a benzidine compound, and a hydrazone compound, in which the skeleton has a structure conjugated with a nitrogen atom. Among these, a triarylamine skeleton is preferable.

The reactive group-containing charge transport material having a reactive group and a charge transporting skeleton, the non-reactive charge transport material, and the reactive group-containing non-charge transport material may be selected from known materials.

The protective layer may also contain other known additives.

Formation of the protective layer is not particularly limited and a known forming method is used. For example, a coating film of a protective layer-forming coating liquid obtained by adding the above components to a solvent is formed, and the coating film is dried to form the protective layer by heating as needed.

Examples of the solvent for preparing the protective layer-forming coating liquid include aromatic solvents such as toluene and xylene; ketone solvents such as methyl ethyl ketone, methyl isobutyl ketone, and cyclohexanone; ester solvents such as ethyl acetate and butyl acetate; ether solvents such as tetrahydrofuran and dioxane; cellosolve solvents such as ethylene glycol monomethyl ether; and alcohol solvents such as isopropyl alcohol and butanol. One kind of the solvents is used alone and two or more kinds thereof are used by being mixed.

The protective layer-forming coating liquid may be a solventless coating liquid.

Examples of a method of applying the protective layer-forming coating liquid onto hotosensitive layer (for example, charge transport layer) include normal methods such as a dipping coating method, an extrusion coating method, a wire bar coating method, a spray coating method, a blade coating method, a knife coating method, and a curtain coating method.

A film thickness of the protective layer is set, for example, preferably from 1 μm to 20 μm, and more preferably from 2 μm to 10 μm.

[Singlelayer Type Photosensitive Layer]

The singlelayer type photosensitive layer (charge generation/transport layer) is, for example, a layer containing a charge generation material and a charge transport material, and further contains a binder resin and other known additives, as needed. These materials are the same as those described for the charge generation layer and the charge transport layer.

Then, a content of the charge generation material in the singlelayer type photosensitive layer may be from 10% by weight to 85% by weight, and is preferably from 20% by weight to 50% by weight, based on the total solid content. In addition, a content of the charge transport material in the singlelayer type photosensitive layer may be from 5% by weight to 50% by weight, based on the total solid content.

The method of forming the singlelayer type photosensitive layer is the same as the method of forming the charge generation layer and the charge transport layer.

A film thickness of the singlelayer type photosensitive layer may be from 5 μm to 50 μm, and is preferably from 10 μm to 40 μm.

—Image Forming Apparatus and Process Cartridge—

An image forming apparatus according to the exemplary embodiment includes: an electrophotographic photoreceptor; a charging unit that charges a surface of the electrophotographic photoreceptor; an electrostatic latent image forming unit that forms an electrostatic latent image on the charged surface of the electrophotographic photoreceptor; a developing unit that develops the electrostatic latent image formed on the surface of the electrophotographic photoreceptor with a developer including toner to form a toner image; and a transfer unit that transfers the toner image onto a surface of a recording medium. As the electrophotographic photoreceptor, the electrophotographic photoreceptor according to the exemplary embodiment is adopted.

As the image forming apparatus according to the exemplary embodiment, known image forming apparatuses are adopted. Examples thereof include an apparatus including fixing unit that fixes a transferred toner image to a surface of a recording medium; a direct transfer type apparatus that directly transfers a toner image formed on a surface of an electrophotographic photoreceptor to a recording medium; an intermediate transfer type apparatus that primarily transfers a toner image formed on a surface of an electrophotographic photoreceptor to a surface of an intermediate transfer member and secondarily transfers the toner image transferred to the surface of the intermediate transfer member onto a surface of a recording medium; an apparatus including a cleaning unit that cleans a surface of the electrophotographic photoreceptor after the transfer of the toner image and before charging; an apparatus including an erasing unit that irradiates a surface of the electrophotographic photoreceptor after the transfer of a toner image and before charging, with antistatic electricity to erase electricity; and an apparatus including an electrophotographic photoreceptor heating unit that raise a temperature of an electrophotographic photoreceptor and reduces a relative temperature.

In a case of the intermediate transfer type apparatus, the transfer unit adopts, for example, a configuration including an intermediate transfer member in which a toner image is transferred on a surface thereof, a primary transfer unit that primarily transfers the toner image formed on the surface of the electrophotographic photoreceptor to a surface of the intermediate transfer member, and a secondary transfer unit that secondary transfers the toner image transferred to the surface of the intermediate transfer member to a surface of a recording medium.

The image forming apparatus according to the exemplary embodiment may be any of a dry developing type image forming apparatus or a wet developing type (a developing type using a liquid developer) image forming apparatus.

In the image forming apparatus according to the exemplary embodiment, for example, a portion having an electrophotographic photoreceptor may have a cartridge structure (process cartridge) to be attached to and detached from the image forming apparatus. As the process cartridge, for example, a process cartridge including the electrophotographic photoreceptor according to the exemplary embodiment is suitably used. In the process cartridge may further include, for example, at least one selected from the group consisting of a charging unit, an electrostatic latent image forming unit, a developing unit, and a transfer unit, in addition to the electrophotographic photoreceptor.

Hereinafter, an example of the image forming apparatus according to the exemplary embodiment will be shown, but the image forming apparatus is not limited thereto. A main part shown in the figure will be described, and descriptions for the other parts will be omitted.

Figure 2:
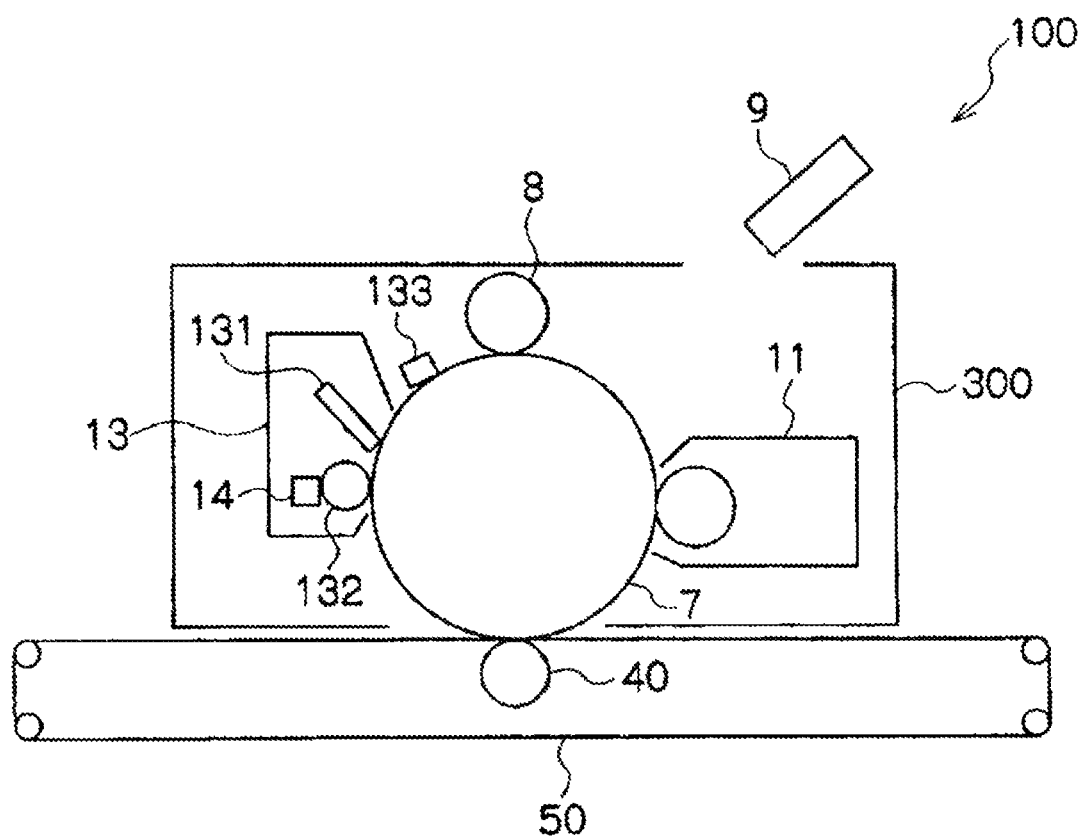
FIG. 2 is a schematic sectional diagram of an example of an image forming apparatus according to the exemplary embodiment.

FIG. 2 is a configuration diagram illustrating an example of the image forming apparatus according to the exemplary embodiment.

As shown in FIG. 2, the image forming apparatus 100 according to the exemplary embodiment includes a process cartridge 300 having an electrophotographic photoreceptor 7, an exposure device 9 (an example of an electrostatic latent image forming unit), a transfer device 40 (primary transfer device), and an intermediate transfer member 50. In the image forming apparatus 100, the exposure device 9 is disposed at a position at which the electrophotographic photoreceptor 7 may be exposed from an opening of the process cartridge 300, the transfer device 40 is disposed at a position facing the electrophotographic photoreceptor 7 via the intermediate transfer member 50, and the intermediate transfer member 50 is disposed so that a part thereof contacts with the electrophotographic photoreceptor 7. Although not shown, the image forming apparatus 100 further includes a secondary transfer device that transfers the toner image transferred to the intermediate transfer member 50 to a recording medium (for example, paper). The intermediate transfer member 50, the transfer device 40 (primary transfer device), and the secondary transfer device (not shown) correspond to examples of the transfer unit.

The process cartridge 300 in FIG. 2 includes the electrophotographic photoreceptor 7, a charging device 8 (an example of the charging unit), a developing device 11 (an example of the developing unit), and a cleaning device 13 (an example of the cleaning unit), which are in a housing and are integrally supported. The cleaning device 13 has a cleaning blade (an example of a cleaning member) 131. The cleaning blade 131 is disposed so as to contact with a surface of the electrophotographic photoreceptor 7. The cleaning member may be a conductive or insulating fibrous member, instead of an aspect of the cleaning blade 131. The conductive or insulating fibrous member may be used alone or in combination with the cleaning blade 131.

In FIG. 2, as the image forming apparatus, an example of including a fibrous member 132 (roll-shaped) that supplies a lubricant 14 to the surface of the electrophotographic photoreceptor 7 and a fibrous member 133 (flat brush shaped) that assists cleaning is shown, but these are disposed as needed.

Hereinafter, a configuration of the image forming apparatus according to the exemplary embodiment will be described.

—Charging Device—

As the charging device 8, for example, a contact type charging member using a conductive or semiconductive charging roller, a charging brush, a charging film, a charging rubber blade, a charging tube, or the like is used. In addition, a non-contact type roller charger, a charger known as it is such as a scorotron charger or a corotron charger using corona discharge, or the like is also used.

—Exposure Device—

Examples of the exposure device 9 include an optical system device the exposes the surface of the electrophotographic photoreceptor 7 to light such as semiconductor laser light, LED light, liquid crystal shutter light according to an image data. A wavelength of the light source is within a spectral sensitivity range of the electrophotographic photoreceptor. As a wavelength of the semiconductor laser, near infrared having an emission wavelength near 780 nm is mainly used. However, the wavelength is not limited thereto, and an emission wavelength laser of 600 nm band or a laser having an emission wavelength from 400 nm to 450 nm as blue laser may also be used. In addition, a surface emitting type laser light source capable of outputting multiple beams is also effective for forming a color image.

—Developing Device—

Examples of the developing device 11 include a general developing device that develops an image by contacting or non-contacting with a developer. The developing device 11 is not particularly limited as long as it has the above-described function, and is selected according to the purpose. Examples thereof include a known developing machine having a function of attaching a single-component developer or a two-component developer to the electrophotographic photoreceptor 7 using a brush, a roller, or the like. Among the examples, it is preferable to use a developing roller holding developer on a surface thereof.

The developer used for the developing device 11 may be a single-component developer of toner alone or a two-component developer including toner and a carrier. In addition, the developer may be magnetic or nonmagnetic. Known developers are adopted to these developers.

—Cleaning Device—

As the cleaning device 13, a cleaning blade type device including a cleaning blade 131 is used.

In addition to the cleaning blade type, a fur brush cleaning type and a development simultaneous cleaning type may be adopted.

—Transfer Device—

Examples of the transfer device 40 include a contact type transfer charger using a belt, a roller, a film, a rubber blade, or the like and a transfer charger known as it is such as a scorotron transfer charger or a corotron transfer charger using corona discharge.

—Intermediate Transfer Member—

As the intermediate transfer member 50, a belt-shaped member (intermediate transfer belt) containing polyimide, polyamideimide, polycarbonate, polyarylate, polyester, rubber, or the like to which semiconductivity is imparted is used. In addition, as a form of the intermediate transfer member, a drum-shaped member may be used in addition to the belt shape.

Figure 3:
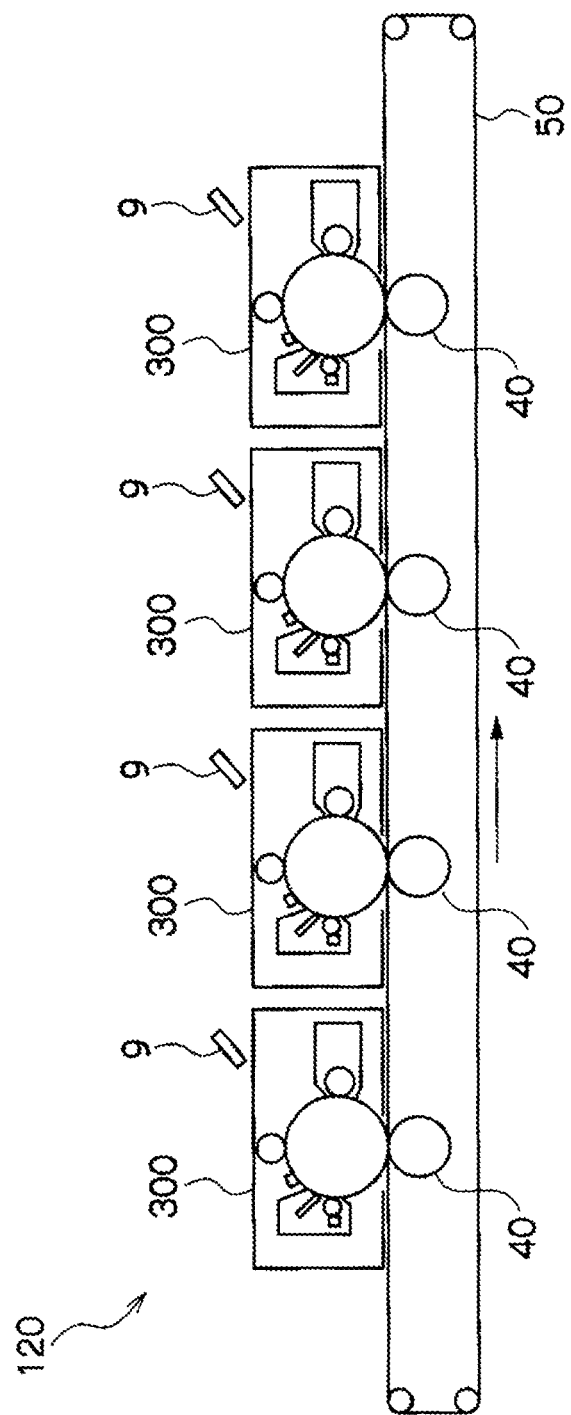
FIG. 3 is a schematic perspective diagram of another example of the image forming apparatus according to the exemplary embodiment.

FIG. 3 is a configuration diagram illustrating another example of the image forming apparatus according to the exemplary embodiment.

An image forming apparatus 120 shown in FIG. 3 is a tandem multicolor image forming apparatus on which four process cartridges 300 are mounted. The image forming apparatus 120 has a configuration in which four process cartridges 300 are arranged in parallel on the intermediate transfer member 50 and one electrophotographic photoreceptor is used for each color. The image forming apparatus 120 has the same configuration as that of the image forming apparatus 100 except for the tandem type.

Next, the second aspect of the present disclosure will be described in detail.

[Imide Compound]

The imide compound according to the exemplary embodiment has a structure represented by the following Formula (1A).

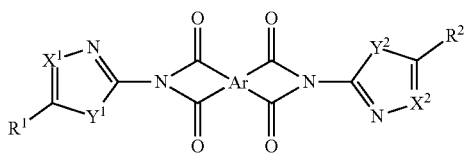

Formula (1A)

In Formula (1A), Ar represents an aromatic group having 6 to 18 carbon atoms except for a tetravalent perylene group, $X^1$ and $X^2$ each independently represent a nitrogen atom or a substituted or unsubstituted carbon atom, $Y^1$ and $Y^2$ each independently represent an oxygen atom, a sulfur atom, a selenium atom, or NH, and $R^1$ and $R^2$ each independently represent a hydrogen atom or a monovalent organic group.

An imide compound represented by Formula (1A) (hereinafter also referred to as "specific imide compound") exhibits a highly electron transporting ability. Therefore, the specific imide compound according to the exemplary embodiment is suitable for, for example, an application required to have electron transporting ability. For example, the specific imide compound is used for forming a film in photoelectric conversion device (such as an organic EL device and an electrophotographic photoreceptor), a solar cell, an organic transistor, and the like. Among the applications, the specific imide compound is suitably used for a film or layer required to have an electron transporting ability in an electrophotographic photoreceptor, and in particular, is used for a singlelayer type photosensitive layer (a photosensitive layer having a charge generating ability and a charge transporting ability) and a photosensitive layer of a laminated photoreceptor.

In the related art, an electrophotographic photoreceptor including a singlelayer type photosensitive layer containing a binder resin, a charge generation material, a hole transport material, and an electron transport material tends to have low compatibility between the binder resin and the electron transport material. When the compatibility between the binder resin and the electron transport material is low, the binder resin and the electron transport material are separated in the layer. Accordingly, in an interface at which separation occurs, cracking defect (also referred to as "crack") caused by internal stress or mechanical deformation may occur.

In addition, the specific imide compound tends to have high compatibility with the binder resin. Therefore, it is considered that crack is prevented from occurring in the electrophotographic photoreceptor in which the specific imide compound is contained in the singlelayer type photosensitive layer.

Next, a structure of a compound according to the exemplary embodiment will be described in detail.

[Specific Imide Compound]

The specific imide compound according to the exemplary embodiment has a structure represented by Formula (1A).

More specifically, the specific imide compound has an aromatic tetracarboxydiimide skeleton. Then, the specific imide compound has a structure in which two nitrogen atoms of the diimide group are substituted with a thiazole group, an oxazole group, a selenazole group, an oxadiazole group, or a diazole group each of which may independently have a substituent. (Ar)

In Formula (1A), Ar represents an aromatic group having 6 to 18 carbon atoms.

Examples of an aromatic group having 6 to 18 carbon atoms represented by Ar in Formula (1A) include a substituted or unsubstituted aromatic group.

Examples of the unsubstituted aromatic group having 6 to 18 carbon atoms include a tetravalent aromatic group obtained by removing arbitrary four hydrogen atoms from an aromatic hydrocarbon such as benzene, naphthalene, anthracene, phenanthrene, tetracene, benzoanthrene (tetraphene), benzophenanthrene (chrysene), triphenylene, pyrene, biphenyl, paraterphenyl, metaterphenyl, and 1-phenylnaphthalene. Here, the aromatic group having 6 to 18 carbon atoms represented by Ar in Formula (1A) does not contain a tetravalent perylene group.

Among the above groups, as the aromatic group represented by Ar in Formula (1A), a tetravalent naphthalene group is preferable.

Positions on the tetravalent aromatic group to be linked to carbon atoms of the imide groups (—N[C=O]$_2$—) in Formula (1A) are not particularly limited. The tetravalent aromatic group may be linked to the carbon atoms at arbitrary four points.

Here, the aromatic group having 6 to 18 carbon atoms means that the skeleton including only the aromatic group having no substituent has 6 to 18 carbon atoms.

Specific examples of an unsubstituted aromatic group having 6 to 18 carbon atoms represented by Ar in Formula (1A) include the following Ar-1 to Ar-8.

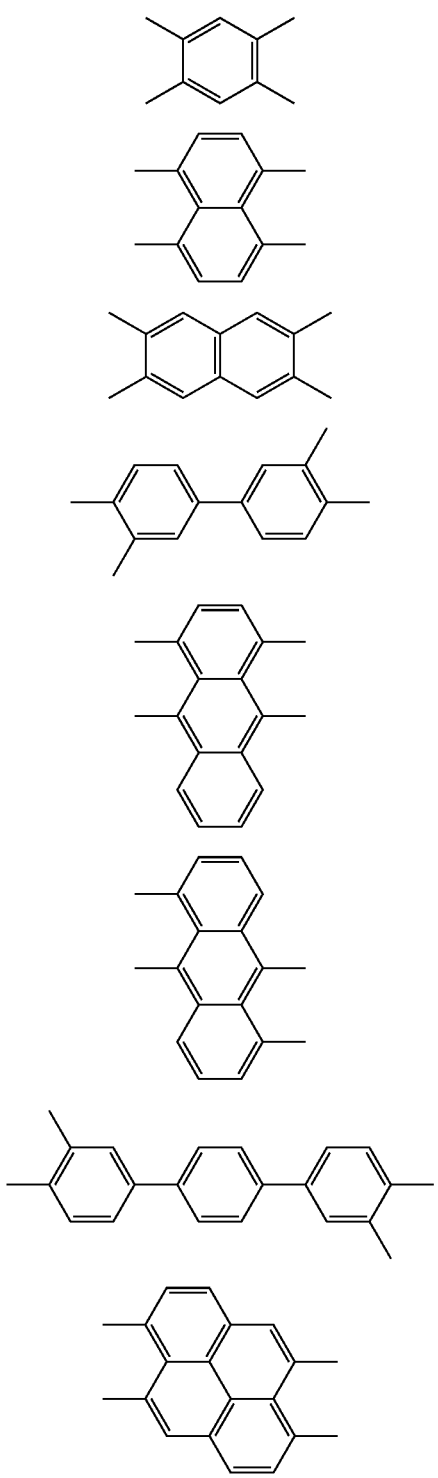

Examples of the substituent for the unsubstituted aromatic group having 6 to 18 carbon atoms represented by Ar in Formula (1A) include an alkyl group, an alkoxy group, and a halogen atom (chlorine, iodine, or bromine). Examples of the alkyl group of the alkyl-substituted aryl group include a linear or branched alkyl group having 1 to 10 (preferably 1 to 6 and more preferably 1 to 4) carbon atoms. Examples of the alkoxy group of the alkoxy-substituted aryl group include a linear or branched alkoxy group having 1 to 10 (preferably 1 to 6 and more preferably 1 to 4) carbon atoms.

($X^1$ and $X^2$)

In Formula (1A), $X^1$ and $X^2$ each independently represent a nitrogen atom or a substituted or unsubstituted carbon atom.

In a case where $X^1$ and $X^2$ represent a substituted carbon atom in Formula (1A), examples of the substituent which the substituted carbon atom has include an organic group having 1 to 40 carbon atoms.

Among the organic groups having 1 to 40 carbon atoms, the carbon atom preferably has a monovalent organic group formed by combining one or more kinds of a halogen atom, an aryl group having 6 to 30 carbon atoms, an aliphatic hydrocarbon group having 1 to 10 carbon atoms, an ether group, an alkoxy group, and an ester group.

Among the above, the carbon atom more preferably has a monovalent group formed by combining one or more kinds of an aliphatic hydrocarbon group having 1 to 10 carbon atoms, an ether group, an alkoxy group, and an ester group.

Examples of the aliphatic hydrocarbon group having 1 to 10 carbon atoms include an alkyl group and an alkylene group.

Examples of the above-described monovalent group include the following groups. In the following linking group, "*" represents a bond linked to the carbon atom represented by $X^1$ or $X^2$ in Formula (1A). $R^A$ represents an alkyl group, $R^B$ represents an alkylene group, $R^C$ represents a halogen atom, and $Ar^A$ represents an aryl group. $n_1$ represents an integer of 1 or more. When $n_1$ represents an integer of 2 or more, plural $R^B$'s may be the same or different.

—OH
—$R^A$
—O—$R^A$
—O—$Ar^A$
—$R^B$—O—$Ar^A$
—$R^C$
—$Ar^A$
—$R^B$—C(=O)—$R^A$
—$R^B$—OH
—$Ar^A$—OH
—$R^B$—O—$R^A$
—$R^B$—O—$Ar^A$
—O—$R^A$
—C(=O)—$R^A$
—C(=O)—O—$R^A$
—C(=O)—OH
—$R^B$—C(=O)—O—$R^A$
—$R^B$—C(=O)—O—($R^B$—O)$n_1$-$R^A$
—$R^B$—$R^C$
—$Ar^A$-$R^C$
—$R^B$—C(=O)—O—$R^B$—$Ar^A$
—$R^B$—C(=O)—O—$Ar^A$

Examples of the alkyl group represented by $R^A$ include a substituted or unsubstituted alkyl group.

Examples of the unsubstituted alkyl group represented by $R^A$ include a linear alkyl group having 1 to 10 carbon atoms (preferably 1 to 8 carbon atoms) and a branched alkyl group having 3 to 10 carbon atoms (preferably having 5 to 8 carbon atoms).

Examples of the linear alkyl group having 1 to 10 carbon atoms include a methyl group, an ethyl group, a n-propyl group, a n-butyl group, a n-pentyl group, a n-hexyl group, a n-heptyl group, a n-octyl group, a n-nonyl group, and a n-decyl group.

Examples of the branched alkyl group having 3 to 10 carbon atoms include an isopropyl group, an isobutyl group, a sec-butyl group, a tert-butyl group, an isopentyl group, a neopentyl group, a tert-pentyl group, an isohexyl group, a sec-hexyl group, a tert-hexyl group, an isoheptyl group, a sec-heptyl group, a tert-heptyl group, an isooctyl group, a sec-octyl group, a tert-octyl group, an isononyl group, a sec-nonyl group, a tert-nonyl group, an isodecyl group, a sec-decyl group, and a tert-decyl group.

Among the above groups, as the unsubstituted alkyl group, lower alkyl groups such as the methyl group and the ethyl group are preferable.

Examples of the substituent in the alkyl group represented by $R^A$ include an alkoxy group having 1 to 4 carbon atoms, an unsubstituted aryl group, a phenyl group substituted with an alkyl group or alkoxy group, having 1 to 4 carbon atoms, an aralkyl group having 7 to 10 carbon atoms, a hydroxyl group, a carboxyl group, a nitro group, and a halogen atom (chlorine, iodine, or bromine).

Examples of the alkoxy group of the alkoxy-substituted alkyl group include a linear or branched alkoxy group having 1 to 10 (preferably 1 to 6 and more preferably 1 to 4) carbon atoms. In addition, in a case where $X^1$ and $X^2$ in Formula (1A) to be described later are carbon atoms, examples of the aryl group of the aryl-substituted alkyl group include the same groups as the unsubstituted aryl group which is substituted for the carbon atom.

As the alkylene group represented by $R^B$, groups having a structure in which one hydrogen is further removed from the alkyl group represented by $R^A$ are preferable.

Examples of the halogen atom represented by $R^C$ include a fluorine atom, a chlorine atom, a bromine atom, and an iodine atom.

Examples of the aryl group represented by $Ar^A$ include a substituted or unsubstituted aryl group.

The unsubstituted aryl group is preferably an aryl group having 6 to 30 carbon atoms, and examples thereof include a phenyl group, a biphenyl group, a 1-naphthyl group, a 2-naphthyl group, a 9-anthryl group, a 9-phenanthryl group, a 1-pyrenyl group, a 5-naphthacenyl group, a 1-indenyl group, a 2-azulenyl group, a 9-fluorenyl group, a terphenyl group, a quaterphenyl group, o-, m-, and p-tolyl groups, a xylyl group, o-, m-, and p-cumenyl groups, a mesityl group, a pentalenyl group, a binaphthalenyl group, a tanaphthalenyl group, a quaternaphthalenyl group, a heptarenyl group, a biphenylenyl group, an indacenyl group, a fluoranthenyl group, an acenaphthylenyl group, an aceanthrylenyl group, a phenalenyl group, a fluorenyl group, an anthryl group, a bianthracenyl group, a teranthracenyl group, a quater anthracenyl group, an anthraquinolyl group, a phenanthryl group, a triphenylenyl group, a pyrenyl group, a chrysenyl group, a naphthacenyl group, a preadenyl group, a picenyl group, a perylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group. Among the above groups, the phenyl group is preferable.

Examples of the substituent in the aryl group include an alkyl group, an alkoxy group, and a halogen atom (chlorine, iodine, or bromine).

Examples of the alkyl group of the alkyl-substituted aryl group include the same groups as the unsubstituted alkyl group represented by $R^A$ in Formula (1A). In addition, in a case where $X^1$ and $X^2$ in Formula (1A) to be described later are carbon atoms, examples of the alkoxy group of the alkoxy-substituted aryl group include the same groups as the unsubstituted alkoxy group which is substituted for the carbon atom.

In a case where $X^1$ and $X^2$ in Formula (1A) represent a substituted carbon atom, examples of the alkoxy group which the substituted carbon atom may have include a substituted or unsubstituted alkoxy group.

In a case where $X^1$ and $X^2$ in Formula (1A) represent a substituted carbon atom, examples of the unsubstituted alkoxy group which the substituted carbon atom may have include a linear or branched alkoxy group having 1 to 10 (preferably 1 to 6 and more preferably 1 to 4) carbon atoms.

Specific examples of the linear alkoxy group include a methoxy group, an ethoxy group, a n-propoxy group, a n-butoxy group, a n-pentyloxy group, a n-hexyloxy group, a n-heptyloxy group, a n-octyloxy group, a n-nonyloxy group, and a n-decyloxy group. Specific examples of the branched alkoxy group include an isopropoxy group, an isobutoxy group, a sec-butoxy group, a tert-butoxy group, an isopentyloxy group, a neopentyloxy group, a tert-pentyloxy group, an isohexyloxy group, a sec-hexyloxy group, a tert-hexyloxy group, an isoheptyloxy group, a sec-heptyloxy group, a tert-heptyloxy group, an isooctyloxy group, a sec-octyloxy group, a tert-octyloxy group, an isononyloxy group, a sec-nonyloxy group, a tert-nonyloxy group, an isodecyloxy group, a sec-decyloxy group, and a tert-decyloxy group. Among the above groups, as the alkoxy group, the methoxy group is preferable.

In a case where $X^1$ and $X^2$ in Formula (1A) represent a substituted carbon atom, examples of the substituent in the substituted alkoxy group which the substituted carbon atom may have include an unsubstituted aryl group, a phenyl group substituted with an alkyl group, having 1 to 4 carbon atoms, an aralkyl group having 7 to 10 carbon atoms, a hydroxyl group, a carboxyl group, a nitro group, and a halogen atom (chlorine, iodine, or bromine).

Examples of the aryl group of the aryl-substituted alkoxy group include the same groups as the above-described unsubstituted aryl group represented by $Ar^A$.

($Y^1$ and $Y^2$)

In Formula (1A), $Y^1$ and $Y^2$ each independently represent an oxygen atom, a sulfur atom, a selenium atom, or NH.

Among the above, atoms represented by $Y^1$ and $Y^2$ in Formula (1A) are preferably a sulfur atom, an oxygen atom, or a selenium atom, more preferably a sulfur atom or an oxygen atom, and still more preferably a sulfur atom.

($R^1$ and $R^2$)

In Formula (1A), $R^1$ and $R^2$ each independently represent a hydrogen atom or a monovalent organic group.

Examples of the monovalent organic group represented by $R^1$ and $R^2$ in Formula (1A) include a monovalent organic group having 1 to 20 carbon atoms.

Among the above groups, the monovalent organic group is preferably a group formed by combining one or more kinds of a halogen atom, an aryl group, an aliphatic hydrocarbon group having 1 to 10 carbon atoms, an alkoxy group, and an ester group.

In addition, the monovalent organic group is more preferably a group formed by combining one or more kinds of an aliphatic hydrocarbon group having 1 to 10 carbon atoms, an alkoxy group, and an ester group.

Examples of the aliphatic hydrocarbon group having 1 to 10 carbon atoms include an alkyl group and an alkylene group.

Specific examples of the monovalent organic group include the following organic groups. In the following linking group, "*" represents a moiety linked to carbon atoms represented by $X^1$ and $X^2$ in Formula (1A). $R^{A2}$ represents an alkyl group, $R^{B2}$ represents an alkylene group, $R^{C2}$ represents a halogen atom, and $Ar^{A2}$ represents an aryl group. $n_1$ represents an integer of 1 or more. When $n_1$ represents an integer of 2 or more, plural $R^{B2}$'s may be the same or different.

—$R^{A2}$
—O—$R^{A2}$
—O—$Ar^{A2}$
—$R^{B2}$—O—$Ar^{A2}$
—$R^{C2}$
—$Ar^{A2}$
—$R^{B2}$—C(=O)—$R^{A2}$
—$R^{B2}$—O—$R^{A2}$
—O—$R^{A2}$
—C(=O)—$R^{A2}$
—C(=O)—O—$R^{A2}$
—$R^{B2}$—C(=O)—O—$R^{A2}$
—$R^{B2}$—C(=O)—O—($R^{B2}$—O)$n_1$-$R^{A2}$
—$R^{B2}$—$R^{C2}$
—$Ar^{A2}$—$R^{C2}$
—$R^{B2}$—C(=O)—O—$R^{B2}$-$Ar^{A2}$
—$R^{B2}$—C(=O)—O—$Ar^{A2}$

Examples of the alkyl group represented by $R^{A2}$ include a substituted or unsubstituted alkyl group.

Examples of the unsubstituted alkyl group represented by $R^{A2}$ include an alkyl group having 1 to 10 carbon atoms (preferably 1 to 8 carbon atoms).

In the case where $X^1$ and $X^2$ in Formula (1A) are carbon atoms, examples of a linear alkyl group having 1 to 10 carbon atoms include the same alkyl groups as the unsubstituted alkyl group which is substituted for the carbon atom.

As the alkylene group represented by $R^{B2}$, groups having a structure in which one hydrogen is further removed from the alkyl group represented by $R^{A2}$ are preferable.

In the case where $X^1$ and $X^2$ in Formula (1A) are carbon atoms, examples of the aryl group $Ar^{A2}$ represented by $R^1$ and $R^2$ in Formula (1A) include the same aryl groups as the unsubstituted aryl group $Ar^{A1}$ which is substituted for the carbon atom.

In the case where $X^1$ and $X^2$ in Formula (1A) are carbon atoms, examples of the alkoxy group represented by $R^1$ and $R^2$ in Formula (1A) include the unsubstituted alkoxy group which is substituted for the carbon atom.

Specific examples of the specific imide compound are shown below, but the specific imide compound is not limited thereto. An exemplary compound numbers in the following will be noted as Exemplary Compound (1A-number). Specifically, an exemplary compound 15 will be noted, for example, as "Exemplary Compound (1A-15)".

Formula (1A)

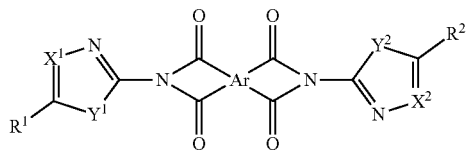

| Exemplary Compound | Ar | —$X^1$= *1 | —$X^2$= *1 | —$Y^1$— | —$Y^2$— | —$R^1$ | —$R^2$ |
|---|---|---|---|---|---|---|---|
| 1A-1 | Ar-1 | C—H | C—H | O | O | H | H |
| 1A-2 | Ar-1 | C—H | C—H | S | S | H | H |
| 1A-3 | Ar-1 | C—H | C—H | S | S | $CH_3$ | $CH_3$ |
| 1A-4 | Ar-1 | N | N | O | O | Ph | Ph |
| 1A-5 | Ar-1 | C—$CH_3$ | C—$CH_3$ | S | S | H | H |
| 1A-6 | Ar-1 | C—H | C—H | S | S | C(=O)$OCH_3$ | C(=O)$OCH_3$ |
| 1A-7 | Ar-1 | C—C(=O)$OCH_3$ | C—C(=O)$OCH_3$ | S | S | H | H |
| 1A-8 | Ar-1 | C—H | C—H | S | S | C(=O)$OCH_2CH_3$ | C(=O)$OCH_2CH_3$ |
| 1A-9 | Ar-1 | C—$CH_2$C(=O)$OCH_2CH_3$ | C—$CH_2$C(=O)$OCH_2CH_3$ | S | S | H | H |
| 1A-10 | Ar-1 | C—$CH_2$C(=O)$OCH_2CH_3$ | C—$CH_2$C(=O)$OCH_2CH_3$ | S | S | H | H |
| 1A-11 | Ar-1 | C—$CH_3$ | C—$CH_3$ | S | S | C(=O)$OCH_3$ | C(=O)$OCH_3$ |
| 1A-12 | Ar-1 | C—$CH_3$ | C—$CH_3$ | S | S | C(=O)$OCH_2CH_3$ | C(=O)$OCH_2CH_3$ |
| 1A-13 | Ar-1 | C—Ph | C—Ph | S | S | H | H |
| 1A-14 | Ar-1 | C—Ph—Br | C—Ph—Br | S | S | H | H |
| 1A-15 | Ar-2 | C—H | C—H | O | O | H | H |
| 1A-16 | Ar-2 | C—H | C—H | S | S | H | H |
| 1A-17 | Ar-2 | C—H | C—H | S | S | $CH_3$ | $CH_3$ |
| 1A-18 | Ar-2 | N | N | O | O | Ph | Ph |
| 1A-19 | Ar-2 | C—$CH_3$ | C—$CH_3$ | S | S | H | H |
| 1A-20 | Ar-2 | C—H | C—H | S | S | C(=O)$OCH_3$ | C(=O)$OCH_3$ |
| 1A-21 | Ar-2 | C—C(=O)$OCH_3$ | C—C(=O)$OCH_3$ | S | S | H | H |
| 1A-22 | Ar-2 | C—H | C—H | S | S | C(=O)$OCH_2CH_3$ | C(=O)$OCH_2CH_3$ |
| 1A-23 | Ar-2 | C—$CH_2$C(=O)$OCH_2CH_3$ | C—$CH_2$C(=O)$OCH_2CH_3$ | S | S | H | H |
| 1A-24 | Ar-2 | C—$CH_2$C(=O)$OCH_2CH_3$ | C—$CH_2$C(=O)$OCH_2CH_3$ | S | S | H | H |
| 1A-25 | Ar-2 | C—$CH_3$ | C—$CH_3$ | S | S | C(=O)$OCH_3$ | C(=O)$OCH_3$ |
| 1A-26 | Ar-2 | C—$CH_3$ | C—$CH_3$ | S | S | C(=O)$OCH_2CH_3$ | C(=O)$OCH_2CH_3$ |
| 1A-27 | Ar-2 | C—Ph | C—Ph | S | S | H | H |
| 1A-28 | Ar-2 | C—Ph—Br | C—Ph—Br | S | S | H | H |
| 1A-29 | Ar-2 | C—$CH_2$C(=O)$OCH_2CH_3$ | CH | S | S | H | H |
| 1A-30 | Ar-2 | C—$CH_2$C(=O)O$(CH_2)_7$—$CH_3$ | C—$CH_2$C(=O)O$(CH_2)_7$—$CH_3$ | S | S | H | H |
| 1A-31 | Ar-2 | C—$CH_2$C(=O)$OCH_2CH_2$—Ph | C—$CH_2$C(=O)$OCH_2CH_2$—Ph | S | S | H | H |
| 1A-32 | Ar-2 | 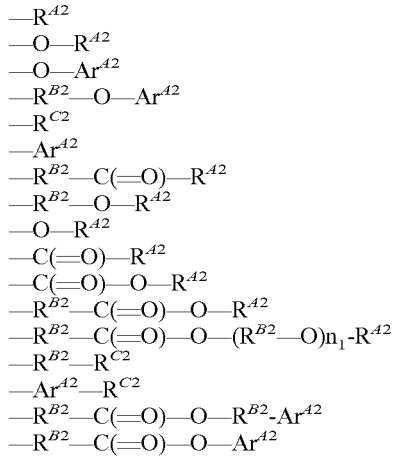 | 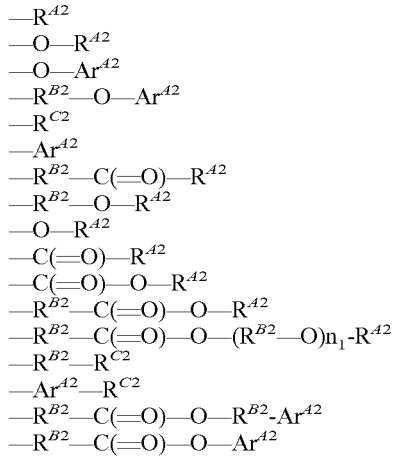 | S | S | H | H |

-continued

| Exemplary Compound | Ar | —X¹= *1 | —X²= *1 | —Y¹— | —Y²— | —R¹ | —R² |
|---|---|---|---|---|---|---|---|
| 1A-33 | Ar-2 | 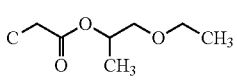 | 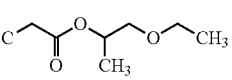 | S | S | H | H |
| 1A-34 | Ar-2 | N | N | Se | Se | H | H |
| 1A-35 | Ar-3 | C—H | C—H | O | O | H | H |

*1: With respect to $X^1$ being a carbon atom or $X^2$ being a carbon atom, the carbon atom at the left end shown in the table means a carbon atom linking to a nitrogen atom and a carbon atom in the azole skeleton.

| Exemplary Compound | Ar | —X¹= *1 | —X²= *1 | —Y¹— | —Y²— | —R¹ | —R² |
|---|---|---|---|---|---|---|---|
| 1A-36 | Ar-3 | C—H 1A- | C—H | S | S | H | H |
| 1A-37 | Ar-3 | C—H | C—H | S | S | CH₃ | CH₃ |
| 1A-38 | Ar-3 | N | N | O | O | Ph | Ph |
| 1A-39 | Ar-3 | C—CH₃ | C—CH₃ | S | S | H | H |
| 1A-40 | Ar-3 | C—H | C—H | S | S | C(=O)OCH₃ | C(=O)OCH₃ |
| 1A-41 | Ar-3 | C—C(=O)OCH₃ | C—C(=O)OCH₃ | S | S | H | H |
| 1A-42 | Ar-3 | CH | CH | S | S | C(=O)OCH₂CH₃ | C(=O)OCH₂CH₃ |
| 1A-43 | Ar-3 | C—CH₂C(=O)OCH₂CH₃ | C—CH₂C(=O)OCH₂CH₃ | S | S | H | H |
| 1A-44 | Ar-3 | C—C(=O)OCH₂CH₃ | C—C(=O)OCH₂CH₃ | S | S | H | H |
| 1A-45 | Ar-3 | C—CH₂C(=O)OCH₂CH₂—Ph | C—CH₂C(=O)OCH₂CH₂—Ph | S | S | H | H |
| 1A-46 | Ar-3 | 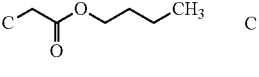 | 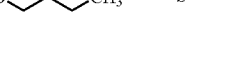 | S | S | H | H |
| 1A-47 | Ar-4 | C—H | C—H | O | O | H | H |
| 1A-48 | Ar-4 | C—H | C—H | S | S | H | H |
| 1A-49 | Ar-4 | C—H | C—H | S | S | CH₃ | CH₃ |
| 1A-50 | Ar-4 | N | N | O | O | Ph | Ph |
| 1A-51 | Ar-4 | C—CH₃ | C—CH₃ | S | S | H | H |
| 1A-52 | Ar-4 | C—H | C—H | S | S | C(=O)OCH₃ | C(=O)OCH₃ |
| 1A-53 | Ar-4 | C—C(=O)OCH₃ | C—C(=O)OCH₃ | S | S | H | H |
| 1A-54 | Ar-4 | C—H | C—H | S | S | C(=O)OCH₂CH₃ | C(=O)OCH₂CH₃ |
| 1A-55 | Ar-4 | C—CH₂C(=O)OCH₂CH₃ | C—CH₂C(=O)OCH₂CH₃ | S | S | H | H |
| 1A-56 | Ar-4 | C—C(=O)OCH₂CH₃ | C—C(=O)OCH₂CH₃ | S | S | H | H |
| 1A-57 | Ar-5 | C—C(=O)OCH₃ | C—C(=O)OCH₃ | S | S | H | H |
| 1A-58 | Ar-5 | C—H | C—H | S | S | C(=O)OCH₂CH₃ | C(=O)OCH₂CH₃ |
| 1A-59 | Ar-5 | C—CH₂C(=O)OCH₂CH₃ | C—CH₂C(=O)OCH₂CH₃ | S | S | H | H |
| 1A-60 | Ar-5 | C—C(=O)OCH₂CH₃ | C—C(=O)OCH₂CH₃ | S | S | H | H |
| 1A-61 | Ar-6 | C—C(=O)OCH₃ | C—C(=O)OCH₃ | S | S | H | H |
| 1A-62 | Ar-6 | C—H | C—H | S | S | C(=O)OCH₂CH₃ | C(=O)OCH₂CH₃ |
| 1A-63 | Ar-6 | C—CH₂C(=O)OCH₂CH₃ | C—CH₂C(=O)OCH₂CH₃ | S | S | H | H |
| 1A-64 | Ar-6 | C—C(=O)OCH₂CH₃ | C—C(=O)OCH₂CH₃ | S | S | H | H |
| 1A-65 | Ar-7 | C—CH₂C(=O)OCH₂CH₃ | C—CH₂C(=O)OCH₂CH₃ | S | S | H | H |
| 1A-66 | Ar-7 | C—C(=O)OCH₂CH₃ | C—C(=O)OCH₂CH₃ | S | S | H | H |
| 1A-67 | Ar-8 | C—CH₂C(=O)OCH₂CH₃ | C—CH₂C(=O)OCH₂CH₃ | S | S | H | H |
| 1A-68 | Ar-8 | C—C(=O)OCH₂CH₃ | C—C(=O)OCH₂CH₃ | S | S | H | H |
| 1A-69 | Ar-2 | C—H | C—H | S | Se | H | H |
| 1A-70 | Ar-2 | C—H | C—H | S | O | H | H |
| 1A-71 | Ar-2 | C—H | C—H | S | NH | H | H |
| 1A-72 | Ar-2 | C—H | C—H | Se | O | H | H |
| 1A-73 | Ar-2 | C—H | C—H | Se | NH | H | H |
| 1A-74 | Ar-2 | C—H | C—H | O | NH | H | H |
| 1A-75 | Ar-2 | C—H | C—H | NH | NH | H | H |
| 1A-76 | Ar-2 | C—H | C—H | S | S | C(=O)OCH₃ | C(=O)OCH₂CH₃ |
| 1A-77 | Ar-2 | C—H | C—H | S | S | CH₃ | C(=O)OCH₃ |

*1: With respect to $X^1$ being a carbon atom or $X^2$ being a carbon atom, the carbon atom at the left end shown in the table means a carbon atom linking to a nitrogen atom and a carbon atom in the azole skeleton.

[Method of Synthesizing Specific Imide Compound]

Hereinafter, a method of synthesizing the specific imide compound will be described.

The method of synthesizing the specific imide compound is not particularly limited, and the specific imide compound may be synthesized by a known method. For example, as shown below, the specific imide compound may be synthesized by dehydration condensation of corresponding aromatic tetracarboxylic dianhydride and an aminoazole compound.

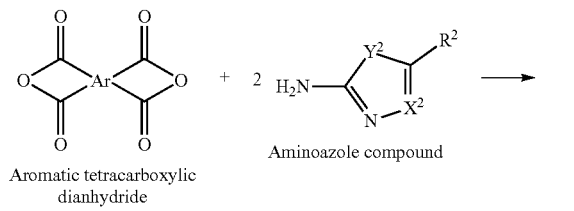

Aromatic tetracarboxylic dianhydride

Aminoazole compound

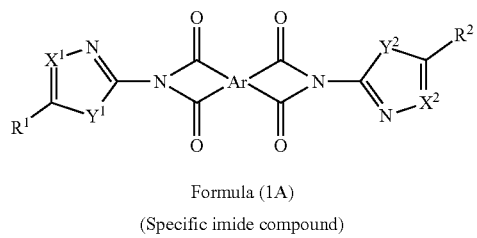

Formula (1A)
(Specific imide compound)

In a synthesis reaction of the specific imide compound, a solvent is not necessarily used. However, when the solvent is used, preferable examples of the solvent include N,N-dimethylformamide (DMF), dimethylacetamide (DMAc), 1,3-dimethyl-2-imidazolidinone (DMI), N-methyl-2-pyrrolidone (NMP), and dimethyl sulfoxide (DMSO).

Here, for example, in a case of synthesizing a specific imide compound in which $X^1$, $X^2$, $Y^1$, $Y^2$, $R^1$, and $R^2$ independently have different groups or atoms, the specific imide compound may be synthesized by dehydration condensation of two corresponding aminoazole compounds and an aromatic tetracarboxylic dianhydride.

In a case of synthesizing a specific imide compound having an ester group in $R^1$ or $R^2$, a specific imide compound (1A) having an ester group is synthesized by reacting the aromatic tetracarboxylic dianhydride with the aminoazole compound. Thereafter, a specific imide compound (2A) having various ester groups may be synthesized by reacting a predetermined alcohol ($R^{ES}$—OH) with $R^1$ or $R^2$ by transesterification reaction in presence of an acid catalyst, as needed.

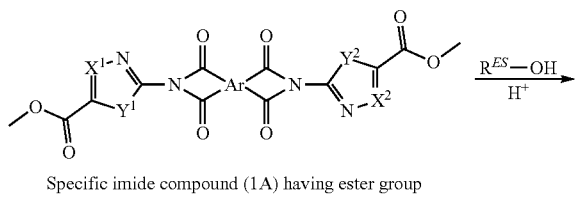

Specific imide compound (1A) having ester group

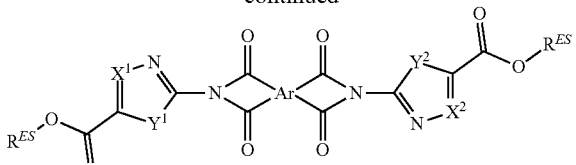

Specific imide compound (2A) having ester group

The acid catalyst in the transesterification reaction is not particularly limited, and for example, an acid catalyst used in a usual esterification reaction, such as sulfuric acid, toluenesulfonic acid, and trifluoroacetic acid may be used.

The specific imide compound according to the exemplary embodiment may be used for, for example, an electron transport material in an electrophotographic photoreceptor, a solar cell, and an organic transistor.

[Electrophotographic Photoreceptor]

The electrophotographic photoreceptor according to the exemplary embodiment includes a conductive substrate, a singlelayer type photosensitive layer that is disposed on the conductive substrate and includes an electron transport material containing the specific imide compound, a binder resin, a charge generation material, and a hole transport material. The electrophotographic photoreceptor may further include an undercoating layer, a protective layer, and the like, as needed.

Hereinafter, the electrophotographic photoreceptor according to the exemplary embodiment will be described in detail with reference to the drawings. In the drawings, the same or corresponding parts are denoted by the same reference numerals, and duplicated description will be omitted.

Figure 4:
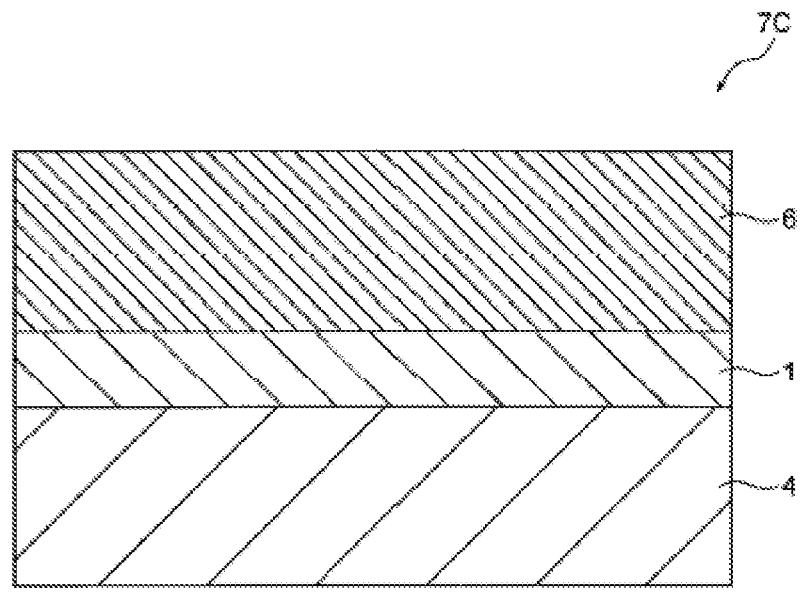
FIG. 4 is a schematic partial sectional diagram illustrating another example of the layer configuration of the electrophotographic photoreceptor according to the exemplary embodiment.

FIG. 4 is a schematic partial sectional diagram illustrating an example of the layer configuration of the electrophotographic photoreceptor according to the exemplary embodiment. An electrophotographic photoreceptor 7C shown in FIG. 4 contains the charge generation material and the charge transport material in the same layer (a singlelayer type photosensitive layer 6). The electrophotographic photoreceptor 7C shown in FIG. 4 has a structure in which the undercoating layer 1 is provided on the conductive substrate 4, and the singlelayer type photosensitive layer 6 is formed thereon. In the electrophotographic photoreceptor 7C, for example, the specific imide compound is contained in the singlelayer type photosensitive layer 6. In the electrophotographic photoreceptor shown in FIG. 4, the undercoating layer 1, the protective layer, and the like may be provided or also not be provided.

Hereinafter, each layer of the electrophotographic photoreceptor according to the exemplary embodiment will be described in detail. Descriptions will be given without reference numerals.

[Conductive Substrate]

Hereinafter, the conductive substrate will be described.

The electrophotographic photoreceptor includes the conductive substrate.

Examples of the conductive substrate include a metal plate including a metal (such as aluminum, copper, zinc, chromium, nickel, molybdenum, vanadium, indium, gold, and platinum) or an alloy (such as stainless steel), a metal drum, and a metal belt. In addition, examples of the conductive substrate also include paper, a resin film, and a belt which are obtained by applying, vapor-depositing, or laminating a conductive compound (for example, a conductive polymer, indium oxide, or the like), metal (for example, aluminum, palladium, gold, or the like), or an alloy. Here, "conductive" means that the volume resistivity is less than 1013 (Ω·cm).

In a case where the electrophotographic photoreceptor is used in a laser printer, the surface of the conductive substrate preferably roughened to have a center line average roughness Ra from 0.04 μm to 0.5 μm in order to prevent interference fringes generated when emitting laser light. In a case of using non-interference light as a light source, although roughening for prevention of interference fringes is not particularly necessary, since the roughening prevents defects from occurring due to irregularities on the surface of the conductive substrate, it is suitable for longer life.

Examples of a surface-roughening method include wet honing performed by suspending an abrasive in water and blowing suspension on the conductive substrate, centerless grinding performed by pressing the conductive substrate against a rotating grindstone and performing continuous grinding processing, and anodic oxidation.

Examples of the surface-roughening method also include a method in which a conductive or semi-conductive powder is dispersed in a resin without roughening the surface of the conductive substrate to form a layer on the surface of the conductive substrate and surface-roughening is performed by particles dispersed in the layer.

The surface roughening treatment by anodic oxidation is to form an oxide film on the surface of the conductive substrate by anodizing in an electrolyte solution using a conductive substrate made of metal (for example, aluminum) as an anode. Examples of the electrolyte solution include a sulfuric acid solution and an oxalic acid solution. However, a porous anodic oxide film formed by the anodic oxidation is chemically active in the state as it is, is likely to be stained, and has a large change in resistance depending on the environment. Therefore, the porous anodic oxide film is preferably subjected to a sealing treatment that fine pores of the oxide film are blocked by volume expansion due to hydration reaction in pressurized water vapor or boiling water (a metal salt such as nickel may be added) to be changed to a more stable hydrated oxide.

A thickness of the anodic oxide film is preferably, for example, from 0.3 μm to 15 μm. When the film thickness is within the above range, there is tendency that barrier properties against injection is exhibited, and there is tendency that residual potential is prevented from increasing due to repeated use.

The conductive substrate may also be subjected to a treatment with an acidic treatment solution or a boehmite treatment.

The treatment with the acidic treatment solution is carried out, for example, as follows. First, an acidic treatment liquid containing phosphoric acid, chromic acid, and hydrofluoric acid is prepared. A mixing ratio of the phosphoric acid, the chromic acid, and the hydrofluoric acid in the acidic treatment solution is, for example, from 10% by weight to 11% by weight of phosphoric acid, 3% by weight to and 5% by weight of chromic acid, and 0.5% by weight to 2% by weight, and a concentration of these whole acids may be from 13.5% by weight to 18% by weight. A treatment temperature is preferably, for example, from 42° C. to 48° C. A film thickness of the film to be coated is preferably from 0.3 μm to 15 μm.

The boehmite treatment is carried out by, for example, dipping the conductive substrate in deionized water from 90° C. to 100° C. for 5 minutes to 60 minutes, or contacting the conductive substrate to heated steam from 90° C. to 120° C. for 5 minutes to 60 minutes. A film thickness of the film to be coated is preferably from 0.1 μm to 5 μm. The anodic oxidation may be further performed using an electrolyte solution having low film solubility such as adipic acid, boric acid, borate, phosphate, phthalate, maleate, benzoate, tartrate, and citrate.

[Singlelayer Type Photosensitive Layer]

Hereinafter, the singlelayer type photosensitive layer will be described.

The singlelayer type photosensitive layer contains an electron transport material, a binder resin, a charge generation material, and a hole transport material.

Hereinafter, each material contained in the singlelayer type photosensitive layer will be described in detail.

(Electron Transport Material)

Hereinafter, the electron transport material will be described.

The photosensitive layer according to the exemplary embodiment contains the electron transport material containing the specific imide compound.

When the specific imide compound is contained as the electron transport material, the compatibility with the binder resin increases. Therefore, cracks in the photosensitive layer are prevented from occurring.

Other electron transport materials are not particularly limited, but examples thereof include electron transport compounds such as: quinone compounds such as p-benzoquinone, chloranil, bromanil, and anthraquinone; a tetracyanoquinodimethane compound; a fluorenone compound such as 2,4,7-trinitrofluorenone; fluorene compounds such as dicyanomethylene fluorene; a xanthone compound; a benzophenone compound; a cyanovinyl compound; and an ethylene compound.

Specific examples thereof include the following electron transport materials ET-1 to ET-9.

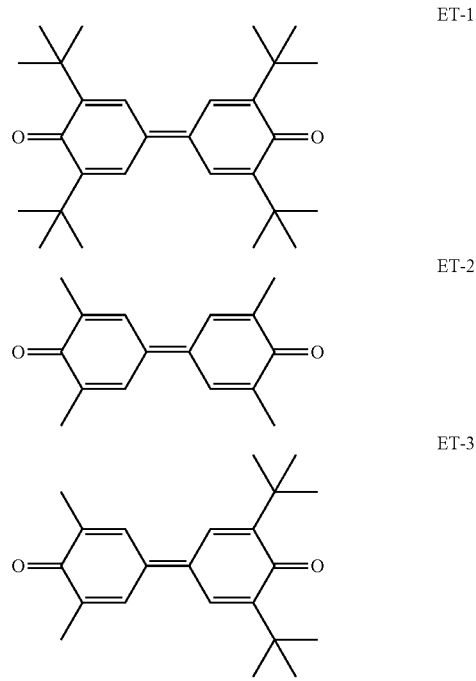

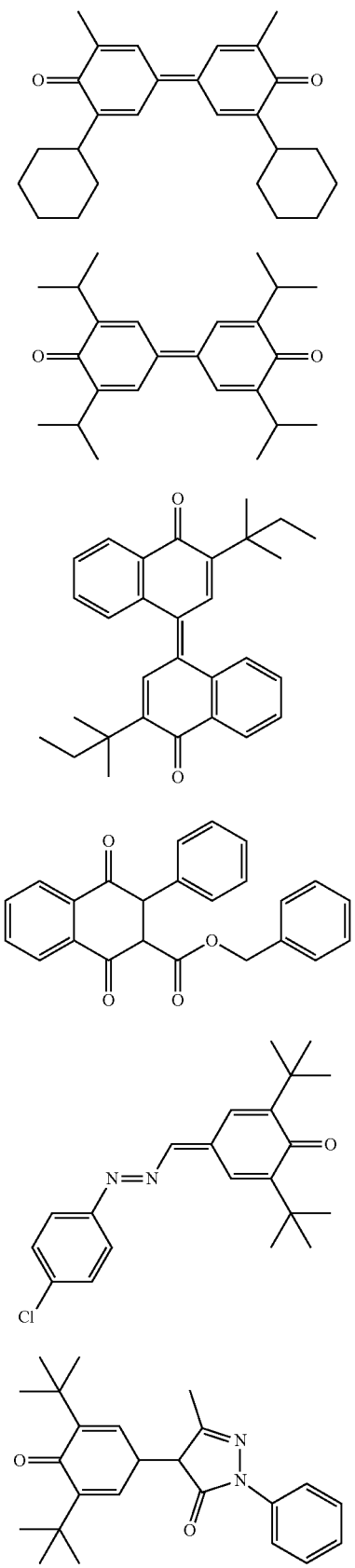

ET-4

ET-5

ET-6

ET-7

ET-8

ET-9

A proportion of the specific imide compound in the electron transport material is preferably from 90% by weight to 100% by weight, and more preferably from 98% by weight to 100% by weight.

A content of the electron transport material in the photosensitive layer is preferably from 5% by weight to 30% by weight and more preferably 10% by weight to 20% by weight, from the viewpoint of preventing cracks in the photosensitive layer from occurring.

(Binder Resin)

Examples of the binder resin include a polycarbonate resin, a polyester resin, a polyarylate resin, a methacrylic resin, an acrylic resin, a polyvinyl chloride resin, a polyvinylidene chloride resin, a polystyrene resin, a polyvinyl acetate resin, a styrene-butadiene copolymer, a vinylidene chloride-acrylonitrile copolymer, a vinyl chloride-vinyl acetate copolymer, a vinyl chloride-vinyl acetate-maleic anhydride copolymer, a silicone resin, a silicone alkyd resin, a phenol-formaldehyde resin, a styrene-alkyd resin, a poly-N-vinylcarbazole, and a polysilane. One kind of these binder resins may be used alone and two or more kinds thereof may be used in combination.

From the viewpoint of preventing point defects of an image to be obtained from occurring, the binder resin is preferably at least one selected from the group consisting of a polycarbonate resin, a polyester resin, and a polyarylate resin, and more preferably a polycarbonate resin, and particularly preferably a bisphenol Z polycarbonate resin.

The bisphenol Z polycarbonate resin refers to a polycarbonate resin having a bisphenol Z structure, that is, a structure obtained by removing hydrogen atoms of two hydroxy groups from 1,1-bis(4-hydroxyphenyl)cyclohexane.

In addition, from the viewpoint of the film formability of the photosensitive layer, the binder resin preferably has a viscosity average molecular weight from 30,000 to 80,000.

A content R of the binder resin based on the total weight of the photosensitive layer is preferably within the above-described range.

(Charge Generation Material)

Examples of the charge generation material include azo pigments such as bisazo and trisazo; a condensed ring aromatic pigment such as dibromoanthanthrone; a perylene pigment; a pyrrolopyrrole pigment; a phthalocyanine pigment; zinc oxide; and trigonal selenium.

From the viewpoint of improving sensitivity of the photosensitive layer, the charge generation material is preferably the phthalocyanine pigment. Specifically, examples of the phthalocyanine pigment include hydroxygallium phthalocyanine; chlorogallium phthalocyanine; dichlorotin phthalocyanine; and titanyl phthalocyanine.

From the viewpoint of charge generation efficiency, the charge generation material is preferably at least any one of hydroxygallium phthalocyanine and chlorogallium phthalocyanine, more preferably hydroxygallium phthalocyanine, and still more preferably V-type hydroxygallium phthalocyanine.

From the viewpoint of charge generation efficiency, the hydroxygallium phthalocyanine is preferably hydroxygallium phthalocyanine having the maximum peak wavelength from 810 nm to 839 nm in a spectral absorption spectrum at a wavelength range from 600 nm to 900 nm.

The hydroxygallium phthalocyanine having the maximum peak wavelength from 810 nm to 839 nm has an average particle diameter within a specific range, and preferably has a BET specific surface area within a specific range. Specifically, the average particle diameter is preferably 0.20 µm or less, more preferably from 0.01 µm to 0.15 µm. The BET specific surface area is preferably 45 m²/g or more, more preferably 50 m²/g or more, and still more preferably from 55 m²/g to 120 m²/g. The average particle diameter is a volume average particle diameter, and a value obtained by measurement using a laser diffraction type particle size distribution measuring apparatus (LA-700 manufactured by Horiba. Ltd.). The BET specific surface area is a value obtained by measurement by a nitrogen substitution method using a fluid type specific surface area automatic measuring apparatus (FLOWSORB II 2300 manufactured by Shimadzu Corporation).

The maximum particle diameter (the maximum value of the primary particle diameter) of the hydroxygallium phthalocyanine is preferably 1.2 µm or less, more preferably 1.0 µm or less, and still more preferably 0.3 µm or less.

The hydroxygallium phthalocyanine preferably has an average particle diameter of 0.2 µm or less, the maximum particle diameter of 1.2 µm or less, and the BET specific surface area of 45 m²/g or more.

The hydroxygallium phthalocyanine is preferably a V-type hydroxygallium phthalocyanine having diffraction peaks at Bragg angles (2θ±0.2°) of at least 7.3°, 16.0°, 24.9°, and 28.0° in an X-ray diffraction spectrum using a Cu Kα characteristic X-ray.

From the viewpoint of improving sensitivity of the photosensitive layer, the chlorogallium phthalocyanine is preferably a compound having diffraction peaks at Bragg angles (2θ±0.2°) of 7.4°, 16.6°, 25.5°, 28.3°. Preferable ranges of maximum peak wavelength, an average particle diameter, the maximum particle diameter, and a BET specific surface area of the chlorogallium phthalocyanine is the same as those of the hydroxygallium phthalocyanine.

One kind of the charge generation material may be used alone and two or more kinds thereof may be used in combination.

A content of the charge generation material in the single-layer type photosensitive layer is preferably from 0.1% by weight to 10% by weight, more preferably from 0.5% by weight to 5% by weight, and particularly preferably from 1% by weight to 3% by weight, based on the total weight of the photosensitive layer.

(Hole Transport Material)

Examples of the hole transport material include hole transporting compounds such as a triarylamine compound, a benzidine compound, an arylalkane compound, an aryl-substituted ethylene compound, a stilbene compound, an anthracene compound, and a hydrazone compound.

These hole transport materials may be used alone or in combination of two or more thereof, but are not limited thereto.

As the hole transport material, from the viewpoint of charge mobility, a triarylamine derivative represented by the following Formula (B-1) and a benzidine derivative represented by the following Formula (B-2) are preferable.

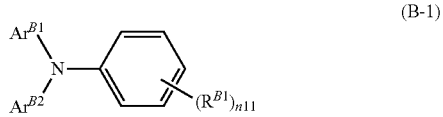

(B-1)

(In Formula (B-1), $R^{B1}$ represents a hydrogen atom or a methyl group. n11 represents 1 or 2. $Ar^{B1}$ and $Ar^{B2}$ each independently represent a substituted or unsubstituted aryl group, $-C_6H_4-C(R^{B3})=C(R^{B4})(R^{B5})$, or $-C_6H_4-CH=CH-CH=C(R^{B6})(R^{B7})$. $R^{B3}$ to $R^{B7}$ each independently represent a hydrogen atom, a substituted or unsubstituted alkyl group, or a substituted or unsubstituted aryl group.)

Examples of the substituent include a halogen atom, an alkyl group having 1 to 5 carbon atoms, an alkoxy group having 1 to 5 carbon atoms, and a substituted amino group substituted with an alkyl group having 1 to 3 carbon atoms.

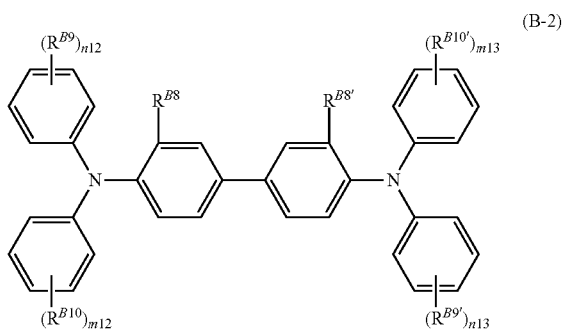

(B-2)

(In Formula (B-2), $R^{B8}$ and $R^{B8'}$ may be the same or different from each other, and each independently represent a hydrogen atom, a halogen atom, an alkyl group having 1 to 5 carbon atoms, or an alkoxy group having 1 to 5 carbon atoms. $R^{B9}$, $R^{B9'}$, $R^{B10}$, and $R^{B10'}$ may be the same or different from each other, and each independently represent a hydrogen atom, a halogen atom, an alkyl group having 1 to 5 carbon atoms, an alkoxy group having 1 to 5 carbon atoms, an amino group having 1 or 2 carbon atoms substituted with an alkyl group, a substituted or unsubstituted aryl group, $-C(R^{B11})=C(R^{B12})(R^{B13})$, or $-CH=CH-CH=C(R^{B14})(R^{B15})$. $R^{B11}$ to $R^{B15}$ each independently represent a hydrogen atom, a substituted or unsubstituted alkyl group, or a substituted or unsubstituted aryl group. m12, m13, n12, and n13 each independently represent an integer of 0 to 2.)

Among the triarylamine derivative represented by Formula (B-1) and the benzidine derivative represented by Formula (B-2), a triarylamine derivative having "$-C_6H_4-CH=CH-CH=C(R^{B6})(R^{B7})$" and a benzidine derivative having "$-CH=CH-CH=C(R^{B14})(R^{B15})$" are particularly preferable.

Specific examples of the hole transport material used in the photosensitive layer in the exemplary embodiment include the following compounds, in addition to the triarylamine derivative represented by Formula (B-1) and the benzidine derivative represented by Formula (B-2).

HT-1
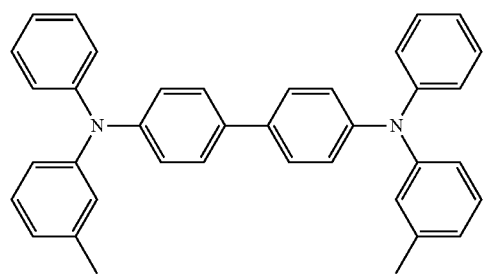
HT-2
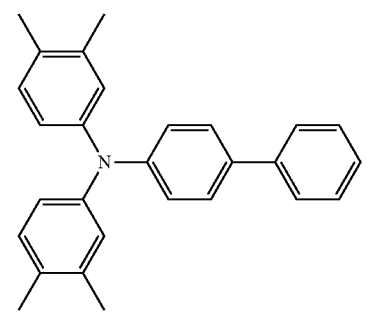
HT-3
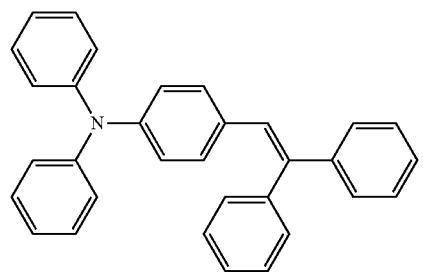
HT-4
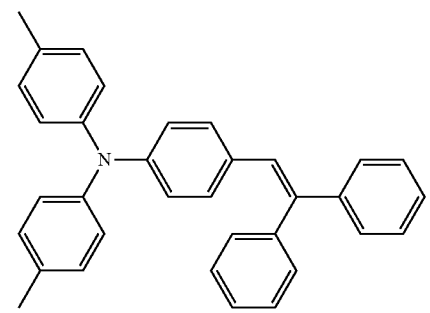
HT-5
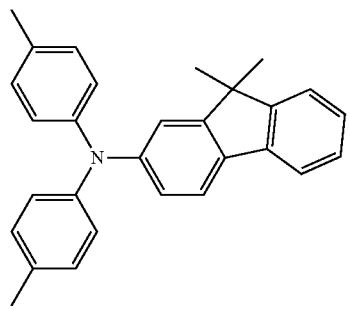
HT-6
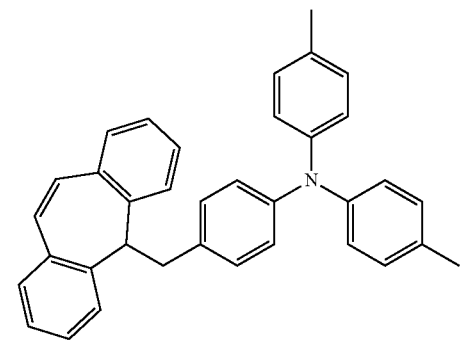
HT-7
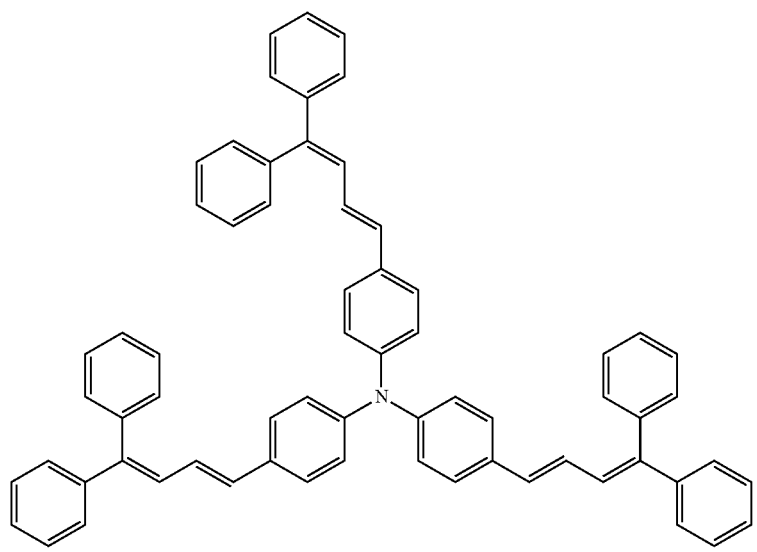

HT-8
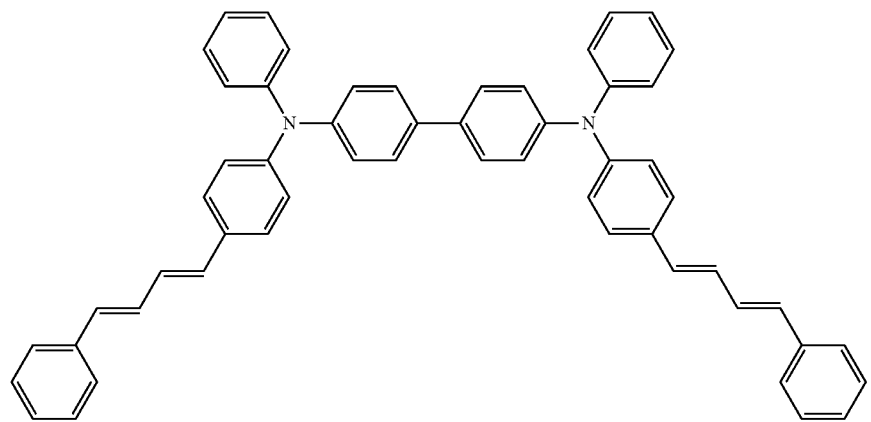
HT-9
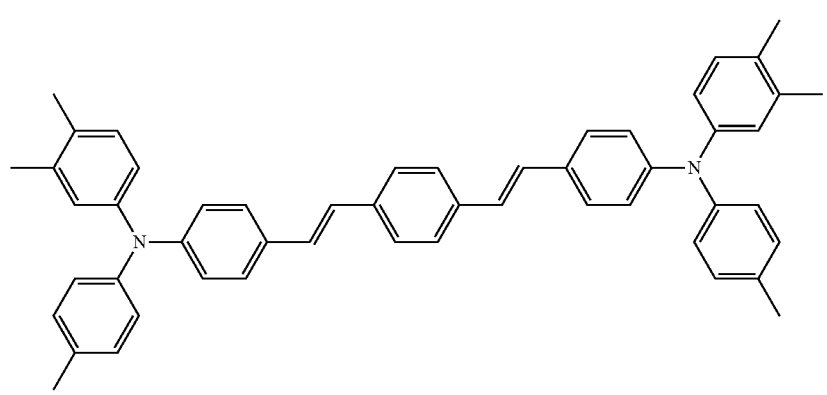
HT-10
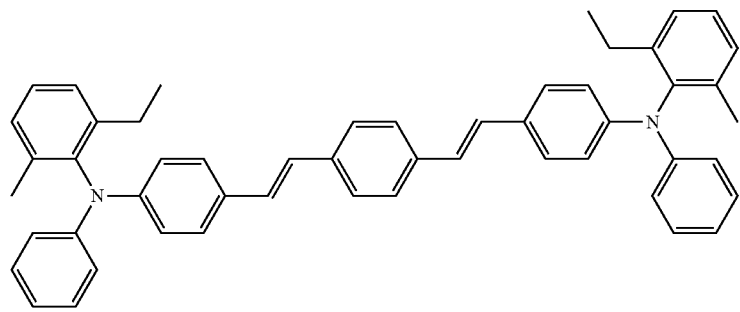
HT-11
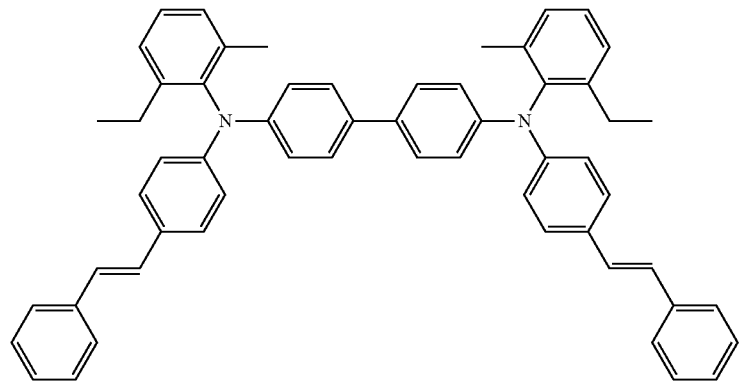

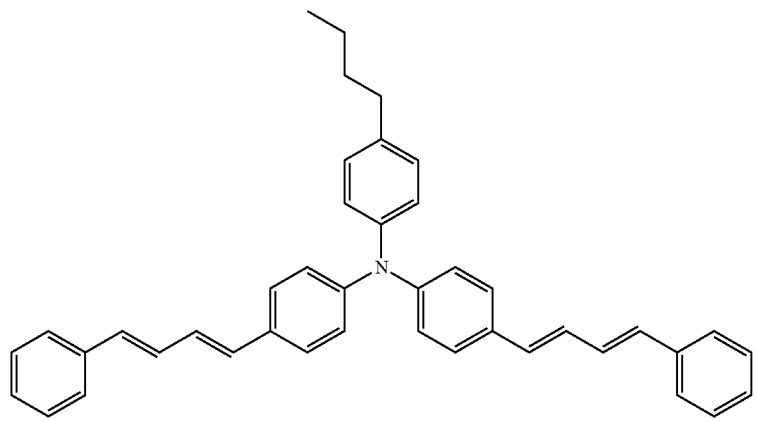

HT-12

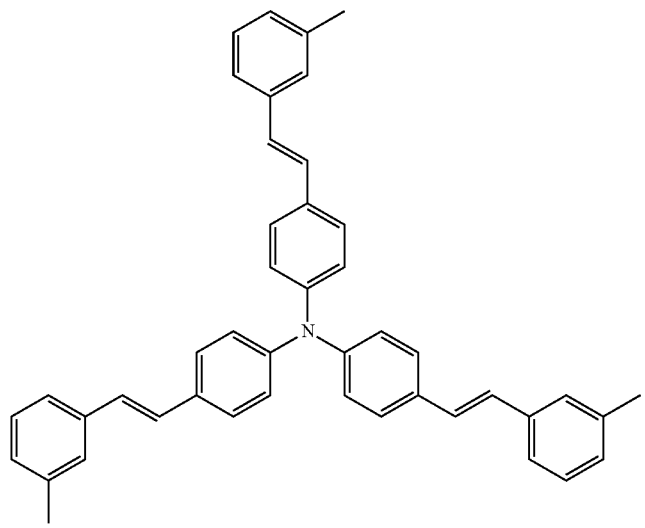

HT-13

A content of the hole transport material may be from 10% by weight to 50% by weight, and is preferably from 20% by weight to 40% by weight, based on the total solid content of the singlelayer type photosensitive layer.

(Ratio Between Hole Transport Material and Electron Transport Material)

A ratio between the hole transport material and the electron transport material is preferably from 50:50 to 90:10 and more preferably from 60:40 to 80:20 in terms of weight ratio (hole transport material:electron transport material).

In addition, as hole transport material, it is preferable to use at least one of the triarylamine derivative represented by Formula (B-1) and the benzidine derivative represented by Formula (B-2) and use a compound having a structure represented by the specific imide compound according to the exemplary embodiment, as the electron transport material.

(Other Additives)

The singlelayer type photosensitive layer may contain known other additives such as a surfactant, an antioxidant, fine particles (such as silicon carbide), a light stabilizer, and a heat stabilizer. In addition, in a case where the singlelayer type photosensitive layer is a surface layer, the singlelayer type photosensitive layer may contain fluorine resin particles, silicone oil, or the like.

[Formation of Singlelayer Type Photosensitive Layer]

The singlelayer type photosensitive layer is formed by using a photosensitive layer-forming coating liquid obtained by adding the above components to a solvent.

Examples of the solvent include usual organic solvents such as aromatic hydrocarbons such as benzene, toluene, xylene, and chlorobenzene; ketones such as acetone and 2-butanone; halogenated aliphatic hydrocarbons such as methylene chloride, chloroform, and ethylene chloride; and cyclic or linear ethers such as tetrahydrofuran and ethyl ether. One kind of the solvents used alone and two or more kinds thereof are used by being mixed.

In a method for dispersing particles (for example, charge generation material) in the photosensitive layer-forming coating liquid, for example, a media dispersing machine such as a ball mill, a vibration ball mill, an attritor, a sand mill, and a horizontal sand mill or a medialess dispersing machine such as a stirrer, an ultrasonic dispersing machine, a roll mill, and a high-pressure homogenizer is used. Examples of the high-pressure homogenizer include a collision type in which dispersing is performed by a liquid-liquid collision or a liquid-wall collision in a high pressure state, or a penetration type in which dispersing is performed by penetrating a fine flow path in a high pressure state.

Examples of a method of applying the photosensitive layer-forming coating liquid onto the undercoating layer include a dipping coating method, an extrusion coating method, a wire bar coating method, a spray coating method, a blade coating method, a knife coating method, and a curtain coating method.

A film thickness of the singlelayer type photosensitive layer is set preferably from 5 μm to 60 μm, and more preferably from 10 μm to 40 μm.

[Undercoating Layer]

Hereinafter, the undercoating layer will be described.

The undercoating layer is, for example, a layer containing inorganic particles and a binder resin.

Examples of the inorganic particles include inorganic particles having a powder resistance (volume resistivity) from $10^2$ Ω·cm to $10^{11}$ Ω·cm.

Among these particles, the inorganic particles having the above resistance value may be, for example, metal oxide particles such as tin oxide particles, titanium oxide particles, zinc oxide particles, and zirconium oxide particles, and the zinc oxide particles are particularly preferable.

A specific surface area of the inorganic particles by a BET method may be preferably, for example, 10 $m^2$/g or more.

A volume average particle diameter of the inorganic particles may be, for example, from 50 nm to 2,000 nm (preferably from 60 nm to 1,000 nm).

A content of the inorganic particles is, for example, preferably from 10% by weight to 80% by weight, and more preferably from 40% by weight to 80% by weight with respect to the binder resin.

The inorganic particles may be subjected to a surface treatment. Two or more kinds of the inorganic particles, which are subjected to different surface treatments or have different particle diameters, may be mixed to be used.

Examples of a surface treatment agent include a silane coupling agent, a titanate coupling agent, an aluminum coupling agent, and a surfactant. In particular, the silane coupling agent is preferable, and a silane coupling agent having an amino group is more preferable.

Examples of the silane coupling agent having an amino group include 3-aminopropyltriethoxysilane, N-2-(aminoethyl)-3-aminopropyltrimethoxysilane, N-2-(aminoethyl)-3-amino propylmethyldimethoxysilane, and N,N-bis(2-hydroxyethyl)-3-aminopropyltriethoxysilane, but are not limited thereto.

Two or more kinds of the silane coupling agents may be mixed to be used. For example, the silane coupling agent having an amino group and the other silane coupling agent may be used in combination. Examples of the other silane coupling agent include vinyltrimethoxysilane, 3-methacryloxypropyl-tris(2-methoxyethoxy)silane, 2-(3,4-epoxycyclohexyl)ethyltrimethoxysilane, 3-glycidoxypropyltrimethoxysilane, vinyltriacetoxysilane, 3-mercaptopropyltrimethoxysilane, 3-aminopropyltriethoxysilane, N-2-(aminoethyl)-3-aminopropyltrimethoxysilane, N-2-(aminoethyl)-3-aminopropylmethyldimethoxysilane, N,N-bis(2-hydroxyethyl)-3-aminopropyltriethoxysilane, and 3-chloropropyltrimethoxysilane, but are not limited thereto.

The surface treatment method with the surface treatment agent may be any method as long as it is a known method, and either a dry method or a wet method may be used.

A throughput of the surface treatment agent is, for example, preferably from 0.5% by weight to 10% by weight, with respect to the inorganic particles.

Here, the undercoating layer may contain an electron accepting compound (acceptor compound) together with the inorganic particles, from the viewpoint of improving long-term stability of electric characteristics and carrier blocking property.

Examples of the electron accepting compound include electron transport substances such as: quinone compounds such as chloranil and bromoanil; a tetracyanoquinodimethane compound; fluorenone compounds such as 2,4,7-trinitrofluorenone and 2,4,5,7-tetranitro-9-fluorenone; oxadiazole compounds such as 2-(4-biphenyl)-5-(4-t-butylphenyl)-1,3,4-oxadiazole, 2,5-bis(4-naphthyl)-1,3,4-oxadiazole, and 2,5-bis(4-diethylaminophenyl)-1,3,4-oxadiazole; a xanthone compound; a thiophene compound; and diphenoquinone compounds such as 3,3',5,5'-tetra-t-butyldiphenoquinone.

In particular, as the electron accepting compound, a compound having an anthraquinone structure is preferable. As the compound having an anthraquinone structure include a hydroxyanthraquinone compound, an aminoanthraquinone compound, and an aminohydroxyanthraquinone compound are preferable, and specifically, for example, anthraquinone, alizarin, quinizarin, antharufine, purpurin, and the like are preferable.

The electron accepting compound may be contained by being dispersed in the undercoating layer together with the inorganic particles or may be contained in a state of being attached to the surfaces of the inorganic particles.

Examples of a method of attaching the electron accepting compound to the surfaces of the inorganic particles include a dry method or a wet method.

The dry method is, for example, a method in which while stirring inorganic particles with a mixer or the like having a large shear force, an electron accepting compound is dropped directly or by being dissolved in an organic solvent, and sprayed together with dry air or nitrogen gas to attach the electron accepting compound to the surfaces of the inorganic particles. When dropping or spraying the electron accepting compound, the dropping or spraying the electron accepting compound may be carried out at a temperature equal to or lower than a boiling point of the solvent. After dropping or spraying the electron accepting compound, baking may further be carried out at 100° C. or higher. Baking is not particularly limited as long as the baking is carried out at a temperature and time at which electrophotographic characteristics are obtained.

The wet method is, for example, a method in which an electron accepting compound is added while dispersing inorganic particles in a solvent by stirring, ultrasonic wave, sand mill, attritor, ball mill, or the like, and is stirred or dispersed, and then the solvent is removed to attach the electron accepting compound to the surfaces of the inorganic particles. In the solvent removal method, the solvent is removed, for example, by filtration or distillation. After removing the solvent, baking may further be carried out at 100° C. or higher. Baking is not particularly limited as long as the baking is carried out at a temperature and time at which electrophotographic characteristics are obtained. In the wet method, moisture contained in the inorganic particles may be removed before adding the electron accepting compound. Examples of this method include a method of removing the moisture while stirring and heating in a solvent, and a method of removing the moisture by azeotropic distillation with a solvent.

The attachment of the electron accepting compound may be carried out before or after the inorganic particles are subjected to the surface treatment with the surface treatment agent. Also, the attachment of the electron accepting compound and the surface treatment with the surface treatment agent may be carried out at the same time.

A content of the electron accepting compound may be, for example, from 0.01% by weight to 20% by weight, and is preferably from 0.01% by weight to 10% by weight in the inorganic particles.

Examples of the binder resin used for the undercoating layer include known polymer compounds such as an acetal resin (such as polyvinyl butyral), a polyvinyl alcohol resin, a polyvinyl acetal resin, a casein resin, a polyamide resin, a cellulose resin, gelatin, a polyurethane resin, a polyester resin, an unsaturated polyester resin, a methacrylic resin, an acrylic resin, a polyvinyl chloride resin, a polyvinyl acetate resin, a vinyl chloride-vinyl acetate-maleic anhydride resin, a silicone resin, a silicone-alkyd resin, a urea resin, a phenol resin, a phenol-formaldehyde resin, a melamine resin, a urethane resin, an alkyd resin, and an epoxy resin; a zirconium chelate compound; a titanium chelate compound; an aluminum chelate compound; a titanium alkoxide compound; an organic titanium compound; and known materials such as a silane coupling agent.

Examples of the binder resin used for the undercoating layer also include a charge transporting resin having a charge transporting group and a conductive resin (such as polyaniline).

Among these resins, as the binder resin used for the undercoating layer, resin insoluble in the coating solvent of the upper layer is preferable. In particular, thermosetting resins such as a urea resin, a phenol resin, a phenol-formaldehyde resin, a melamine resin, a urethane resin, an unsaturated polyester resin, an alkyd resin, and an epoxy resin; and a resin obtained by reaction of at least one resin selected from the group consisting of a polyamide resin, a polyester resin, a polyether resin, a methacrylic resin, an acrylic resin, a polyvinyl alcohol resin, and a polyvinyl acetal resin with a curing agent are preferable.

In a case where two or more of these curing resins are used in combination, a mixing ratio thereof is set as needed.

The undercoating layer may also contain electron transport material.

In addition, other electron transport materials may be used in combination. Examples of the electron transport material include: quinone compounds such as p-benzoquinone, chloranil, bromanil, and anthraquinone; a tetracyanoquinodimethane compound; a fluorenone compound such as 2,4,7-trinitrofluorenone; a xanthone compound; a benzophenone compound; a cyanovinyl compound; and an ethylene compound.

Specifically, Examples of the electron transport material also include the electron transport materials ET-1 to ET-9 described in the section of [Singlelayer Type Photosensitive Layer].

A content of the electron transport material may be, for example, from 1% by weight to 50% by weight, is preferably from 5% by weight to 40% by weight, and is more preferably 10% by weight to 30% by weight, based on the total solid content.

The undercoating layer may also contain various additives in order to improve environmental stability and improve image quality.

Examples of the additives include known materials such as an electron transporting pigment of a polycyclic condensed type or an azo type, a zirconium chelate compound, a titanium chelate compound, an aluminum chelate compound, a titanium alkoxide compound, an organic titanium compound, and a silane coupling agent. The silane coupling agent is used for a surface treatment of the inorganic particles as described above, but may be added to the undercoating layer as an additive.

Examples of the silane coupling agent as the additive include vinyltrimethoxysilane, 3-methacryloxypropyl-tris(2-methoxyethoxy)silane, 2-(3,4-epoxycyclohexyl)ethyltrimethoxysilane, 3-glycidoxypropyltrimethoxysilane, vinyltriacetoxysilane, 3-mercaptopropyltrimethoxysilane, 3-aminopropyltriethoxysilane, N-2-(aminoethyl)-3-aminopropyltrimethoxysilane, N-2-(aminoethyl)-3-aminopropylmethyldimethoxysilane, N,N-bis(2-hydroxyethyl)-3-aminopropyltriethoxysilane, and 3-chloropropyltrimethoxysilane.

Examples of the zirconium chelate compound include zirconium butoxide, zirconium ethyl acetoacetate, zirconium triethanolamine, acetylacetonate zirconium butoxide, ethyl acetoacetate zirconium butoxide, zirconium acetate, zirconium oxalate, zirconium lactate, zirconium phosphonate, zirconium octanoate, zirconium naphthenate, zirconium laurate, zirconium stearate, zirconium isostearate, methacrylate zirconium butoxide, stearate zirconium butoxide, and isostearate zirconium butoxide.

Examples of the titanium chelate compound include tetraisopropyl titanate, tetra-n-butyl titanate, butyl titanate dimer, tetra(2-ethylhexyl) titanate, titanium acetylacetonate, polytitanium acetylacetonate, titanium octylene glycolate, titanium lactate ammonium salt, titanium lactate, titanium lactate ethyl ester, titanium triethanolaminate, and polyhydroxy titanium stearate.

Examples of the aluminum chelate compound include aluminum isopropylate, monobutoxyaluminum diisopropylate, aluminum butyrate, diethyl acetoacetate aluminum diisopropylate, and aluminum tris (ethyl acetoacetate).

These additives may be used alone or used as a mixture or a polycondensate of plural compounds.

The undercoating layer may have a Vickers hardness of 35 or higher.

In order to prevent a moire fringe from occurring, surface roughness (ten-point average roughness) of the undercoating layer may be adjusted from $1/(4n)$ (n is a refractive index of an upper layer) of the exposure laser wavelength $\lambda$ to $\frac{1}{2}$ thereof.

In order to adjust the surface roughness, resin particles or the like may be added to the undercoating layer. Examples of the resin particles include silicone resin particles and crosslinked polymethylmethacrylate resin particles. Further, in order to adjust the surface roughness, the surface of the undercoating layer may be polished. Examples of a polishing method include buffing, sandblasting treatment, wet honing, and grinding treatment.

Formation of the undercoating layer is not particularly limited and a known forming method is used. For example, a coating film of an undercoating layer-forming coating liquid obtained by adding the above components to a solvent is formed, and the coating film is dried to form the undercoating layer by heating as needed.

Examples of the solvent for preparing the undercoating layer-forming coating liquid include known organic solvents such as alcohol solvent, aromatic hydrocarbon solvent, halogenated hydrocarbon solvent, ketone solvent, ketone alcohol solvent, ether solvent, and ester solvent.

Specific examples of these solvents include usual organic solvents such as methanol, ethanol, n-propanol, iso-propanol, n-butanol, benzyl alcohol, methyl cellosolve, ethyl cellosolve, acetone, methyl ethyl ketone, cyclohexanone, methyl acetate, ethyl acetate, n-butyl acetate, dioxane, tetrahydrofuran, methylene chloride, chloroform, chlorobenzene, and toluene.

Examples of a method for dispersing inorganic particles when preparing the undercoating layer-forming coating liquid include known methods such as a roll mill, a ball mill, a vibration ball mill, an attritor, a sand mill, a colloid mill, and a paint shaker.

Examples of a method for applying the undercoating layer-forming coating liquid onto the conductive substrate include normal methods such as a blade coating method, a wire bar coating method, a spray coating method, a dipping coating method, a bead coating method, an air knife coating method, and a curtain coating method.

A film thickness of the undercoatinglayer is set, for example, preferably 3 µm or more, and more preferably from 10 µm to 50 µm.

—Image Forming Apparatus and Process Cartridge—

With respect to the image forming apparatus and the process cartridge according to the second aspect, all the description regarding the image forming apparatus and the process cartridge according to the first aspect may be adopted.

EXAMPLES

Hereinafter, the present invention will be described in more detail with reference to Examples, but the present invention is not limited to the following Examples. Unless otherwise specified, "part" means "part by weight".

—Preparation of Electrophotographic Photoreceptor—

Example 1

(Preparation of Undercoating Layer)

34 parts by weight of Imide Compound (1-9) represented by Formula (1) are mixed with a solution prepared by dissolving 20 parts by weight of a curing resin raw material (blocked isocyanate, SUMIDUR BL 3175, manufactured by Sumitomo Bayer Urethane Co., Ltd., solid content 75%) and 7.5 parts by weight of butyral resin (S-LEC BL-1, manufactured by Sekisui Chemical Co., Ltd.) in 143 parts by weight of methyl ethyl ketone and dispersed for 120 minutes with a sand mill using 1 mmφ glass beads to obtain a dispersion.

0.005 parts by weight of dioctyltin dilaurate as a catalyst and 10 parts by weight of silicone resin particles (TOSPEARL145, manufactured by GE Toshiba Silicones) are added to the obtained dispersion to obtain an undercoating layer-forming coating liquid. The coating liquid is dipping-applied onto an aluminum substrate by a dipping coating method, and dried and cured at 160° C. for 60 minutes to obtain an undercoating layer 1 having a thickness of 4 µm.

(Preparation of Charge Generation Layer)

A mixture including 15 parts by weight of hydroxygallium phthalocyanine having diffraction peaks at Bragg angles (2θ±0.2°) of at least 7.3°, 16.0°, 24.9°, and 28.0° in an X-ray diffraction spectrum using a Cu Kα characteristic X-ray as the charge generation substance, 10 parts by weight of vinyl chloride-vinyl acetate copolymer resin (VMCH, manufactured by Nippon Unicar Company Limited) as a binder resin, and 200 parts by weight of n-butyl acetate are dispersed by stirring for 4 hours with a sand mill using glass beads having a diameter of 1 mmφ. 175 parts by weight of n-butyl acetate and 180 parts by weight of methyl ethyl ketone are added to the obtained dispersion and stirred to obtain a charge generation layer-forming coating liquid. This charge generation layer-forming coating liquid is dipping-applied onto the undercoating layer. Thereafter, drying is performed at 140° C. for 10 minutes to form a charge generation layer having a film thickness of 0.2 µm.

(Preparation of Charge Transport Layer)

40 parts by weight of charge transporting agent (HT-1), 8 parts by weight of charge transporting agent (HT-2), and 52 parts by weight of polycarbonate resin (A) (viscosity average molecular weight: 50,000) are added to 800 parts by weight of tetrahydrofuran, and dissolved therein. 8 parts by weight of tetrafluoroethylene resin (manufactured by Daikin Industries Ltd., LUBRON L5, average particle diameter of 300 nm) is added thereto and dispersed at 5500 rpm for 2 hours using a homogenizer (ULTRA-TURRAX manufactured by IKA) to obtain a charge transport layer-forming coating liquid. This coating liquid is applied onto the above-described charge generation layer. Thereafter, drying is performed at 140° C. for 40 minutes to form a charge transport layer having a film thickness of 27 µm. In this manner, an electrophotographic photoreceptor 1 is obtained.

Polycarbonate resin (A)

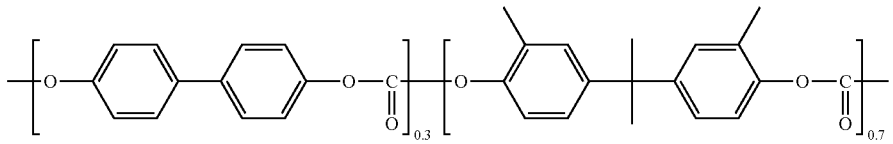

(HT-1)

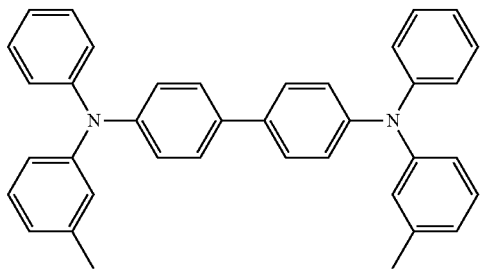

(HT-2)

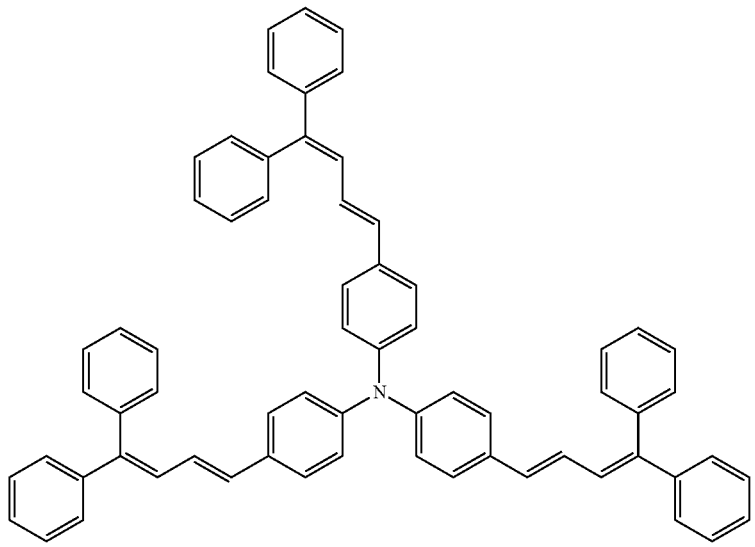

Examples 2 to 9

Except that a kind of the imide compound is changed from the imide compound (1-9) represented by Formula (1) to the formulation shown in Table 1 in an undercoating layer forming step of Example 1, the same operation as in Example 1 are performed to obtain each electrophotographic photoreceptor.

Example 10

The same operation as in Example 1 is performed except that the undercoating layer forming step of Example 1 is changed to the following step with a kind and amount of the curing resin being changed to 30 parts by weight of a phenol resin, to thereby obtain a electrophotographic photoreceptor.

90 parts by weight of methyl ethyl ketone and 50 parts by weight of isopropanol are added to 30 parts by weight of resol type phenol resin (PL-4852, manufactured by Gunei Chemical Industry Co., Ltd., nonvolatile component 75%). 34 parts by weight of the imide compound (1-9) represented by Formula (1) is mixed thereto and dispersed with a sand mill for 90 minutes using 1 mmφ glass beads to obtain the undercoating layer-forming coating liquid. The coating liquid is dipping-applied onto an aluminum substrate by a dipping coating method, and dried and cured at 160° C. for 60 minutes to obtain an undercoating layer having a thickness of 4 µm.

Example 11

The same operation as in Example 1 is performed except that the undercoating layer forming step of Example 1 is changed to the following step while the undercoating layer containing the charge transport material and the curing resin further includes metal oxide particles to thereby obtain an electrophotographic photoreceptor.

100 parts by weight of zinc oxide (manufactured by Tayca Corporation, average particle diameter: 70 nm, specific surface area value: 15 m²/g) is mixed to 600 parts by weight of toluene by stirring, and 1.2 parts by weight of a silane coupling agent (KBM 602, manufactured by Shin-Etsu Chemical Co., Ltd.) is added thereto and stirred for 2 hours. Thereafter, toluene is distilled off by distillation under reduced pressure and baked at 125° C. for 2 hours to obtain zinc oxide surface-treated with a silane coupling agent.

50 parts by weight of the zinc oxide after surface treated, 15 parts by weight of curing agent (blocked isocyanate, SUMIDUR BL 3175, manufactured by Sumitomo Bayer Urethane Co., Ltd.), and 15 parts by weight of butyral resin (S-LEC BL-1, manufactured by Sekisui Chemical Co., Ltd.) are dissolved in 90 parts by weight of methyl ethyl ketone. 35 parts by weight of obtained solution is mixed with 50 parts by weight of methyl ethyl ketone and 10 parts by weight of the electron transporting compound (1-9) and dispersed with a sand mill for 60 minutes using 1 mmφ glass beads to obtain a dispersion.

0.005 parts by weight of dioctyltin dilaurate as a catalyst and 30 parts by weight of silicone resin particles (TOSPEARL145, manufactured by GE Toshiba Silicones) are added to the obtained dispersion to obtain an undercoating layer-forming coating liquid. The coating liquid is applied onto an aluminum substrate by a dipping coating method, and dried and cured at 160° C. for 60 minutes to obtain an undercoating layer having a thickness of 10 µm.

Example 12

In an undercoating layer forming step of Example 11, except that 50 parts by weight of zinc oxide after surface treated is changed 8 parts by weight of zinc oxide after surface treated, the same operation as in Example 11 are performed to obtain an electrophotographic photoreceptor.

Example 13

Except that 20 parts by weight of a curing resin raw material (blocked isocyanate, SUMIDUR BL 3175, manufactured by Sumitomo Bayer Urethane Co., Ltd., solid content 75%) and 7.5 parts by weight of butyral resin (S-LEC BL-1, manufactured by Sekisui Chemical Co., Ltd.) are changed to 27.5 parts by weight of a modified nylon resin (LUCKAMIDE 5003, manufactured by DIC Corporation) and the solvent is changed to methanol in the undercoating layer forming step of Example 1, the same operation as in Example 1 are performed to obtain the electrophotographic photoreceptor.

Comparative Examples 1 to 3

The same operation as in Example 1 is performed except that, with respect to a kind of the imide compound in an undercoating layer forming step of Example 1, the imide compound (1-9) represented by Formula (1) is changed to the following compound (A), compound (B), or compound (C), to thereby obtain each electrophotographic photoreceptor.

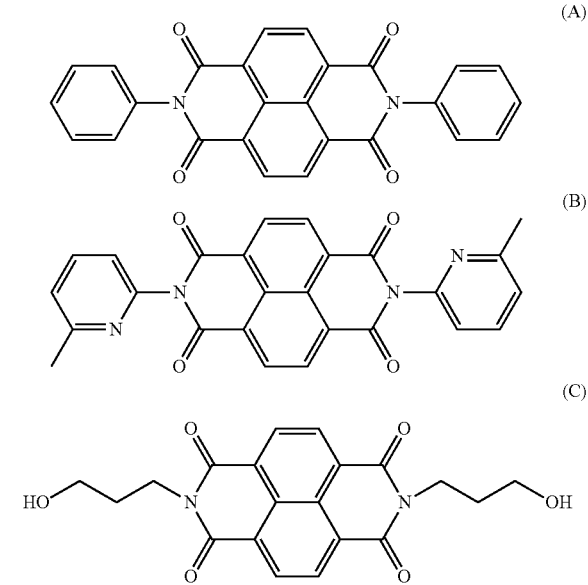

Comparative Example 4

The same operation as in Example 1 is performed except that the imide compound is not used in the undercoating layer forming step of Example 1, to thereby obtain an electrophotographic photoreceptor.

[Evaluation]

The following evaluation is performed for the electrophotographic photoreceptors prepared as above. Evaluation results are shown in Table 1.

—Black Spot Image Quality Evaluation—

For an image quality evaluation, the electrophotographic photoreceptor is mounted on a copying machine "DocuCentre C5570" (manufactured by Fuji Xerox Co., Ltd.) and 20,000 sheets of 20% halftone images are printed under an environment of a room temperature of 30° C. and a humidity of 85%. After 10 hours, printing is conducted again, and the presence or absence of black spots is evaluated with respect to an image on the 10th sheet with reference to the following criteria.

A: No black spot.
B: 10 spots or less, which is acceptable for image quality.
C: 10 spots or more occur, which becomes a problem in practical use.

—Residual Potential Evaluation—

In the above-described conditions for evaluating black spot image quality, a difference ΔV between an initial surface potential and a surface potential after printing 20,000 sheets is calculated for evaluation.

A: 50 V or less, which is no problem.
B: more than 50 V and less than 80 V, which is acceptable.
C: 80 V or more, which becomes a problem in image quality.

TABLE 1

| | Imide compound | | Curing resin | | Evaluation | |
|---|---|---|---|---|---|---|
| | Kinds | Parts by weight | Kinds | Parts by weight | Black spot image quality evaluation | Residual potential evaluation |
| Example 1 | 1-9 | 34 | Polyurethane | 20 | A | A |
| Example 2 | 1-6 | 34 | Polyurethane | 20 | A | A |
| Example 3 | 1-8 | 34 | Polyurethane | 20 | A | A |
| Example 4 | 1-15 | 34 | Polyurethane | 20 | A | A |
| Example 5 | 1-16 | 34 | Polyurethane | 20 | A | A |
| Example 6 | 1-23 | 34 | Polyurethane | 20 | A | A |
| Example 7 | 2-7 | 34 | Polyurethane | 20 | A | A |
| Example 8 | 2-8 | 34 | Polyurethane | 20 | A | A |
| Example 9 | 2-9 | 34 | Polyurethane | 20 | A | A |
| Example 10 | 1-9 | 34 | Phenol resin | 30 | A | A |
| Example 11 | 1-9 | 10 | Polyurethane | 15 | A | A |
| Example 12 | 1-9 | 10 | Polyurethane | 15 | B | B |
| Example 13 | 1-9 | 34 | Modified nylon resin | 27.5 | B | B |
| Comparative Example 1 | Compound (A) | 34 | Polyurethane | 20 | C | C |
| Comparative Example 2 | Compound (B) | 34 | Polyurethane | 20 | C | C |
| Comparative Example 3 | Compound (C) | 34 | Polyurethane | 20 | C | B |
| Comparative Example 4 | — | — | Polyurethane | 20 | C | C |

From the results shown in Table 1, it is found that the electrophotographic photoreceptors according to the exemplary embodiment prevent an increase of the residual potential which may be caused when images are formed repeatedly, as compared with the electrophotographic photoreceptor of the comparative examples. In addition, it is found that the electrophotographic photoreceptors according to the exemplary embodiment also prevent black spot image quality from occurring, as compared with the electrophotographic photoreceptor of the comparative examples.

—Synthesis Example of Specific Imide Compound—
(Synthesis Example: Exemplary Compound 1A-23)

Figure 5:
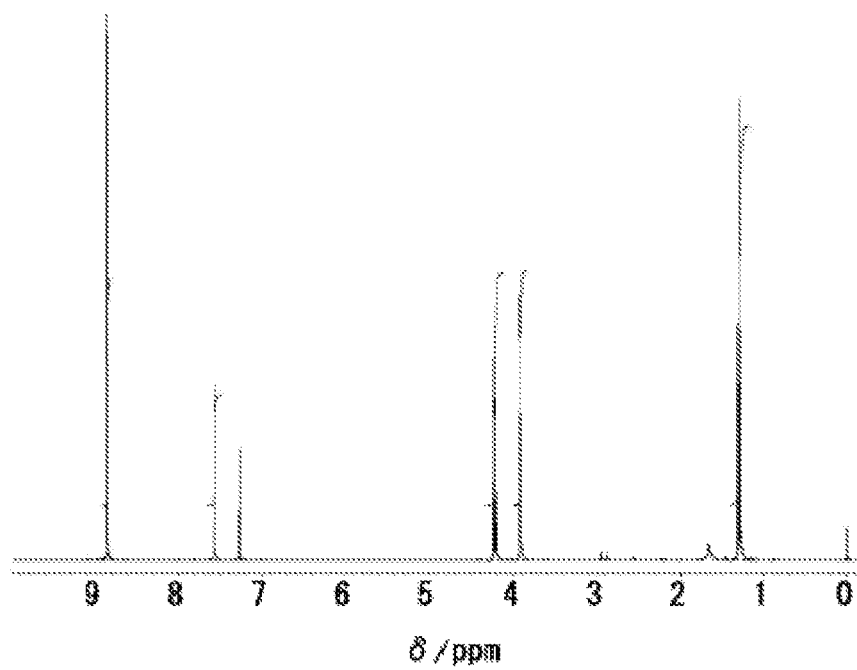
FIG. 5 is a graph showing a $^1$H-NMR spectrum of Exemplary Compound (1A-23)

26.82 g (0.1 mol) of naphthalene-1,4,5,8-tetracarboxylic dianhydride is dissolved in 150 ml of N,N-dimethylformamide, and 39.11 g (0.21 mol) of ethyl 2-amino-4-thiazolylacetate is added thereto, and the mixture is stirred at 150° C. for 3 hours. A reaction solution is cooled to a room temperature, and the precipitated crystals are filtered, and washed with 500 ml of methanol to obtain 48 g of gray white crystals. The obtained crystals are dissolved in 1 L of chloroform and purified by silica gel chromatography to obtain 39 g of light yellow crystals of the specific imide compound (Exemplary Compound 1A-23) as a targeted substance. A melting temperature is 257° C. to 259° C. FIG. 5 shows $^1$H-NMR spectrum of the obtained specific imide compound (Exemplified Compound 1A-23) in deuterated chloroform solvent at room temperature (25° C.).

Exemplary compound (1A-23)

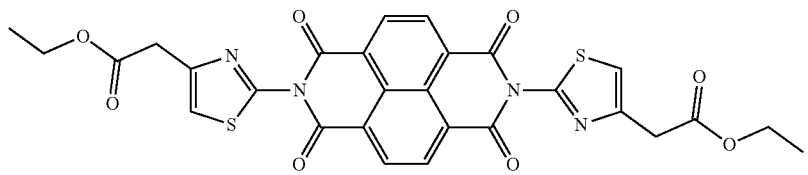

Synthesis Example: Exemplary Compound 1A-30

6 g (0.01 mol) of Exemplary Compound 1A-23 obtained as above is suspended in 70 ml of n-octanol, and 0.1 g of sulfuric acid is added thereto. The mixture is heated and stirred at 140° C. for 5 hours in a flask equipped with a Dean-Stark apparatus. The reaction solution is cooled to a room temperature, and the precipitated crystals are filtered, and washed with methanol. The obtained crystals are dried with a vacuum drier to obtain 4.6 g of the specific imide compound (Exemplary Compound 1A-30). A melting temperature is 210° C. to 212° C. FIG. 6 shows $^1$H-NMR spectrum of the obtained specific imide compound (Exemplified Compound 1A-30) in deuterated chloroform solvent at room temperature (25° C.).

Exemplary compound (1A-30)

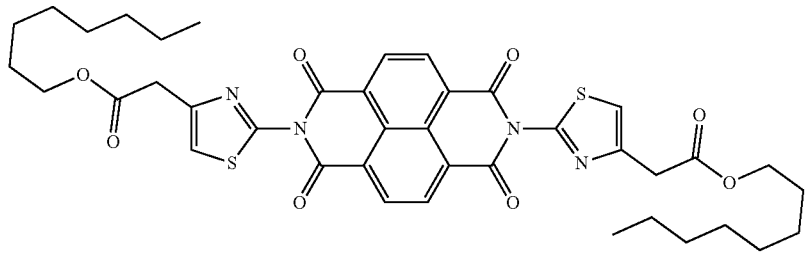

Synthesis Example: Exemplary Compound 1A-31

Except that 60 ml of phenethyl alcohol is used in place of 70 ml of n-octanol in the synthesis of Exemplary Compound 1A-30, reaction is performed in the same manner to obtain 3.9 g of the specific imide compound (Exemplary Compound 1A-31). A melting temperature is 215° C. to 219° C. FIG. 7 shows $^1$H-NMR spectrum of the obtained specific imide compound (Exemplified Compound 1A-31) in deuterated chloroform solvent at room temperature (25° C.).

Exemplary compound (1A-31)

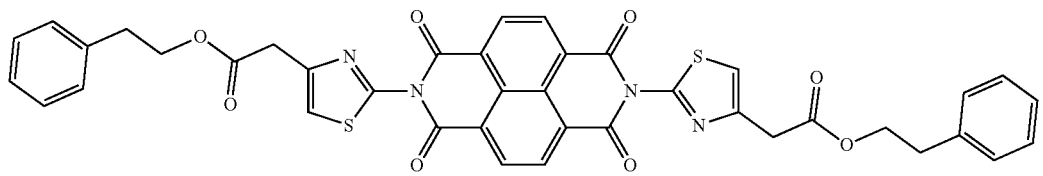

Synthesis Example: Exemplary Compound 1A-33

30 ml of 1-ethoxy-2-propanol is used in place of 70 ml of n-octanol in the synthesis of Exemplary Compound 1A-30, and 60 ml of toluene is further added thereto. The mixture is heated and refluxed for 4 hours. The reaction solution is cooled to a room temperature. 500 ml of methanol is added to the reaction solution to precipitate crystals, followed by filtration. The obtained crystals are purified by silica gel chromatography using a mixed solvent (toluene/tetrahydrofuran=3/1) to obtain 2.7 g of the specific imide compound (Exemplary Compound 1A-33). A melting temperature is 184° C. to 187° C. FIG. 8 shows $^1$H-NMR spectrum of the obtained specific imide compound (Exemplified Compound 1A-33) in deuterated chloroform solvent at room temperature (25° C.).

Exemplary compound (1A-33)

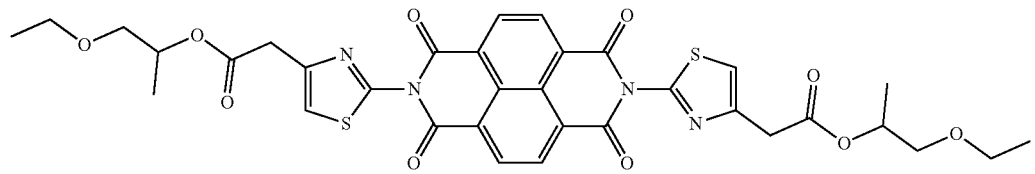

Example 1A (Preparation of Photoreceptor)

2 parts by weight of hydroxygallium phthalocyanine having diffraction peaks at Bragg angles (2θ±0.2°) of at least 7.3°, 16.0°, 24.9°, and 28.0° in an X-ray diffraction spectrum using a Cu Kα characteristic X-ray as the charge generation substance, 5 parts by weight of the specific imide compound (Exemplary Compound 1A-23) as the electron transport material, 49 parts by weight of copolymer type polycarbonate resin (B) (viscosity average molecular weight of 50,000) as the binder resin, 200 parts by weight of tetrahydrofuran, and 100 parts by weight of monochlorobenzene are mixed. This mixture is dispersed for 6 hours by a sand mill using glass beads having a diameter of 1 mmφ. 31 parts by weight of a hole transport compound (HT-7) and 0.001 parts by weight of silicone oil KP 340 (manufactured by Shin-Etsu Chemical Co., Ltd) are added to the obtained dispersion, and stirred overnight to obtain a photosensitive layer-forming coating liquid.

The photosensitive layer-forming coating liquid obtained as described above is applied onto an aluminum substrate having a diameter of 30 mm by a dipping coating method and dried at 140° C. for 1 hour to form a singlelayer type photosensitive receptor having a film thickness of 26 μm.

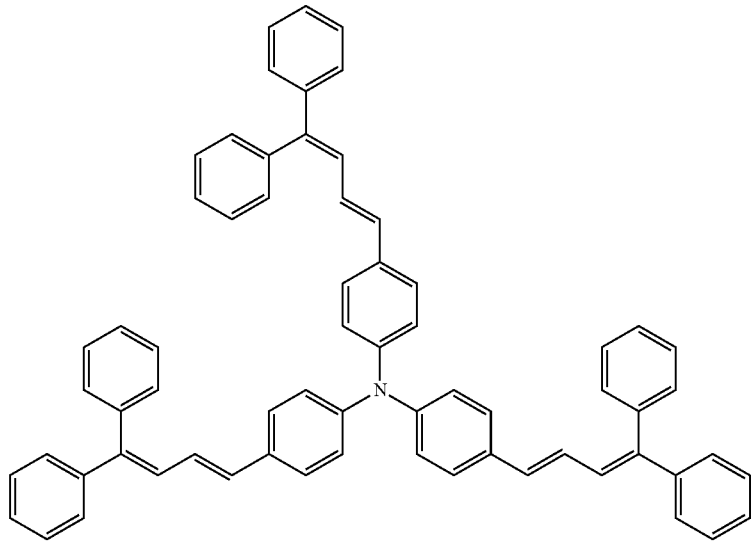

Polycarbonate resin (B)

(1A-23)

(HT-7)

Example 2A to 6A

Except that a kind of the electron transport material is changed from Exemplary Compound 1A-23 to other specific imide compound shown in Table 2, a singlelayer type photosensitive receptor is obtained in the same manner as Example 1A.

Examples 7A to 10A

Except that kinds of the electron transport material, the charge generation material, and the hole transport material are changed to other materials shown in Table 2, a single-layer type photosensitive receptor is obtained in the same manner as Example 1A.

Comparative Examples 1A to 4A

Except that kinds of the electron transport material, the hole transport material, and charge generation material are changed to other materials shown in Table 2, a singlelayer type photosensitive receptor is obtained in the same manner as Example 1A.

Except that compounds corresponding to Comparative Compounds 1A to 4A are used as raw materials in the synthesis example of Exemplary Compound 1A-23 which is the specific imide compound, Comparative Compounds 1A to 4A are synthesized in the same manner.

A: blurring of images does not occur.
B: Although some slight faintness may be confirmed on a paper short side, there is no problem in image quality.
C: White spots occur obviously, which becomes a problem in practical use.

[Charge Retention Characteristic Evaluation]

For the electric characteristics of the electrophotographic photoreceptor, a surface potential probe is provided in a region to be measured at a position 1 mm away from the surface of the electrophotographic photoreceptor using an electrostatic voltmeter (TREK 334, manufactured by Trek Japan), the surface potential after charging is set to −720 V, and the surface potential after outputting 15,000 sheets is measured. Thereafter, an evaluation is performed with reference to the following criteria. Drop in charging potential is evaluated.

A: Potential drop is 15 V or less, which is no problem.
B: Potential drop is more than 15 V and less than 25 V, which is no problem since it is an adjustable range.
C: Potential drop is 25 V or more, which is not adjustable.

Comparative compound 1A

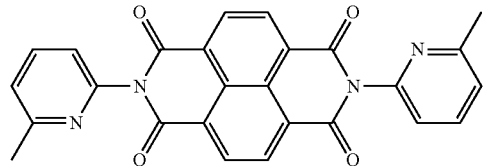

Comparative compound 2A

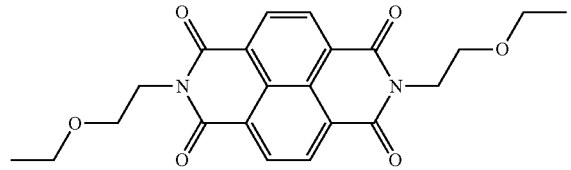

Comparative compound 3A

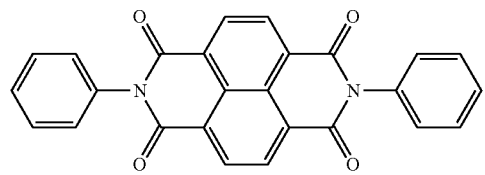

Comparative compound 4A

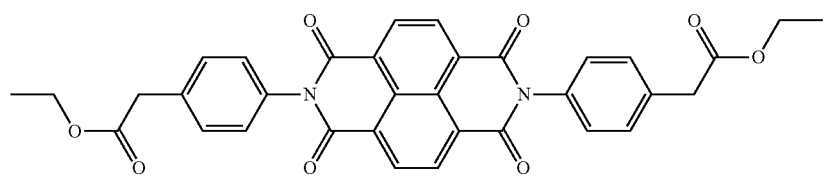

—Evaluation—

The electrophotographic photoreceptors of Examples 1A to 10A and Comparative Examples 1A to 4A prepared above are mounted on DocuCentre-V C7775 (manufactured by Fuji Xerox Co., Ltd.), and the following evaluations are carried out. Evaluation results are shown in Table 2.

[Blurry Image Quality Evaluation (Density Unevenness)]

An image quality evaluation is performed after 6,000 sheets of 100% black solid images are output using HL-2360D (manufactured by Brother Industries, Ltd.) under an environment of a room temperature of 28° C. and a humidity of 85%. The presence or absence of blurring of the image on the 6,000-th sheet is evaluated with reference to the following criteria.

[Crack Resistance Evaluation]

0.4 ml of 1 wt % hexane solution of oleic acid is sprayed onto the electrophotographic photoreceptor and allowed to stand at a room temperature (25° C.) for 2 weeks. Thereafter, fractures (cracks) on the surface of the electrophotographic photoreceptor are evaluated with reference to the following criteria. The microscope used is a digital microscope (model number: VHX-700, manufactured by Keyence Corporation). Observation is performed by magnifying 700 times.

A: When observing with a microscope, there is no problem.
B: When observing with a microscope, fine cracks are observed, but which is no problem in practical use.
C: It is possible to visually confirm cracks.

TABLE 2

|  | Charge generation material | Hole transport material | Electron transport material | Blurr evaluation | Charge retention characteristic | Crack resistance |
| --- | --- | --- | --- | --- | --- | --- |
| Example 1A | hydroxygallium phthalocyanine | HT-7 | Exemplary Compound 1A-23 | A | A | A |

TABLE 2-continued

|  | Charge generation material | Hole transport material | Electron transport material | Blurr evaluation | Charge retention characteristic | Crack resistance |
|---|---|---|---|---|---|---|
| Example 2A | hydroxygallium phthalocyanine | HT-7 | Exemplary Compound 1A-30 | A | A | A |
| Example 3A | hydroxygallium phthalocyanine | HT-7 | Exemplary Compound 1A-31 | A | A | A |
| Example 4A | hydroxygallium phthalocyanine | HT-7 | Exemplary Compound 1A-33 | A | A | A |
| Example 5A | hydroxygallium phthalocyanine | HT-7 | Exemplary Compound 1A-45 | A | A | A |
| Example 6A | hydroxygallium phthalocyanine | HT-7 | Exemplary Compound 1A-55 | A | A | A |
| Example 7A | chlorogallium phthalocyanine | HT-1 | Exemplary Compound 1A-31 | A | A | A |
| Example 8A | chlorogallium phthalocyanine | HT-13 | Exemplary Compound 1A-33 | A | A | A |
| Example 9A | X-type metal-free phthalocyanine | HT-7 | Exemplary Compound 1A-31 | A | A | A |
| Example 10A | X-type metal-free phthalocyanine | HT-7 | Exemplary Compound 1A-33 | A | A | A |
| Comparative Example 1A | hydroxygallium phthalocyanine | HT-7 | Comparative Compound 1A | C | B | C |
| Comparative Example 2A | hydroxygallium phthalocyanine | HT-7 | Comparative Compound 2A | B | C | B |
| Comparative Example 3A | hydroxygallium phthalocyanine | HT-7 | Comparative Compound 3A | C | C | C |
| Comparative Example 4A | chlorogallium phthalocyanine | HT-7 | Comparative Compound 4A | B | C | B |

From the results, it is found that the electrophotographic photoreceptor according to Examples 1A to 10A has improved crack resistance, as compared with the electrophotographic photoreceptor of Comparative Examples 1A to 4A.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An electrophotographic photoreceptor comprising:
a conductive substrate;
a photosensitive layer provided on the conductive substrate; and
an undercoating layer that is provided between the conductive substrate and the photosensitive layer and includes a charge transport material containing at least one of imide compounds represented by Formula (1) or (2):

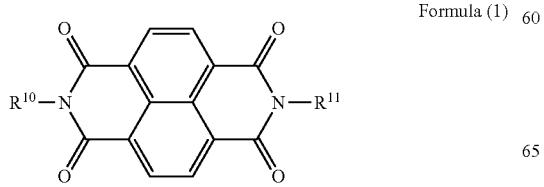

Formula (1)

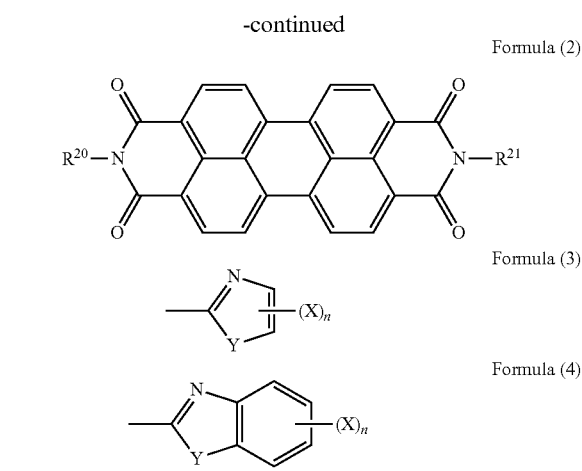

(in Formulas (1) and (2), $R^{10}$, $R^{11}$, $R^{20}$, or $R^{21}$ independently represents a group represented by Formula (3) or (4); and
in Formulas (3) and (4), X represents a monovalent organic group having at least one of an alkyl group, an alkylene group, an ether group, an ester group, and a keto group, a halogen atom, a nitro group, an aralkyl group, or an aryl group, Y represents a sulfur atom or an oxygen atom, n represents an integer of 0 to 2, and when n represents 2, two X's may be the same or different).

2. The electrophotographic photoreceptor according to claim 1,
wherein X in Formula (3) or (4) in the imide compound represents a monovalent organic group having at least one of an alkyl group, an alkylene group, an ether group, an ester group, and a keto group.

3. The electrophotographic photoreceptor according to claim 1,
wherein a content of the imide compound represented by Formula (1) or (2) in the undercoating layer is from 10% by weight to 80% by weight.

4. The electrophotographic photoreceptor according to claim 1,
wherein the undercoating layer contains at least one kind of metal oxide particles selected from the group consisting of zinc oxide, titanium oxide, and tin oxide.

5. The electrophotographic photoreceptor according to claim 4,
wherein a content of the metal oxide particles in the undercoating layer is from 10% by weight to 80% by weight.

6. The electrophotographic photoreceptor according to claim 1,
wherein the undercoating layer further contains a curing resin, and
the curing resin is at least one selected from the group consisting of a phenol resin, a melamine resin, a guanamine resin, and a urethane resin.

7. The electrophotographic photoreceptor according to claim 6,
wherein the curing resin contains a urethane resin.

8. A process cartridge that is detachable from an image forming apparatus, the process cartridge comprising:
the electrophotographic photoreceptor according to claim 1.

9. An image forming apparatus comprising:
the electrophotographic photoreceptor according to claim 1;
a charging unit that charges a surface of the electrophotographic photoreceptor;
an electrostatic latent image forming unit that forms an electrostatic latent image on a charged surface of the electrophotographic photoreceptor;
a developing unit that develops the electrostatic latent image formed on the surface of the electrophotographic photoreceptor with a developer including toner to form a toner image; and
a transfer unit that transfers the toner image onto a surface of a recording medium.

* * * * *